US006610300B1

(12) United States Patent
Segers et al.

(10) Patent No.: US 6,610,300 B1
(45) Date of Patent: Aug. 26, 2003

(54) *CLOSTRIDIUM PERFRINGENS* VACCINE

(75) Inventors: Ruud Philip Antoon Maria Segers, Boxmeer (NL); Nicolas Robin Waterfield, Cambridge (GB); Peer Lyng Frandsen, Holte (DK); Jeremy Mark Wells, Cambridge (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/100,703

(22) Filed: Jun. 19, 1998

(30) Foreign Application Priority Data

Jun. 20, 1997 (EP) ........................................... 97201888

(51) Int. Cl.$^7$ ........................ A61K 39/00; A61K 39/38; A61K 39/02; A61K 39/08; C07K 1/00

(52) U.S. Cl. ................................ 424/184.1; 424/234.1; 424/236.1; 424/239.1; 424/247.1; 530/350

(58) Field of Search ....................... 530/350; 424/184.1, 424/234.1, 236.1, 239.1, 247.1

(56) References Cited

U.S. PATENT DOCUMENTS 5,817,317 A * 10/1998 Titball et al.

FOREIGN PATENT DOCUMENTS

| | | |
|---|---|---|
| GB | 958574 | 5/1964 |
| GB | 2030451 | 4/1980 |
| WO | WO 9323543 | 11/1993 |
| WO | WO 9717521 | 6/1995 |
| WO | WO 97/34001 | 9/1997 |

OTHER PUBLICATIONS

Hunter et al., *Infection and Immunity*, 61:9:3958–3965, 1993.

Sakurai and Duncan, *Infection and Immunity*, 18:3:741–745, 1977.

* cited by examiner

*Primary Examiner*—Mark Navarro
(74) *Attorney, Agent, or Firm*—William M. Blackstone

(57) ABSTRACT

The present invention relates to detoxified immunogenic derivatives of *Clostridium perfringens* β-toxin or an immunogenic fragment thereof that have as a characteristic that they carry a mutation in the β-toxin amino acid sequence, not found in the wild-type β-toxin amino acid sequence. The invention also relates to genes encoding such β-toxins, as well as to expression systems expressing such β-toxins. Moreover, the invention relates to bacterial expression systems expressing a native β-toxin. Finally, the invention relates to vaccines based upon detoxified immunogenic derivatives of *Clostridium perfringens* β-toxin, and methods for the preparation of such vaccines.

14 Claims, 58 Drawing Sheets

```
                                                                                          Dde I
                                                              Fnu4H I                    BpuII02 I
                                                              BspW I                      NspB II
                                                       Dde I   Bbv I                      AciI I
                                                       BspW I  Fnu4H I                     |||
                                                       Alu I   Bbv I                       |||
                                                       |||     |||                         |||
ACAGCAAATGGGTCGGATCCGGCTAACAAAGCCCGAAAGGAAGCTGAGTGTGGCTGCCACCGCTGAGCAATAA
TGTCGTTTACCCAGCCTAGGCCGATTGTTTCGGGCTTTCCTTCGACTCACACCGACGGTGGCGACTCGTTATT
                                                                                          320
              BspW I                                   287    297
       Aci I   Fnu4H I                                 288    297    307
BstU I  |||    Bbv I                                   289    300    307
 |||    |||    |||                                                   309
 |||    |||    |||                                                   310
 254
 255
 255
 257
 257
 257
 257
 258                 264
                     264
                     267
```

Msp I
Hpa II
Sau3A I
Mbo I
Dpn II
Dpn I
Alw I
Nla IV
BstY I
BamH I
Alw I

```
                           261
                           261
                        Hae III
                       Sau96 I
                      Nla IV
                      EcoO109 I
              Sty I   Mnl I
Bfa I         BsaJ I  Bsl I            Mnl I                   Mnl I      Mme I    Hinf I
|             |   |||  |               |                       |          |    |  | ||
CTAGCATAACCCCTTGGGGCCTCTAAACGGGTCTTGAGGGGTTTTTTGCTGAAAGGAGGAACtatatccgactagaATCG  400
GATCGTATTGGGGAACCCCGGAGATTTGCCCAGAACTCCCCAAAAAACGACTTTCCTCCTTGatataggctgatctTAGC
|         .   |   |||  |         .     |    .        .         |    .     |  .  |  | || .
321           332      340             356                     376        387      395
              332      340                                                    392
                  336                                                              395
                  336                                                                397
                   337                                                               397
                    338                                                               398

                                              Mse I                  Mse I
                                             Dra I                  Dra I  Tth111 II
                                              ||                     ||     |
ATACGATTTTGAAGTGGCAACAGATAAAAAAAAGCAGTTTAAAATTGTTGCTGAACTTTTAAAACAAGCAAATACAATCA  480
TATGCTAAAACTTCACCGTTGTCTATTTTTTTTCGTCAAATTTTAACAACGACTTGAAAATTTTGTTCGTTTATGTTAGT
         .         .         .        ||.        .        ||.    |    .         .
                                      438                  458    465
                                       439                  459
```

FIG. 1b-3

```
                                                                   Sau3A I
                                                                   Mbo I
                                                                   Dpn II
                                                                 Taq I
                                                           ScrF I
                                                           EcoR II
                                                           Dsa V   Dpn I
                                                           BstN I
                                               Bcg I       BstK I
                                               |           |     | |
TTGTCGCAACAGATAGCGACAGAGAAGGCGAAAACATTGCCTGGTCGATCATTCATAAAGCAAATGCCTTTTCTAAAGAT  560
AACAGCGTTGTCTATCGCTGTCTCTTCCGCTTTTGTAACGGACCAGCTAGTAAGTATTTCGTTTACGGAAAAGATTTCTA
         .         .         |.          |     | |  .         .         .         .
                             509         520
                                         520
                                         520     527
                                         520
                                         520
                                              525
                                                 527
                                                 527
                                                 527
                   Sau3A I                       Sau3A I                    ScrF I
                   Mbo I                         Mbo I                      EcoR II
                   Dpn II                        Dpn II                     Dsa V
                   Dpn I                         Dpn I                      BstN I
  Mae II           Alw I                         Alw I   Aci I     Apo I    BstK I
  |                ||                            |       |         |        |
AAAACGTATAAAAGACTATGGATCAATAGTTTAGAAAAAGATGTGATCCGTAGCGGTTTTCAAAATTTGCAACCAGGAAT  640
TTTTGCATATTTTCTGATACCTAGTTATCAAATCTTTTTCTACACTAGGCATCGCCAAAAGTTTTAAACGTTGGTCCTTA
  |     .          ||        .         .         |    .  |     .   |    .   |     .
  564              580                           605     613       623      633
                    581                          605                        633
                    581                          605                        633
                    581                          605                        633
                    581                          605                        633
```

FIG. 1b-4

```
                  HinP I
                  Hha I
                  |
GAATTACTATCCCTTTTATCAAGAAGCGCAAAAGAAAAACGAAATGATACACCAATCAGTGCAAAAAAAGATATAATGGG   720
CTTAATGATAGGGAAAATAGTTCTTCGCGTTTTCTTTTTGCTTTACTATGTGGTTAGTCACGTTTTTTTCTATATTACCC
                  |
                  666

                                                                                 Mae II
                                             Taq I                 Aci I
                                             |                     |    |
AGATAAGACGGTTCGTGTTCGTGCTGACTTGCACCATATCATAAAAATCGAAACAGCAAAGAATGGCGGAAACGTAAAAG   800
TCTATTCTGCCAAGCACAAGCACGACTGAACGTGGTATAGTATTTTTAGCTTTGTCGTTTCTTACCGCCTTTGCATTTTC
                                             |                     |    |
                                             768                   786
                                                                        792

                                Mse I                             Apo I
              Dde I          Afl II              Bsg I      Mse I
              |              ||                  |          |   |
AAGTTATGGAAATAAGACTTAGAAGCAAACTTAAGAGTGTGTTGATAGTGCAGTATCTTAAAATTTTGTATAATAGGAAT   880
TTCAATACCTTTATTCTGAATCTTCGTTTGAATTCTCACACAACTATCACGTCATAGAATTTTAAAACATATTATCCTTA
              |              ||                  |          |   |
              818            830                 848        858
                              831                              861

Mse I  SfaN I  Apo I  Mse I                 Nla III               Ssp I
|      |       |      |                     |                     |
TGAAGTTAAATTAGATGCTAAAAATTTGTAATTAAGAAGGAGTGATTACATGAACAAAAATATAAAATATTCTCAAAACT   960
ACTTCAATTTAATCTACGATTTTTAAACATTAATTCTTCCTCACTAATGTACTTGTTTTTATATTTTATAAGAGTTTTGA
|      |       |      |                     |                     |
886    894     902    912                   929                   946
```

FIG. 1b-5

```
                     Rsa I
                     Csp6 I                              Mse I
 Mse I              Sca I                       Mun I  Apo I  Dra I
TTTTAACGAGTGAAAAAGTACTCAACCAAATAATAAAACAATTGAATTTAAAAGAAACCGATACCGTTTACGAAATTGGA  1040
AAAATTGCTCACTTTTTCATGAGTTGGTTTATTATTTTGTTAACTTAAATTTTCTTTGGCTATGGCAAATGCTTTAACCT
 963                977                         999   1004  1007
                     978                                     1008
                     978

                                                              Mae II
                   Mse I        Bsr I                        Mae III
ACAGGTAAAGGGCATTTAACGACGAAACTGGCTAAAATAAGTAAACAGGTAACGTCTATTGAATTAGACAGTCATCTATT  1120
TGTCCATTTCCCGTAAATTGCTGCTTTGACCGATTTTATTCATTTGTCCATTGCAGATAACTTAATCTGTCAGTAGATAA
                   1056         1067                         1089
                                                              1092

                                                   Mse I
                      Mse I               Mae III       Hph I        Sfc I
CAACTTATCGTCAGAAAAATTAAAACTGAATACTCGTGTCACTTTAATTCACCAAGATATTCTACAGTTTCAATTCCCTA  1200
GTTGAATAGCAGTCTTTTTAATTTTGACTTATGAGCACAGTGAAATTAAGTGGTTCTATAAGATGTCAAAGTTAAGGGAT
                      1140                1158          1169         1182
                                                1164

     Mnl I
 Tth111 II                                      Mse I          Mse I
ACAAACAGAGGTATAAAATTGTTGGGAGTATTCCTTACCATTTAAGCACACAAATTATTAAAAAAGTGGTTTTTGAAAGC  1280
TGTTTGTCTCCATATTTTAACAACCCTCATAAGGAATGGTAAATTCGTGTGTTTAATAATTTTTTCACCAAAAACTTTCG
 1202                                           1242           1258
     1208
```

FIG. 1b-6

```
                                                                                    Rsa I
                                                                                    Csp6 I
                                                                                  Mae II
                                                                                 SnaB I
          Aci I                                                                  BsaA I
 Mse I   Fau I                  Xcm I   Ssp I      Alu I
 |       ||                     |       |          |     || |
TCTTAATAAAACTTACCCGCCATACCACAGATGTTCCAGATAAATATTGGAAGCTATATACGTACTTTGTTTCAAAATGG  1520
AGAATTATTTTGAATGGGCGGTATGGTGTCTACAAGGTCTATTTATAACCTTCGATATATGCATGAAACAAAGTTTTACC
 |   .   ||  .     .      |  .   |    .    |     || |     .       .
 1443    1456               1476    1483       1492  1499
          1457                                       1499
                                                      1500
                                                        1502
                                                        1502

                                                                               Rsa I
                                                                               Csp6 I
   Taq I       Hinc II                        Tth111 II                    Mse I
   |           |                              |                            |   |
GTCAATCGAGAATATCGTCAACTGTTTACTAAAAATCAGTTTCATCAAGCAATGAAACACGCCAAAGTAAACAATTTAAG  1600
CAGTTAGCTCTTATAGCAGTTGACAAATGATTTTTAGTCAAAGTAGTTCGTTACTTTGTGCGGTTTCATTTGTTAAATTC
   |   .       |  .    .         .        |   .      .         .       |   |
   1526        1537                       1566                         1596
                                                                           1600
                                                                           1600

                                                                 Xmn I
  Mae III                    Mse I              Mse I   Mnl I        Ple I
                                                                     Hinf I
  |                          |                  |       |  |         |
TACCGTTACTTATGAGCAAGTATTGTCTATTTTTAATAGTTATCTATTATTTAACGGGAGGAAATAATTCTATGAGTCGC  1680
ATGGCAATGAATACTCGTTCATAACAGATAAAAATTATCAATAGATAATAAATTGCCCTCCTTTATTAAGATACTCAGCG
  |  .      .        .   |        .        .|       | .|     .     |       .
  1605                   1633                1651   1658          1674
                                                       1661          1674
```

FIG. 1b-8

```
        Taq I
     Tfi I
     Hinf I           Mnl I                                    BceF I  Esp3 I
                                                                       BsmA I
AGAAATGGGACGAATCGAGAAAACCCTCTTTACGCTGGATTACATATCTAATAAAGCCGTAAGGAGACGGGTTCAAAAAG  1920
TCTTTACCCTGCTTAGCTCTTTTGGGAGAAATGCGACCTAATGTATAGATTATTTCGGCATTCCTCTGCCCAAGTTTTTC
     1852             1865                                     1896    1904
     1852                                                              1904
        1855

                      Ppu10 I                                                 HgiA I
  Mse I               Nsi I    Bfa I                                  Apo I   Bsp1286 I
Dra I           BspW I       Alu I                             Mae II      Mae II
GTTTAAATAAAGGAGAAGCAATCAATGCATTAGCTAGAACTATATTTTTTGGACAACGTGGAGAATTTAGAGAACGTGCT  2000
CAAATTTATTTCCTCTTCGTTAGTTACGTAATCGATCTTGATATAAAAAACCTGTTGCACCTCTTAAATCTCTTGCACGA
1922            1938         1952                              1976        1994
 1923                 1945     1954                                  1983     1996
                      1945                                                    1996

                       HgiA I
                       Bsp1286 I
                       ApaL I
        Mae III     Bfa I
     Bsr I       Alu I                      Mse I
CTCCAAGACCAGTTACAAAGAGCTAGTGCACTAAACATAATTATTAACGCTATAAGTGTGTGGAACACTGTATATATGGA  2080
GAGGTTCTGGTCAATGTTTCTCGATCACGTGATTTGTATTAATAATTGCGATATTCACACACCTTGTGACATATATACCT
     2009        2021                       2044
        2012        2023
                       2026
                       2026
                       2026
```

FIG. 1b-10

```
                                                                              Rsa I
                                                                               Csp6 I
                                                                              Nla IV
                                                                              Kpn I
                                                                              Ban I
                                               Dde I                          Acc65 I
  BceF I       Mse I     BceF I               Bsl I                         Aci I
  |            |         |                    ||                            | ||
GAGCCGTTTTATTCTTAATATAACGGCTCTTTTTATAGAAAAAATCCTTAGCGTGGTTTTTTTCCGAAATGCTGGCGGTA  2320
CTCGGCAAAATAAGAATTATATTGCCGAGAAAAATATCTTTTTTAGGAATCGCACCAAAAAAAGGCTTTACGACCGCCAT
  |      .     |    .    |     .         .    || .          .         .     | || .
  2243         2255      2263                 2286                          2315
                                               2287                           2317
                                                                              2317
                                                                              2317
                                                                              2317
                                                                               2318
                                                                               2318

                                                             Mme I
                                                           Sau3A I
                                                           Mbo I
                        Sau3A I                            Dpn II
                        Mbo I                              Dpn I
                        Dpn II               Tfi I         Alw I
                        Dpn I                Hinf I       BstY I                Bfa I
                        |                    |            || |                  |
CCCCAAGAATTAGAAATGAGTAGATCAAATTATTCACGAATAGAATCAGGAAAATCAGATCCAACCATAAAAACACTAGA  2400
GGGGTTCTTAATCTTTACTCATCTAGTTTAATAAGTGCTTATCTTAGTCCTTTTAGTCTAGGTTGGTATTTTTGTGATCT
         .         .    |     .         .    |     .      || |          .       | .
                        2343                 2363         2377                  2396
                        2343                 2363          2378
                        2343                               2378
                        2343                               2378
                                                           2378
                                                           2378
                                                             2380
```

FIG. 1b-12

```
      Mse I
     Hpa I
     Hinc II          Bfa I      Mse I                                  Tfi I
     ||               |          |                                      Hinf I
                                                                        |
ACAAATTGCAAAGTTAACTAACTCAACGCTAGTAGTGGATTTAATCCCAAATGAGCCAACAGAACCAGAGCCAGAAACAG  2480
TGTTTAACGTTTCAATTGATTGAGTTGCGATCATCACCTAAATTAGGGTTTACTCGGTTGTCTTGGTCTCGGTCTTTGTC
     .  ||      .         |.         .|         .         .         .         |
     2413                 2429       2441                                   2480
     2413                                                                   2480
      2414

                                Mbo II
     Mae III                 Mbo II                                      Bcg I
     |                       |  |                                        |
AATCAGAACAAGTAACATTGGATTTAGAAATGGAAGAAGAAAAAAGCAATGACTTCGTGTGAATAATGCACGAAATCGTT  2560
TTAGTCTTGTTCATTGTAACCTAAATCTTTACCTTCTTCTTTTTTCGTTACTGAAGCACACTTATTACGTGCTTTAGCAA
     . |        .         .  |  |  .         .         .         .|        .
     2492                    2513                                 2551
                                2516

                 Bst1107 I
     Mse I       Acc I
     Dra I  Aci I    Bfa I                                               Nla III
     ||     |   |    |                                                   |
GCTTATTTTTTTTTAAAAGCGGTATACTAGATATAACGAAACAACGAACTGAATAGAAACGAAAAAAGAGCCATGACACA  2640
CGAATAAAAAAAAATTTTCGCCATATGATCTATATTGCTTTGTTGCTTGACTTATCTTTGCTTTTTTCTCGGTACTGTGT
     . ||     |.  |    |  .         .         .         .         .|       .
     2572     2579     2587                                          2632
      2573        2582
                  2582
```

FIG. 1b-13

```
                    Mae II
                    Psp1406 I
               Bfa I     Mse I                                  Dde I
               |    ||   |                                        |
GAAAATTAGCAAATATCTATACACTAGAAACGTTTAAGAAAGAGTTAGAAAAGAGAAATATCTACTTAGAAACAAAATCA  3040
CTTTTAATCGTTTATAGATATGTGATCTTTGCAAATTCTTTCTCAATCTTTTCTCTTTATAGATGAATCTTTGTTTTAGT
        .        .     |    ||   |      .        .        .   |    .        .
                      2984       2994                            3025
                           2989
                            2990
                  Mnl I
          Mbo II      Mbo II            Mse I                   Taq I
          |     |     |                 |                        |
GATAAGTATTTTTCTTCGGAGGGGGAAGATTATATATATAAGTTAATAGAAAATAACAAAATAATTTATTCGATTAGTGG  3120
CTATTCATAAAAAGAAGCCTCCCCCTTCTAATATATATATTCAATTATCTTTTATTGTTTTATTAAATAAGCTAATCACC
        . |     |.    |    .        .   |     .        .         |          .
          3053        3065              3083                     3110
                3059
                                            Ssp I
                                       Nla III
                                       NspC I
                                       Nsp7524 I
                                       Nsp I
                                       ||    |
AAAAAAATTGACTTATAAAGGAAAAAAATCTTTTTCAAAACATGCAATATTGAAACAGTTGAATGAAAAAGCAAACCAAG  3200
TTTTTTTAACTGAATATTTCCTTTTTTTAGAAAAAGTTTTGTACGTTATAACTTTGTCAACTTACTTTTTCGTTTGGTTC
        .        .        .            ||    |  .        .        .        .
                                       3160
                                       3160
                                       3160
                                        3161
                                             3166
```

FIG. 1b-15

```
    Mse I                                                    Alu I
Pac I                                                        Pvu II
Mse I                                                        NspB II
|    |                                                       ||
TTAATTAAACAACCTATTTTATAGGATTTATAGGAAAGGAGAACAGCTGAATGAATATCCCTTTTGTTGTAGAAACTGTG  3280
AATTAATTTGTTGGATAAAATATCCTAAATATCCTTTCCTCTTGTCGACTTACTTATAGGGAAAACAACATCTTTGACAC
|    |     .         .         .         .         ||    .         .         .         .
3201                                                 3244
3201                                                 3244
    3205                                              3245

                                                                          ScrF I
                                                                          EcoR II
      BceF I         Rsa I  Dra I                                         Dsa V
  Nla III            Csp6 I  Mse I                                        BstN I
 BspH I          Mse I   Apo I             Apo I                          BstK I
 ||    |         |    |    |  ||           |                              |
CTTCATGACGGCTTGTTAAAGTACAAATTTAAAAATAGTAAAATTCGCTCAATCACTACCAAGCCAGGTAAAAGCAAAGG  3360
GAAGTACTGCCGAACAATTTCATGTTTAAATTTTTATCATTTTAAGCGAGTTAGTGATGGTTCGGTCCATTTTCGTTTCC
 ||    | .       |   .|    |  ||.         .|         .         .         |  .         .
 3283            3296      3305            3321                           3344
  3284               3301    3309                                         3344
      3288           3301   3308                                          3344
                                                                          3344
                                                                          3344
```

FIG. 1b-16

```
                                   Nla III  Mcr I                                      Xmn I
                                  BspW I   BsiE I                                  Mnl I  Tfi I
BspW I                         Tth111 II  Aci I                                 BsaJ I  Hinf I
|                               |  ||       ||                                    | |  |    |
GGCTATTTTTGCGTATCGCTCAAAATCAAGCATGATTGGCGGTCGTGGTGTTGTTCTGACTTCCGAGGAAGCGATTCAAG  3440
CCGATAAAAACGCATAGCGAGTTTTAGTTCGTACTAACCGCCAGCACCACAACAAGACTGAAGGCTCCTTCGCTAAGTTC
|       .       .       |  ||       ||      .       .  | |  | .  |     .
3362                    3387        3399                3423      3433
                           3390      3400                 3425    3433
                            3391     3400                    3428
                             Mae II
                            Psp1406 I        Mae II
                             ||               |
AAAATCAAGATACATTTACACATTGGACACCCAACGTTTATCGTTATGGAACGTATGCAGACGAAAACCGTTCATACACG  3520
TTTTAGTTCTATGTAAATGTGTAACCTGTGGGTTGCAAATAGCAATACCTTGCATACGTCTGCTTTTGGCAAGTATGTGC
        .       .       .    ||     .       .|      .       .       .
                             3473            3491
                              3474
                       Mse I                                      BceF I
                        |                                          |
AAAGGACATTCTGAAAACAATTTAAGACAAATCAATACCTTCTTTATTGATTTTGATATTCACACGGCAAAAGAAACTAT  3600
TTTCCTGTAAGACTTTTGTTAAATTCTGTTTAGTTATGGAAGAAATAACTAAAACTATAAGTGTGCCGTTTTCTTTGATA
        .       .|      .       .       .       .  |    .       .
                 3542                              3584
                 Mse I Aci I                                            Tth111 II
                   |    |                                                 |
TTCAGCAAGCGATATTTTAACAACCGCTATTGATTTAGGTTTTATGCCTACTATGATTATCAAATCTGATAAAGGTTATC  3680
AAGTCGTTCGCTATAAAATTGTTGGCGATAACTAAATCCAAAATACGGATGATACTAATAGTTTAGACTATTTCCAATAG
        .          |  . |   .       .       .       .       .       |
                   3617 3624                                           3680
                                           Mse I
                                           Dra I
```

FIG. 1b-17

```
                                                  Swa I            Fnu4H I
                  Bsr I     Mae III            Apo I               Bbv I
                  |         |                  | |||               |
AAGCATATTTTGTTTTAGAAACGCCAGTCTATGTGACTTCAAAATCAGAATTTAAATCTGTCAAAGCAGCCAAAATAATT  3760
TTCGTATAAAACAAAATCTTTGCGGTCAGATACACTGAAGTTTTAGTCTTAAATTTAGACAGTTTCGTCGGTTTTATTAA
          .         .         .         .         .         .         .         .
                  3704      3713               3728                3746
                                                 3730              3746
                                                  3731
                                                   3732
                                                 Mae II
                                             Sau3A I
                                             Mbo I
                                             Dpn II
                                             Dpn I
       Ssp I                     Bsr I           Afl III
       |                         |     |         |
TCGCAAAATATCCGAGAATATTTTGGAAAGTCTTTGCCAGTTGATCTAACGTGTAATCATTTTGGTATTGCTCGCATACC  3840
AGCGTTTTATAGGCTCTTATAAAACCTTTCAGAAACGGTCAACTAGATTGCACATTAGTAAAACCATAACGAGCGTATGG
          .         .         .         .         .         .         .         .
       3777                      3797  3803      3809
                                       3803
                                       3803
                                       3803
                                                 3809
                 Sau3A I
                 Mbo I
                 Dpn II
                 Dpn I                                                    Tth111 II
       Apo I     Alw I                                                 Tth111 II
       |         |                                                     |   |
AAGAACGGACAATGTAGAATTTTTTGATCCTAATTACCGTTATTCTTTCAAAGAATGGCAAGATTGGTCTTTCAAACAAA  3920
TTCTTGCCTGTTACATCTTAAAAAACTAGGATTAATGGCAATAAGAAAGTTTCTTACCGTTCTAACCAGAAAGTTTGTTT
          .         .         .         .         .         .         .         .
       3857      3866                                                  3913
                 3866                                                      3917
                 3866
                 3866
                 3866
```

FIG. 1b-18

```
                                                                    ScrF I
                                                                    EcoR II
                                                                    Dsa V
                                        Rsa I                       BstN I
                                     Aci I                          BstK I
                                 Mse I  Csp6 I                     BsaJ I
CAGATAATAAGGGCTTTACTCGTTCAAGTCTAACGGTTTTAAGCGGTACAGAAGGCAAAAAACAAGTAGATGAACCCTGG  4000
GTCTATTATTCCCGAAATGAGCAAGTTCAGATTGCCAAAATTCGCCATGTCTTCCGTTTTTTGTTCATCTACTTGGGACC
                                 3959  3966                        3995
                                    3963                            3996
                                       3966                         3996
                                                                    3996
                                                                    3996
                                                                    3996

                                                              Nla III
Mse I             Apo I              Mse I             Mae II      Mnl I
TTTAATCTCTTATTGCACGAAACGAAATTTTCAGGAGAAAAGGGTTTAATAGGGCGTAATAACGTCATGTTTACCCTCTC  4080
AAATTAGAGAATAACGTGCTTTGCTTTAAAAGTCCTCTTTTCCCAAATTATCCCGCATTATTGCAGTACAAATGGGAGAG
4002              4025               4046              4062        4075
                                                          4066
                                                                 Sau3A I
                                                          Cla I  Mbo I
                         Mae II                    Mse I  Taq I  Dpn II
                     Taq I             Tth111 II          BspD I Dpn I
TTTAGCCTACTTTAGTTCAGGCTATTCAATCGAAACGTGCGAATATAATATGTTTGAGTTTAATAATCGATTAGATCAAC  4160
AAATCGGATGAAATCAAGTCCGATAAGTTAGCTTTGCACGCTTATATTATACAAACTCAAATTATTAGCTAATCTAGTTG
                     4110              4131               4146   4154
                         4115                      4140    4147  4154
                                                          4146   4154
                                                                 4154
```

FIG. 1b-19

```
     Mbo II
 Dde I
 |   |
CCTTAGAAGAAAAAGAAGTAATCAAAATTGTTAGAAGTGCCTATTCAGAAAACTATCAAGGGGCTAATAGGGAATACATT  4240
GGAATCTTCTTTTTCTTCATTAGTTTTAACAATCTTCACGGATAAGTCTTTTGATAGTTCCCCGATTATCCCTTATGTAA
 |   |   .         .         .         .         .         .         .         .
4162
     4166

                                                                              Apo I
                                                                            Mse I
             Alu I                   Bsr I                                 Dra I
            Hind III             Mse I                                     || |
             ||                   |   |                                    || |
ACCATTCTTTGCAAAGCTTGGGTATCAAGTGATTTAACCAGTAAAGATTTATTTGTCCGTCAAGGGTGGTTTAAATTCAA  4320
TGGTAAGAAACGTTTCGAACCCATAGTTCACTAAATTGGTCATTTCTAAATAAACAGGCAGTTCCCACCAAATTTAAGTT
         .   ||    .         .    |   | .         .         .        || |     .
            4254                 4274                                4310
             4255                    4278                             4311
                                                                        4313

                Mae II
                Afl III
            Hinc II                                  Mse I
          Mae II                               Mbo II                 BspW I
          | |  |                                |    |                 |
GAAAAAAAGAAGCGAACGTCAACGTGTTCATTTGTCAGAATGGAAAGAAGATTTAATGGCTTATATTAGCGAAAAAAGCG  4400
CTTTTTTTCTTCGCTTGCAGTTGCACAAGTAAACAGTCTTACCTTTCTTCTAAATTACCGAATATAATCGCTTTTTTCGC
         .  | | . |       .         .         | .  |         .        |.      .
          4336                                 4367                   4389
            4338                                    4373
                4342
                4342
```

FIG. 1b-20

```
Bst1107 I                                                   Bsm I
Acc I              Mae III                              Bfa I
|                  |                                    |   |
ATGTATACAAGCCTTATTTAGTGACGACCAAAAAAGAGATTAGAGAAGTGCTAGGCATTCCTGAACGGACATTAGATAAA  4480
TACATATGTTCGGAATAAATCACTGCTGGTTTTTTCTCTAATCTCTTCACGATCCGTAAGGACTTGCCTGTAATCTATTT
|         .        .|         .         .         .|   |    .         .         .
4403               4421                             4451
4403                                                    4455
                                                   ScrF I
                                                   EcoR II
                                                   Dsa V
      Rsa I       Tfi I                            BstN I
      Csp6 I      Hinf I                      Mse I    Mbo II
Eco57 I  Eco57 I        Apo I      Mse I           BstK I          Bsm I       Bfa I
|     |  |          |       |         |        |    |   |          |           |
TTGCTGAAGGTACTGAAGGCGAATCAGGAAATTTTCTTTAAGATTAAACCAGGAAGAAATGGTGGCATTCAACTTGCTAG  4560
AACGACTTCCATGACTTCCGCTTAGTCCTTTAAAAGAAATTCTAATTTGGTCCTTCTTTACCACCGTAAGTTGAACGATC
|     |  |         .|       |.        | .      |    |.  |     .    |    .      | .
4484     4493               4509      4518          4529           4545        4557
      4490        4501                         4524     4533
      4490        4501                              4529
                                                    4529
                                                    4529
                                                    4529
```

FIG. 1b-21

```
                          Sau3A I
                          Mbo I
                          Dpn II
                          Dpn I
                        Taq I
                       Cla I                                                               HinP I
                       Cla I                                                               Hha I
 Mse I                 BspD I  Mse I          Mbo II        Alu I         Hae II    Apo I
 |                     || |    |              |             |             ||        |
TGTTAAATCATTGTTGCTATCGATCATTAAAGTAAAAAAAGAAGAAAAAGAAAGCTATATAAAGGCGCTGACAAATTCTT  4640
ACAATTTAGTAACAACGATAGCTAGTAATTTCATTTTTTTCTTCTTTTTCTTTCGATATATTTCCGCGACTGTTTAAGAA
 |    .                || |    | .           .|        .    |        .    ||    .   |     .
 4563                  4579    4587           4601          4613          4624      4633
                       4579                                                  4625
                        4580                                                 4625
                          4582
                          4582
                          4582
                          4582
                                    Mse I      Bfa I
                                   Dra I      Nhe I
  Dde I                      BsmA I          Alu I           Bsl I                  Taq I
  |                          |    ||          |||             |                     |
TTGACTTAGAGCATACATTCATTCAAGAGACTTTAAACAAGCTAGCAGAACGCCCTAAAACGGACACACAACTCGATTTG  4720
AACTGAATCTCGTATGTAAGTAAGTTCTCTGAAATTTGTTCGATCGTCTTGCGGGATTTTGCCTGTGTGTTGAGCTAAAC
  |    .          .          |  . ||          |||       .     |        .         .  |      .
  4645                       4667             4680            4693                  4713
                                  4672         4681
                                   4673         4682
```

FIG. 1b-22

Tth111 II
Mae II
Afl III
BsaA I
Aci I
Fau I
Alu I

TTTAGCTATGATACAGGCTGAAAATAAAACCCGCACTATGCCATTACATTTATATCTATGATACGTGTTTGTTTTTTCTT 4800
AAATCGATACTATGTCCGACTTTTATTTTGGGCGTGATACGGTAATGTAAATATAGATACTATGCACAAACAAAAAAGAA 4724
4750
4751
4782
4783
4783
4786

Mse I
Ase I
Pac I
Mse I

TGCTGTTTAGCGAATGATTAGCAGAAATATACAGAGTAAGATTTTAATTAATTATTAGGGGGAGAAGGAGAGAGTAGCCC 4880
ACGACAAATCGCTTACTAATCGTCTTTATATGTCTCATTCTAAAATTAATTAATAATCCCCCTCTTCCTCTCTCATCGGG 4844
4844
4847
4848

Mnl I
Taq I
Mnl I
Mae II
BspW I

GAAAACTTTTAGTTGGCTTGGACTGAACGAAGTGAGGGAAAGGCTACTAAAACGTCGAGGGGCAGTGAGAGCGAAGCGAA 4960
CTTTTGAAAATCAACCGAACCTGACTTGCTTCACTCCCTTTCCGATGATTTTGCAGCTCCCCGTCACTCTCGCTTCGCTT 4914
4932
4935
4937
4942

FIG. 1b-23

```
 Mse I                                     Bst1107 I                                  Fnu4H I
                                           Acc I                                      Bbv I
CACTTGATTTTTTAATTTTCTATCTTTTATAGGTCATTAGAGTATACTTATTTGTCCTATAAACTATTTAGCAGCATAAT 5040
GTGAACTAAAAAATTAAAAGATAGAAAATATCCAGTAATCTCATATGAATAAACAGGATATTTGATAAATCGTCGTATTA
 4972                                      5002                                   5031

                                           Mnl I
            Mse I                  Mnl I                  Ssp I  Mbo II          Nla III
AGATTTATTGAATAGGTCATTTAAGTTGAGCATATTAGAGGAGGAAAATCTTGGAGAAATATTTGAAGAACCCGATTACA 5120
TCTAAATAACTTATCCAGTAAATTCAACTCGTATAATCTCCTCCTTTTAGAACCTCTTTATAAACTTCTTGGGCTAATGT
            5061                   5078                   5098   5105            5119
                                      5081

               Mae II
              BsaA I
            Mae III       Mse I          Apo I
TGGATTGGATTAGTTCTTGTGGTTACGTGGTTTTTAACTAAAAGTAGTGAATTTTTGATTTTTGGTGTGTGTGTCTTGTT 5200
ACCTAACCTAATCAAGAACACCAATGCACCAAAAATTGATTTTCATCACTTAAAAACTAAAAACCACACACACAGAACAA
            5142          5154           5169
              5144
               5145

 Bfa I         Mse I
GTTAGTATTTGCTAGTCAAAGTGATTAAATA 5231
CAATCATAAACGATCAGTTTCACTAATTTAT
 5212          5225
```

FIG. 1b-24

| | |
|---|---|
| P14 ANTISENSE: | GAAGATCTCTAGCTTTGAGCTGTAATAGA |
| P14 SENSE: | CGGAATTCAGTTGAACTACTTTTTTTAGTTTTA |
| P7 ANTISENSE: | GAAGATCTGTAATGTTTCGCAACTCTACTAT |
| P7 SENSE: | CGGAATTCAGGACTAATTGATGAAACTTTTCT |
| P1 ANTISENSE: | GAAGATCTGATACTTGTATTATAACATATCTAC |
| P1 SENSE: | CGGAATTCGATTAAGTCATCTTACCTCTTT |

FIG. 1d

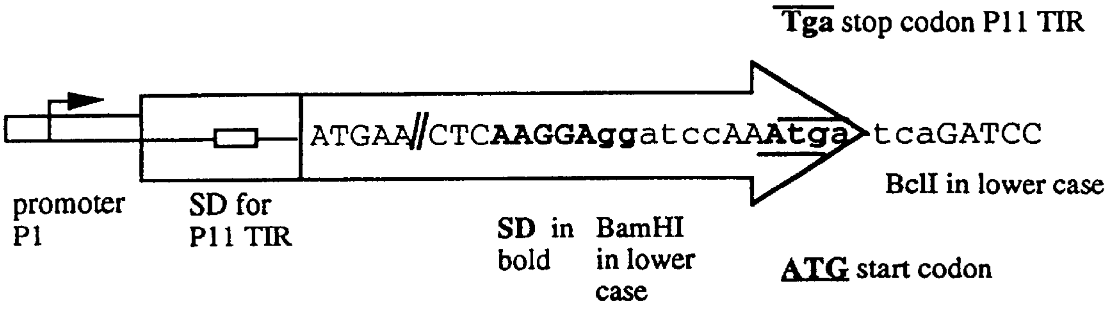

BamHI unique for cloning - enables target genes to be cloned with own ATG providing that the overlapping ATG / TGA start and stop codons are maintained to ensure translational coupling.

FIG. 2a

```
Start of P1 fragment
|
|  Taq I
EcoR I                                                          Mse I
Apo I  Mse I       Mnl I                                        Ase I
| |    |           |                                            ||
GAATTCGATTAAGTCATCTTACCTCTTTTATTAGTTTTTTCTTATAATCTAATGATAACATTTTTATAATTAATCTATAA  80
CTTAAGCTAATTCAGTAGAATGGAGAAAATAATCAAAAAAGAATATTAGATTACTATTGTAAAAATATTAATTAGATATT
| |    |.         .|        .        .        .        .        ||        .
1      9           22                                           69
1                                                                70
   5
                                                   End of P1 fragment  Mse I
                                                                |     Dra I
                                                                 Sau3A I
                                                                 Mbo I
                                                                 Dpn II
                              Apo I                              Dpn I
                         Tfi I                                  BstY I
             Mnl I       Hinf I                                 Bgl II
             |           |    |                                 ||   ||
ACCATATCCCTCTTTGGAATCAAAATTTATTATCTACTCCTTTGTAGATATGTTATAATACAAGTATCagatctTTAAAA  160
TGGTATAGGGAGAAACCTTAGTTTTAAATAATAGATGAGGAAACATCTATACAATATTATGTTCATAGtctagaAATTTT
             |.          | .  |        .        .        .        .   ||   ||    .
             89          97                                     149
                         97                                     149
                              103                                150
                                                                 150
                                                                 150
                                                                 150
                                                                    154
                                                                     155
```

FIG. 2b-1

```
                                                                        Mae II
    Sau3A I
    Mbo I
    Dpn II
       Taq I
  ScrF I
  EcoR II
  Dsa V   Dpn I
  BstN I
Bcg I  BstK I                                   513
 |     | | |                                513  513
 |     | | |                           511  513
 |     506                              |    |
 |     506                              |    |
 |     506                              |    |
 |     506                              |    |
 |     506                              |    |
 495                                     550        560
AGCGAGAGAAGGCGAAAACATTGCCTGGTGATCATTCATAAAGCAAATGCCTTTTCTAAAGATAAACGTATAAAAG
TCGCTCTCTTCCGCTTTTGTAACGGACCACTAGTAAGTATTTCGTTTACGGAAAAGATTTCTATTTGCATATTTTC
```

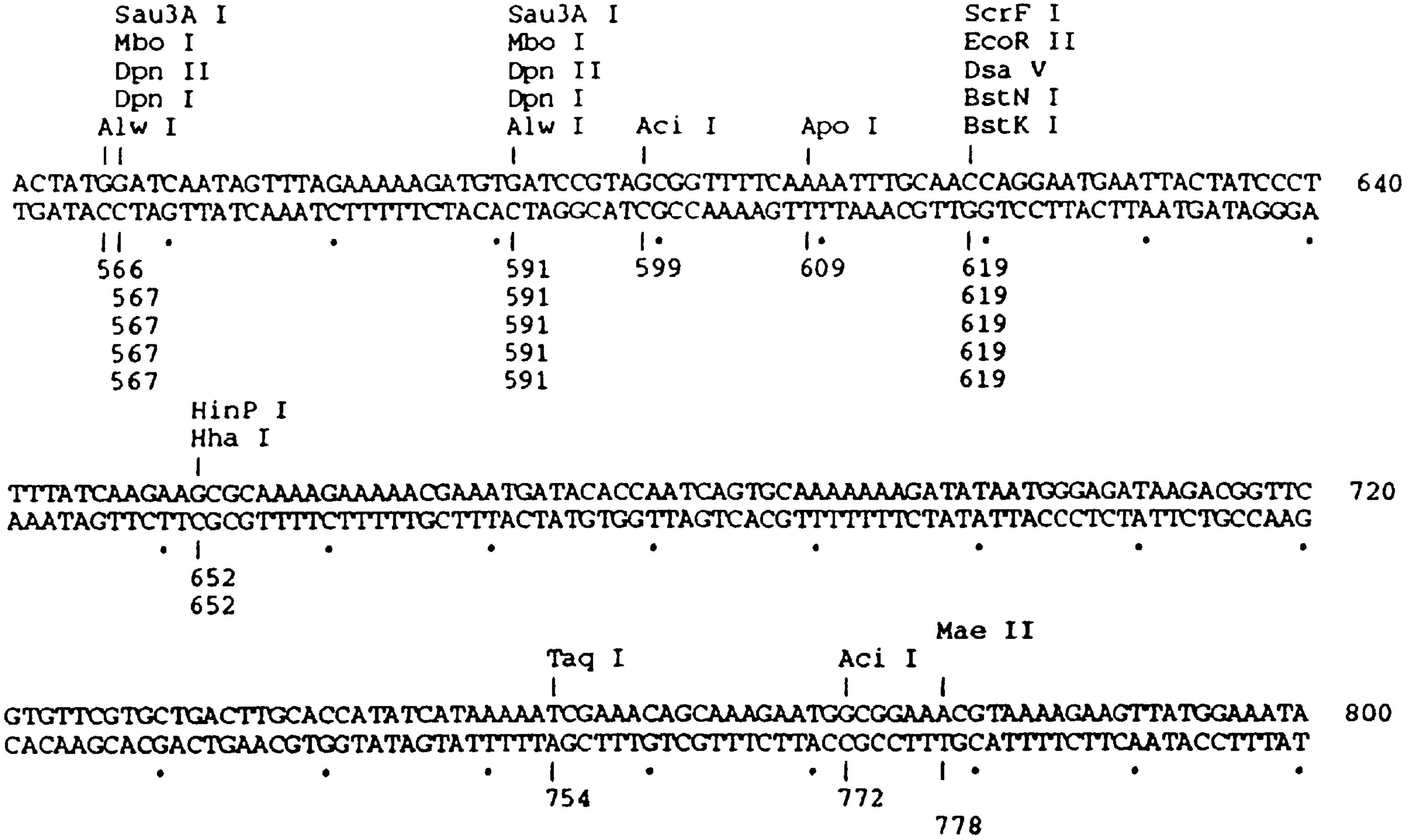

FIG. 2b-5

```
                                                              ScrF I
                   Sau3A I                                    EcoR II
                   Mbo I                                      Dsa V
                   Dpn II                                     BstN I
                   Dpn I                                      BstK I
                   Alw I        Aci I        Apo I
                    |            |            |                |
   566              591          599          609             619
   567              591                                       619
   567              591                                       619
   567              591                                       619
   567              591                                       619
ACTATGGATCAATAGTTTAGAAAAAGATGTGATCCGTAGGCGTTTCAAATTTGCACCAGGAATGAATTACTATCCCT    640
TGATACCTAGTTATCAAATCTTTTTCTACACTAGGCATCGCCAAAAGTTTTAAACGTGGTCCTTACTTAATGATAGGGA
                  |
                  HinP I
                  Hha I

                                                                            720
TTTATCAAGAAGCGCAAAAGAAAAACGAATGATACACCAATCAGTGCAAAAAAGATATAATGGAGATAAGACGGTTC
AAATAGTTCTTCGCGTTTTCTTTTTGCTTACTATGTGGTTAGTCACGTTTTTTCTATATTACCCTCTATTCTGCCAAG
  |                                                                   |
  652                                                                  Mae II
  652                                      Taq I    Aci I
                                             |        |
                                            754      772    778
                                                                            800
GTGTTCGTCTGCTGACTTGCACCATATATCATAAAAATCGAAACAGCAAAGAATGGCGGAAACGTAAAAGAAGTTATGGAAATA
CACAAGCACGACTGAACGTGGTATAGTATTTTTAGCTTTGTCGTTTCTTACCGCCTTTGCATTTTCTTCAATACCTTTAT
```

```
                       Mse I
 Mse I           Mae III   Hph I        Sfc I                  Mnl I
                                                            Tth111 II
AAAAATTAAAACTGAATACTCGTGTCACTTTAATTCACCAAGATATTCTACAGTTTCAATTCCCTAACAAACAGAGGTAT  1200
TTTTTAATTTTGACTTATGAGCACAGTGAAATTAAGTGGTTCTATAAGATGTCAAAGTTAAGGGATTGTTTGTCTCCATA
 1126            1144      1155         1168                1188
                      1150                                      1194

                                                              Hga I
                   Mse I         Mse I                       Nla III
AAAATTGTTGGGAGTATTCCTTACCATTTAAGCACACAAATTATTAAAAAAGTGGTTTTTGAAAGCCATGCGTCTGACAT  1280
TTTTAACAACCCTCATAAGGAATGGTAAATTCGTGTGTTTAATAATTTTTTCACCAAAAACTTTCGGTACGCAGACTGTA
                   1228          1244                        1267
                                                               1270

                                Sty I
                 Tfi I          BsaJ I
                 Hinf I       Rsa I
          Mbo II              Csp6 I        Hph I    Bfa I                BsmA I
CTATCTGATTGTTGAAGAAGGATTCTACAAGCGTACCTTGGATATTCACCGAACACTAGGGTTGCTCTTGCACACTCAAG  1360
GATAGACTAACAACTTCTTCCTAAGATGTTCGCATGGAACCTATAAGTGGCTTGTGATCCCAACGAGAACGTGTGAGTTC
          1294                1313          1326     1336                 1360
                 1301         1313
                 1301           1316
                                1316
```

FIG. 2b-7

```
                            Fnu4H I
                            Bbv I
                           Alu I       Xmn I
     Tfi I            Afl II           Bsm I
     Hinf I          BspW I        Aci I
    Taq I     Mun I   Mse I      NspB II        Fok I                           Mse I
    | |       |     |||   ||     | |  |         |                               |
TCTCGATTCAGCAATTGCTTAAGCTGCCAGCGGAATGCTTTCATCCTAAACCAAAAGTAAACAGTGTCTTAATAAAACTT  1440
AGAGCTAAGTCGTTAACGAATTCGACGGTCGCCTTACGAAAGTAGGATTTGGTTTTCATTTGTCACAGAATTATTTTGAA
    | |    •  |     |||•  ||     | |  |      •  |         •         •         |•         •
    1363      1372   1379        1388          1402                             1429
      1365          1377           1390
      1365           1378             1393
                         1382         1393
                          1383
                          1383

                                                 Rsa I
                                                 Csp6 I
                                               Mae II
  Aci I                                       SnaB I
 Fau I                Xcm I  Ssp I    Alu I   BsaA I                          Taq I
 ||                   |      |        |       || |                            |
ACCCGCCATACCACAGATGTTCCAGATAAATATTGGAAGCTATATACGTACTTTGTTTCAAAATGGGTCAATCGAGAATA  1520
TGGGCGGTATGGTGTCTACAAGGTCTATTTATAACCTTCGATATATGCATGAAACAAAGTTTTACCCAGTTAGCTCTTAT
 ||       •         • |      |•       | •     || | •         •         • |         •
 1442                 1462   1469     1478    1485                        1512
  1443                                        1485
                                               1486
                                                 1488
                                                 1488
```

FIG. 2b-8

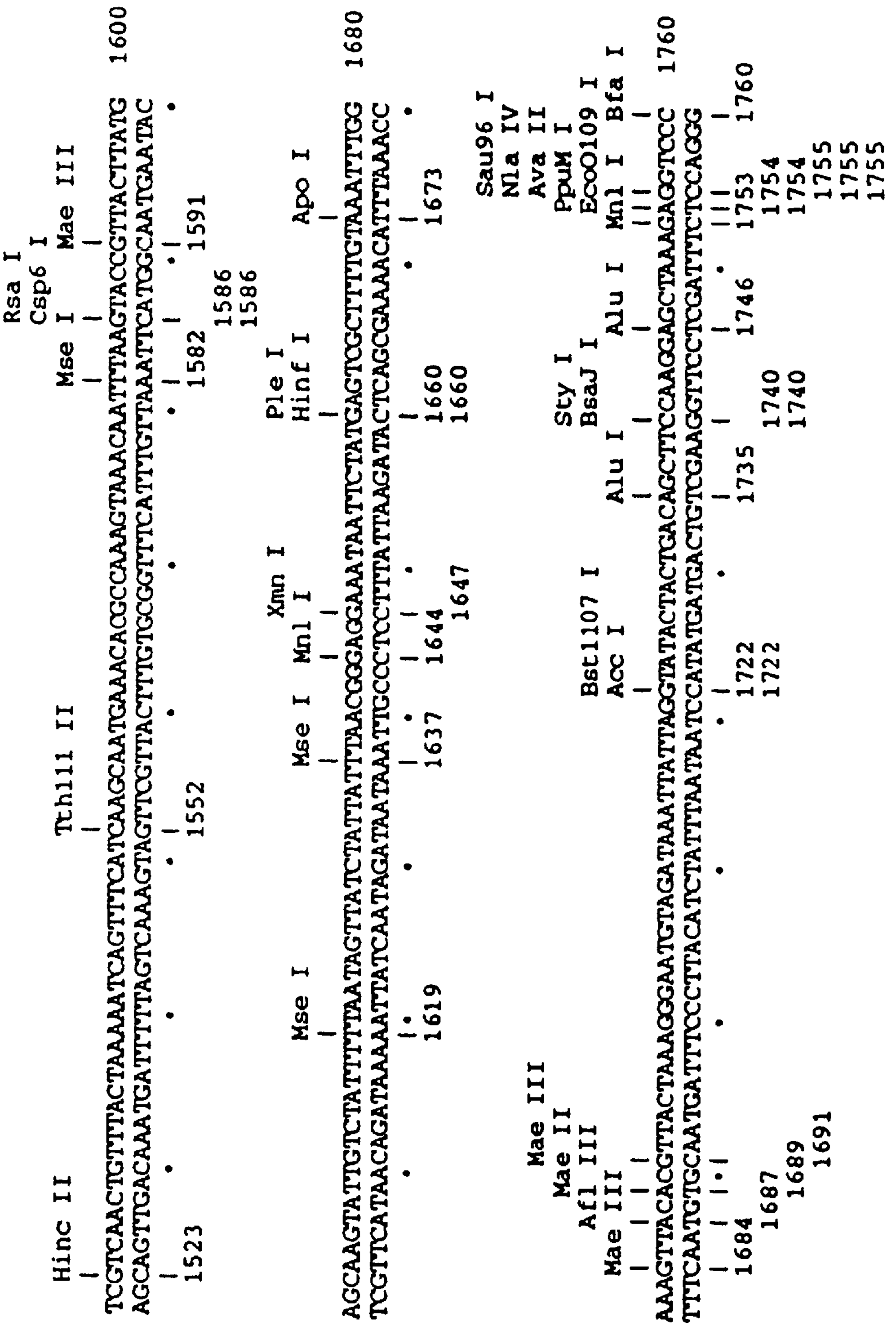

FIG. 2b-9

```
                                                                    Rsa I
                                                                    Csp6 I
                              Tth111 II                 Mse I       Mae III
Hinc II                       |                         |           |
TCGTCAACTGTTACTAAAATCAGTTTCATCATGCAAGCAATGAAACACGCCAAAGTAAACAATTAAGTACCGTTACTTATG  1600
AGCAGTTGACAAATGATTTTAGTCAAAGTAGTTCGTTACTTTGTGCGGTTTCATTTGTTAATTCATGGCAATGAATAC
|                                                       |           |
1523                                                   1582        1591
                                                       1586
                                                       1586

                                    Xmn I                    Ple I
                     Mse I          Mnl I                    Hinf I                    Apo I
                     |              | |                      | |                        |
AGCAAGTATTGTCTATTTCTATTTTAATAGTTATCTATTTAACGGGAGGAAATAATTCTATGAGTCGCTTTTGTAAATTTGG   1680
TCGTTCATAACAGATAAAAGATAAATTATCAATAGATAAATTGCCCTCCTTTATTAAGATACTCAGCGAAAACATTTAAACC
|                                   | |                      | |                       |
1619                               1637 1644                 1660 1660                 1673
                                        1647

                                                                              Sau96 I
                                                                              Nla IV
                                                                              Ava II
                                                              Sty I           PpuM I
              Mae II                                          BsaJ I          EcoO109 I
              Mae III             Bst1107 I                   |   Alu I   Mnl I   Bfa I
              Afl III             Acc I            Alu I      |   |       |       |
              | | |               | |              |          |   |       |       |
AAAGTTACACGTTACTAAAAGGAATGTAGATAAATTATTAGGTATACTGACAGCTTCCAAGGAGCTAAGAGTCCC          1760
TTTCAATGTGCAATGATTTCCCTTACATCTATTTAATAATCCATATGACTGTCGAAGGTTCCTCGATTCTCAGGG
| | |                             | |             |          |   |       |       |
1684                              1722             1735      1740 1746   1753    1760
1687                              1722                       1740       1754    1755
1689                                                                     1754    1755
1691                                                                             1755
```

```
                                 Sau3A I
                                 Mbo I
  HinP I                         Dpn II
  Hha I                          Dpn I
 Hae II                    Alu I   Nde I                                             Tfi I
 Eco47 III  Nla III          Alw I                                                   Hinf I
 ||         |            |   ||  |                                                   |
TAGCGCTCTTATCATGGGGAAGCTCGGATCATATGCAAGACAAAATAAACTCGCAACAGCACTTGGAGAAATGGGACGAA  1840
ATCGCGAGAATAGTACCCCTTCGAGCCTAGTATACGTTCTGTTTTATTTGAGCGTTGTCGTGAACCTCTTTACCCTGCTT
 ||      .  |        .|  ||  |         .        .        .        .          | .
 1762       1773         1786                                                1838
 1762                1781     1790                                           1838
  1763                    1787
  1763                    1787
                          1787
                          1787

                                                            Esp3 I            Mse I
Taq I     Mnl I                                    BceF I   BsmA I           Dra I
|         |                                        |        |                 ||
TCGAGAAAACCCTCTTTACGCTGGATTACATATCTAATAAAGCCGTAAGGAGACGGGTTCAAAAAGGTTTAAATAAAGGA  1920
AGCTCTTTTGGGAGAAATGCGACCTAATGTATAGATTATTTCGGCATTCCTCTGCCCAAGTTTTTCCAAATTTATTTCCT
|        .|         .         .         . |        |         .          ||.       .
1841      1851                            1882     1890                  1908
                                                   1890                   1909

          Ppu10 I                                                 HgiA I
          Nsi I    Bfa I                              Apo I       Bsp1286 I      Mae III
  BspW I          Alu I                    Mae II                Mae II        Bsr I
  |       |      | |                       |      |               | |          |  |
GAAGCAATCAATGCATTAGCTAGAACTATATTTTTTGGACAACGTGGAGAATTTAGAGAACGTGCTCTCCAAGACCAGTT  2000
CTTCGTTAGTTACGTAATCGATCTTGATATAAAAAACCTGTTGCACCTCTTAAATCTCTTGCACGAGAGGTTCTGGTCAA
  |      .|      | |         .         . |      |.              | |     .    |  | .
  1924           1938                    1962                   1980         1995
          1931     1940                         1969              1982          1998
          1931                                                    1982
```

FIG. 2b-10

```
        HgiA I
        Bsp1286 I
        ApaL I
     Bfa I
   Alu I                 Mse I                                     BceF I
                                                                          Mbo II
   | |  |                |                                         |      |
ACAAAGAGCTAGTGCACTAAACATAATTATTAACGCTATAAGTGTGTGGAACACTGTATATATGGAAAAAGCCGTAGAAG  2080
TGTTTCTCGATCACGTGATTTGTATTAATAATTGCGATATTCACACACCTTGTGACATATATACCTTTTTCGGCATCTTC
   | |• |       •        |         •         •         •        •|      |  •
   2007                  2030                                      2071
     2009                                                                 2077
        2012
        2012
        2012

                                                         BceF I
                                                        Hae III
                  Apo I                Mse I   Nde I   Gdi II
 Mse I      Mnl I            Mbo II            BstX I  Eae I     Fok I
 |          |    |           |         |       ||      |||       |
AATTAAAAGCAAGAGGAGAATTTAGAGAAGATTTAATGCCATATGCGTGGCCGTTAGGATGGGAACATATCAATTTTTCTT  2160
TTAATTTTCGTTCTCCTCTTAAATCTCTTCTAAATTACGGTATACGCACCGGCAATCCTACCCTTGTATAGTTAAAAGAA
 |     •    |    | •         |  •      |       ||      |||       | •         •        •
 2083       2093             2107              2119    2128      2137
                 2098                  2113     2120   2128
                                                        2129
                                                         2130

                                                           Mae II
                        Bsr I                     Mae II   SnaB I
      Apo I          Nla III          Apo I                BsaA I         BceF I
      |              |      |         |           |        ||             |
GGAGAATACAAATTTGAAGGATTACATGACACTGGGCAAATGAATTTACGTCCTTTACGTATAAAAGAGCCGTTTTATTC  2240
CCTCTTATGTTTAAACTTCCTAATGTACTGTGACCCGTTTACTTAAATGCAGGAAATGCATATTTTCTCGGCAAAATAAG
      |         •    |     •|        • |           | •      || •          |•        •
      2170           2185             2202                 2216           2229
                            2191                   2208    2216
                                                            2217
```

FIG. 2b-11

```
                                                          Rsa I
                                                          Csp6 I
                                                         Nla IV
                                                         Kpn I
                                                         Ban I
                         Dde I                           Acc65 I
Mse I    BceF I         Bsl I                          Aci I
|        |              ||                             | ||
TTAATATAACGGCTCTTTTTATAGAAAAAATCCTTAGCGTGGTTTTTTTCCGAAATGCTGGCGGTACCCCAAGAATTAGA  2320
AATTATATTGCCGAGAAAAATATCTTTTTTAGGAATCGCACCAAAAAAAGGCTTTACGACCGCCATGGGGTTCTTAATCT
|        |.          .          . ||         .          .         .| ||       .          .
2241     2249                     2272                             2301
                                   2273                              2303
                                                                     2303
                                                                      2304

                                            Mme I
                                          Sau3A I
                                          Mbo I
        Sau3A I                           Dpn II
        Mbo I                             Dpn I                                Mse I
        Dpn II               Tfi I        Alw I                               Hpa I
        Dpn I                Hinf I      BstY I            Bfa I              Hinc II
        |                    |           || |              |                  ||
AATGAGTAGATCAAATTATTCACGAATAGAATCAGGAAAATCAGATCCAACCATAAAAACACTAGAACAAATTGCAAAGT  2400
TTACTCATCTAGTTTAATAAGTGCTTATCTTAGTCCTTTTAGTCTAGGTTGGTATTTTTGTGATCTTGTTTAACGTTTCA
        |.          .        |.          .  || |       .          . |          .     ||
        2329                 2349        2363                        2382             2399
        2329                 2349         2364                                        2399
        2329                              2364                                         2400
        2329                              2364
                                          2364
                                          2364
                                            2366
```

FIG. 2b-12

```
                                                                 Tfi I
              Bfa I       Mse I                                  Hinf I      Mae III
              |           |                                      |           |
TAACTAACTCAACGCTAGTAGTGGATTTAATCCCAAATGAGCCAACAGAACCAGAGCCAGAAACAGAATCAGAACAAGTA  2480
ATTGATTGAGTTGCGATCATCACCTAAATTAGGGTTTACTCGGTTGTCTTGGTCTCGGTCTTTGTCTTAGTCTTGTTCAT
         .    |    .      | .        .         .         .        |   .       | .
              2415        2427                                   2466        2478
                                                                 2466

                    Mbo II
                 Mbo II                                                       Mse I
                                                                    Bcg I     Dra I
                 |  |                                               |         ||
ACATTGGATTTAGAAATGGAAGAAGAAAAAAGCAATGACTTCGTGTGAATAATGCACGAAATCGTTGCTTATTTTTTTTT  2560
TGTAACCTAAATCTTTACCTTCTTCTTTTTTCGTTACTGAAGCACACTTATTACGTGCTTTAGCAACGAATAAAAAAAAA
         .       |. |      .         .         .        |  .       .      ||.
                 2499                                   2537              2558
                    2502                                                   2559

      Bst1107 I
      Acc I
   Aci I   Bfa I                                                   Nla III       Tth111 II
   |  |    |                                                       |             |
AAAAGCGGTATACTAGATATAACGAAACAACGAACTGAATAGAAACGAAAAAAGAGCCATGACACATTTATAAAATGTTT  2640
TTTTCGCCATATGATCTATATTGCTTTGTTGCTTGACTTATCTTTGCTTTTTTCTCGGTACTGTGTAAATATTTTACAAA
   |  |.   |     .         .         .         .       |.       .    |   .
   2565    2573                                        2618          2636
      2568
      2568
```

FIG. 2b-13

```
                                                                        Mnl I
           Ppu10 I                                                 Mbo II
           Nsi I     Bcg I                                        Ear I
           |         |                                            ||   |
GACGACATTTTATAAATGCATAGCCCGATAAGATTGCCAAACCAACGCTTATCAGTTAGTCAGATGAACTCTTCCCTCGT  2720
CTGCTGTAAAATATTTACGTATCGGGCTATTCTAACGGTTTGGTTGCGAATAGTCAATCAGTCTACTTGAGAAGGGAGCA
         .  |   .    |    .         .         .         .         ||   |    .
           2656      2666                                         2709
           2656                                                    2710
                                                                       2715

           Mse I       Mbo II
       Pac I           Bbs I            Rsa I
       Mse I      Tth111 II             Csp6 I
       |   |      |    |                |
AAGAAGTTATTTAATTAACTTTGTTTGAAGACGGTATATAACCGTACTATCATTATATAGGGAAATCAGAGAGTTTTCAA  2800
TTCTTCAATAAATTAATTGAAACAAACTTCTGCCATATATTGGCATGATAGTAATATATCCCTTTAGTCTCTCAAAAGTT
      .|   |   .  |    |    .         .|        .         .         .         .
       2731       2742                  2764
       2731            2747             2764
           2735        2747

    Alu I      Mse I
  Dde I     Apo I       Mse I
  |  |      |   |       |
GTATCTAAGCTACTGAATTTAAGAATTGTTAAGCAATCAATCGGAAATCGTTTGATTGCTTTTTTTGTATTCATTTATAG  2880
CATAGATTCGATGACTTAAATTCTTAACAATTCGTTAGTTAGCCTTTAGCAAACTAACGAAAAAAACATAAGTAAATATC
  |  | .    |   |.      |.        .         .         .         .         .
  2805      2815        2829
     2808       2819
```

FIG. 2b-14

```
       Nla III
      BspH I
    Tfi I
    Hinf I
    |  ||
AAGGTGGAGTTTGTATGAATCATGATGAATGTAAAACTTATATAAAAAATAGTTTATTGGAGATAAGAAAATTAGCAAAT  2960
TTCCACCTCAAACATACTTAGTACTACTTACATTTTGAATATATTTTTTATCAAATAACCTCTATTCTTTTAATCGTTTA
      .     |  ||    .         .         .         .         .         .
            2897
            2897
               2900
                2901

      Mae II
     Psp1406 I
 Bfa I     Mse I                                       Dde I                       Mbo II
 |    ||   |                                           |                           |
ATCTATACACTAGAAACGTTTAAGAAAGAGTTAGAAAAGAGAAATATCTACTTAGAAACAAAATCAGATAAGTATTTTTC  3040
TAGATATGTGATCTTTGCAAATTCTTTCTCAATCTTTTCTCTTTATAGATGAATCTTTGTTTTAGTCTATTCATAAAAAG
 |    ||   |         .         .         .|        .         .         |.
 2970      2980                           3011                         3039
      2975
       2976

     Mbo II
Mnl I                   Mse I                      Taq I
|     |                 |                          |
TTCGGAGGGGGAAGATTATATATATAAGTTAATAGAAAATAACAAAATAATTTATTCGATTAGTGGAAAAAAATTGACTT  3120
AAGCCTCCCCCTTCTAATATATATATTCAATTATCTTTTATTGTTTTATTAAATAAGCTAATCACCTTTTTTTAACTGAA
|    .|        .        |.        .         .          |  .         .         .
3045                    3069                           3096
      3051
```

FIG. 2b-15

```
                           Ssp I
                      Nla III
                     NspC I                                                 Mse I
                     Nsp7524 I                                          Pac I
                     Nsp I                                              Mse I
                     ||    |                                            |   |
ATAAAGGAAAAAAATCTTTTTCAAAACATGCAATATTGAAACAGTTGAATGAAAAAGCAAACCAAGTTAATTAAACAACC  3200
TATTTCCTTTTTTTAGAAAAAGTTTTGTACGTTATAACTTTGTCAACTTACTTTTTCGTTTGGTTCAATTAATTTGTTGG
         .         .     || .  |    .         .         .         |  .|       .
                         3146                                       3187
                         3146                                       3187
                         3146                                           3191
                          3147
                               3152
                             Alu I                                     BceF I
                            Pvu II                                 Nla III
                            NspB II                               BspH I
                            ||                                    ||   |
TATTTTATAGGATTTATAGGAAAGGAGAAcagctgAATGAATATCCCTTTTGTTGTAGAAACTGTGCTTCATGACGGCTT  3280
ATAAAATATCCTAAATATCCTTTCCTCTTgtcgacTTACTTATAGGGAAAACAACATCTTTGACACGAAGTACTGCCGAA
         .         .        ||          .         .         .     ||   |     .
                            3230                                  3269
                            3230                                   3270
                             3231                                      3274
                                                 ScrF I
                                                 EcoR II
    Rsa I  Dra I                                 Dsa V
    Csp6 I  Mse I                                BstN I
Mse I   Apo I             Apo I                  BstK I                 BspW I
|    |   |  ||              |                      |                      |
GTTAAAGTACAAATTTAAAAATAGTAAAATTCGCTCAATCACTACCAAGCCAGGTAAAAGCAAAGGGGCTATTTTTGCGT  3360
CAATTTCATGTTTAAATTTTTATCATTTTAAGCGAGTTAGTGATGGTTCGGTCCATTTTCGTTTCCCCGATAAAAACGCA
|    |  .|  ||     .        |  .         .         |         .         | .       .
3282    3291                3307                   3330                  3348
    3287   3295                                    3330
    3287  3294                                     3330
                                                   3330
                                                   3330
```

FIG. 2b-16

```
             Nla III  Mcr I                                 Xmn I
            BspW I    BsiE I                             Mnl I   Tfi I
          Tth111 II  Aci I                             BsaJ I    Hinf I
          |  ||      ||                                |  |  |   |
ATCGCTCAAAATCAAGCATGATTGGCGGTCGTGGTGTTGTTCTGACTTCCGAGGAAGCGATTCAAGAAAATCAAGATACA  3440
TAGCGAGTTTTAGTTCGTACTAACCGCCAGCACCACAACAAGACTGAAGGCTCCTTCGCTAAGTTCTTTTAGTTCTATGT
       .  |  ||  .   ||    .         .         |.|   |   |.        .         .
          3373       3385                      3409      3419
             3376     3386                       3411    3419
              3377    3386                          3414
               Mae II
              Psp1406 I       Mae II
              ||              |
TTTACACATTGGACACCCAACGTTTATCGTTATGGAACGTATGCAGACGAAAACCGTTCATACACGAAAGGACATTCTGA  3520
AAATGTGTAACCTGTGGGTTGCAAATAGCAATACCTTGCATACGTCTGCTTTTGGCAAGTATGTGCTTTCCTGTAAGACT
         .    ||       .      | .         .         .         .         .
              3459            3477
               3460
       Mse I                                      BceF I
       |                                          |
AAACAATTTAAGACAAATCAATACCTTCTTTATTGATTTTGATATTCACACGGCAAAAGAAACTATTTCAGCAAGCGATA  3600
TTTGTTAAATTCTGTTTAGTTATGGAAGAAATAACTAAAACTATAAGTGTGCCGTTTTCTTTGATAAAGTCGTTCGCTAT
       | .         .         .         .          |        .         .         .
       3528                                       3570
```

FIG. 2b-17

```
Mse I  Aci I                                                                   Tth111 II
|      |                                                                       |
TTTTAACAACCGCTATTGATTTAGGTTTTATGCCTACTATGATTATCAAATCTGATAAAGGTTATCAAGCATATTTTGTT  3680
AAAATTGTTGGCGATAACTAAATCCAAAATACGGATGATACTAATAGTTTAGACTATTTCCAATAGTTCGTATAAAACAA
|      |                                                                       |
3603   3610                                                                    3666

                                                  Mse I
                                                 Dra I
                                                Swa I
       Bsr I        Mae III          Apo I              Fnu4H I
                                                        Bbv I
TTAGAAACGCCAGTCTATGTGACTTCAAAATCAGAATTTAAATCTGTCAAAGCAGCCAAAATAATTTCGCAAAATATCCG  3760
AATCTTTGCGGTCAGATACACTGAAGTTTTAGTCTTAAATTTAGACAGTTTCGTCGGTTTTATTAAAGCGTTTTATAGGC
       3690         3699             3714               3732
                                      3716              3732
                                       3717
                                        3718

                                            Mae II
                                       Sau3A I
                                       Mbo I
                                       Dpn II
                                       Dpn I
Ssp I                      Bsr I                 Afl III
AGAATATTTTGGAAAGTCTTTGCCAGTTGATCTAACGTGTAATCATTTTGGTATTGCTCGCATACCAAGAACGGACAATG  3840
TCTTATAAAACCTTTCAGAAACGGTCAACTAGATTGCACATTAGTAAAACCATAACGAGCGTATGGTTCTTGCCTGTTAC
3763                       3783                  3795
                                       3789
                                                 3795
```

FIG. 2b-18

```
                Sau3A I
                Mbo I
                Dpn II                                                           Tth111 II
    Apo I       Dpn I                                                        Tth111 II
    |           Alw I                                                        |   |
TAGAATTTTTTGATCCTAATTACCGTTATTCTTTCAAAGAATGGCAAGATTGGTCTTTCAAACAAACAGATAATAAGGGC  3920
ATCTTAAAAAACTAGGATTAATGGCAATAAGAAAGTTTCTTACCGTTCTAACCAGAAAGTTTGTTTGTCTATTATTCCCG
   |       .|       .         .         .         .         |.  |      .         .
   3843     3852                                              3899
            3852                                                 3903
            3852
            3852
            3852

                                                                       Mse I
                                                                 ScrF I
                                                                 EcoR II
                                                                 Dsa V
                                    Rsa I                        BstN I
                                Aci I                            BstK I
                             Mse I  Csp6 I                      BsaJ I
                             |   |  |                           ||     |
TTTACTCGTTCAAGTCTAACGGTTTTAAGCGGTACAGAAGGCAAAAAACAAGTAGATGAACCCTGGTTTAATCTCTTATT  4000
AAATGAGCAAGTTCAGATTGCCAAAATTCGCCATGTCTTCCGTTTTTTGTTCATCTACTTGGGACCAAATTAGAGAATAA
          .         .    |   |. |      .         .         .||     | .         .
                         3945  3952                         3981
                             3949                            3982
                                3952                         3982
                                                             3982
                                                             3982
                                                             3982
                                                                   3988

                                                     Nla III
          Apo I                 Mse I            Mae II          Mnl I
          |                     |                |   |           |
GCACGAAACGAAATTTTCAGGAGAAAAGGGTTTAATAGGGCGTAATAACGTCATGTTTACCCTCTCTTTAGCCTACTTTA  4080
CGTGCTTTGCTTTAAAAGTCCTCTTTTCCCAAATTATCCCGCATTATTGCAGTACAAATGGGAGAGAAATCGGATGAAAT
         .|         .         .|         .       | . |       .|         .         .
          4011                  4032             4048        4061
                                                     4052
```

FIG. 2b-19

```
                                                                  Sau3A I
                                                          Cla I   Mbo I
                 Mae II                            Mse I   Taq I  Dpn II        Mbo II
             Taq I                    Tth111 II            BspD I Dpn I    Dde I
             |    |                   |            |       ||     |        |   |
GTTCAGGCTATTCAATCGAAACGTGCGAATATAATATGTTTGAGTTTAATAATCGATTAGATCAACCCTTAGAAGAAAAA  4160
CAAGTCCGATAAGTTAGCTTTGCACGCTTATATTATACAAACTCAAATTATTAGCTAATCTAGTTGGGAATCTTCTTTTT
         .   |   .|         .         |  .         |   .  ||     |        | . |       .
             4096                     4117                4132    4140     4148
                 4101                              4126    4133   4140         4152
                                                          4132    4140
                                                                  4140
                                                                                  Hind III
                                                                                  |
GAAGTAATCAAAATTGTTAGAAGTGCCTATTCAGAAAACTATCAAGGGGCTAATAGGGAATACATTACCATTCTTTGCAA  4240
CTTCATTAGTTTTAACAATCTTCACGGATAAGTCTTTTGATAGTTCCCCGATTATCCCTTATGTAATGGTAAGAAACGTT
         .         .         .         .         .         .         .        |
                                                                                  4240
                                                                 Apo I
                         Bsr I                                  Mse I
Alu I                 Mse I                                    Dra I
|                     |   |                                    || |
AGCTTGGGTATCAAGTGATTTAACCAGTAAAGATTTATTTGTCCGTCAAGGGTGGTTTAAATTCAAGAAAAAAAGAAGCG  4320
TCGAACCCATAGTTCACTAAATTGGTCATTTCTAAATAAACAGGCAGTTCCCACCAAATTTAAGTTCTTTTTTTCTTCGC
|        .            |   |    .         .         .       || |.         .        .
4241                  4260                                 4296
                          4264                              4297
                                                             4299
```

FIG. 2b-20

```
   Mae II
   Afl III
 Hinc II
Mae II                                    Mse I                        Bst1107 I
                                  Mbo II          BspW I               Acc I
AACGTCAACGTGTTCATTTGTCAGAATGGAAAGAAGATTTAATGGCTTATATTAGCGAAAAAAGCGATGTATACAAGCCT  4400
TTGCAGTTGCACAAGTAAACAGTCTTACCTTTCTTCTAAATTACCGAATATAATCGCTTTTTTCGCTACATATGTTCGGA
4322                              4353            4375                 4389
 4324                                   4359                           4389
   4328
   4328

                                                                             Rsa I
                                      Bsm I                                  Csp6 I
   Mae III                        Bfa I                              Eco57 I I  Eco57 I
TATTTAGTGACGACCAAAAAAGAGATTAGAGAAGTGCTAGGCATTCCTGAACGGACATTAGATAAATTGCTGAAGGTACT  4480
ATAAATCACTGCTGGTTTTTTCTCTAATCTCTTCACGATCCGTAAGGACTTGCCTGTAATCTATTTAACGACTTCCATGA
   4407                           4437                               4470   4479
                                     4441                                4476
                                                                         4476

                              ScrF I
                              EcoR II
                              Dsa V
                              BstN I
   Tfi I                   Mse I  Mbo II                                   Mse I
   Hinf I  Apo I     Mse I    BstK I         Bsm I       Bfa I
GAAGGCGAATCAGGAAATTTTCTTTAAGATTAAACCAGGAAGAAATGGTGGCATTCAACTTGCTAGTGTTAAATCATTGT  4560
CTTCCGCTTAGTCCTTTAAAAGAAATTCTAATTTGGTCCTTCTTTACCACCGTAAGTTGAACGATCACAATTTAGTAACA
   4487    4495      4504     4515           4531        4543
   4487                    4510  4519                              4549
                              4515
                              4515
                              4515
                              4515
```

FIG. 2b-21

```
      Sau3A I
      Mbo I
      Dpn II
      Dpn I
     Taq I
    Cla I
    BspD I  Mse I         Mbo II      Alu I      HinP I
                                                 Hha I
                                                 Hae II   Apo I       Dde I
    || |    |             |           |          ||       |           |
TGCTATCGATCATTAAAGTAAAAAAAGAAGAAAAAGAAAGCTATATAAAGGCGCTGACAAATTCTTTTGACTTAGAGCAT  4640
ACGATAGCTAGTAATTTCATTTTTTTCTTCTTTTTCTTTCGATATATTTCCGCGACTGTTTAAGAAAACTGAATCTCGTA
    || | .  |         .   |  .       |.         ||       |.         .|          .
    4565    4573          4587        4599       4610     4619        4631
    4565                                          4611
     4566                                         4611
      4568
      4568
      4568
      4568

                  Mse I    Bfa I
                 Dra I    Nhe I
          BsmA I         Alu I        Bsl I                 Taq I      Alu I
          |      ||      |||          |                     |          |
ACATTCATTCAAGAGACTTTAAACAAGCTAGCAGAACGCCCTAAAACGGACACACAACTCGATTTGTTTAGCTATGATAC  4720
TGTAAGTAAGTTCTCTGAAATTTGTTCGATCGTCTTGCGGGATTTTGCCTGTGTGTTGAGCTAAACAAATCGATACTATG
     .    |      ||.     ||| .        |.         .          |.         |          .
          4653           4666         4679                  4699       4710
                 4658     4667
                  4659     4668
```

FIG. 2b-22

```
                 Aci I                                          Tth111 II
                 Fau I                                        Mae II
                 ||                                           Afl III
                                                              BsaA I
                                                              ||  |
AGGCTGAAAATAAAACCCGCACTATGCCATTACATTTATATCTATGATACGTGTTTGTTTTTTCTTTGCTGTTTAGCGAA   4800
TCCGACTTTTATTTTGGGCGTGATACGGTAATGTAAATATAGATACTATGCACAAACAAAAAAGAAACGACAAATCGCTT
      .          ||  .        .         .         ||. |        .         .         .
                 4736                                4768
                  4737                                4769
                                                      4769
                                                         4772

                                          Mse I
                                         Ase I
                                      Pac I
                                      Mse I
                                      |   ||
TGATTAGCAGAAATATACAGAGTAAGATTTTAATTAATTATTAGGGGGAGAAGGAGAGAGTAGCCCGAAAACTTTTAGTT   4880
ACTAATCGTCTTTATATGTCTCATTCTAAAATTAATTAATAATCCCCCTCTTCCTCTCTCATCGGGCTTTTGAAAATCAA
      .         .                     |   ||     .          .         .         .         .
                                      4830
                                      4830
                                         4833
                                          4834

                                                  Mnl I
                                                Taq I
                 Mnl I                    Mae II         BspW I                           Mse I
                 |                        |   |  |       |                              |
GGCTTGGACTGAACGAAGTGAGGGAAAGGCTACTAAAACGTCGAGGGGCAGTGAGAGCGAAGCGAACACTTGATTTTTTA   4960
CCGAACCTGACTTGCTTCACTCCCTTTCCGATGATTTTGCAGCTCCCCGTCACTCTCGCTTCGCTTGTGAACTAAAAAAT
      .          |         .              | .|  |       | .         .         .     | .
                 4900                     4918           4928                        4958
                                             4921
                                               4923
```

FIG. 2b-23

```
          Bst1107 I                   Fnu4H I
          Acc I                       Bbv I
          |                           |
ATTTTCTATCTTTTATAGGTCATTAGAGTATACTTATTTGTCCTATAAACTATTTAGCAGCATAATAGATTTATTGAATA  5040
TAAAAGATAGAAAATATCCAGTAATCTCATATGAATAAACAGGATATTTGATAAATCGTCGTATTATCTAAATAACTTAT
    .         .   | .       .         .   | .       .         .
                  4988                    5017
                  4988                    5017
                  Mnl I
 Mse I       Mnl I               Ssp I  Mbo II      Nla III
 |           |  |                |      |           |
GGTCATTTAAGTTGAGCATATTAGAGGAGGAAAATCTTGGAGAAATATTTGAAGAACCCGATTACATGGATTGGATTAGT  5120
CCAGTAAATTCAACTCGTATAATCTCCTCCTTTTAGAACCTCTTTATAAACTTCTTGGGCTAATGTACCTAACCTAATCA
 | .       .  |  |  .        .   |     .|       .   |    .         .
 5047         5064               5084   5091        5105
                 5067
    Mae II
   BsaA I
  Mae III     Mse I          Apo I                                      Bfa I
  | ||        |              |                                          |
TCTTGTGGTTACGTGGTTTTTAACTAAAAGTAGTGAATTTTTGATTTTTGGTGTGTGTGTCTTGTTGTTAGTATTTGCTA  5200
AGAACACCAATGCACCAAAAATTGATTTTCATCACTTAAAAACTAAAAACCACACACACAGAACAACAATCATAAACGAT
  | ||        |      .       |    .         .         .         .       | .
  5128        5140           5155                                       5198
    5130
     5131
     Mse I
     |
GTCAAAGTGATTAAATA  5217
CAGTTTCACTAATTTAT
    .|
     5211
```

FIG. 2b-24 sense:

5' G AAG ATC TTT AAA ATG AAG GAG AAA AAA ATG
AAA ATA GGA TAC GCA CGA GTT TCA ACT CAA
GGA GGA TCC AAA TGA TCA GAT CTT C 3' antisense:5' G AAG ATC TGA TCA TTT GGA TCC TCC TTG AGT
TGA AAC TCG TGC GTA TCC TAT TTT CAT TTT
TTT CTC CTT CAT TTT AAA GAT CTT C 3'

FIG. 2c

| Oligo sequence (5'-3') | Name |
|---|---|
| gga atg aca act tta ata aac tta | m1 para |
| aga tga ata tgc agc agc gat aaa tct | m1 anti |
| aaa aaa gaa gat gtt ata aaa aaa tac | m2 para |
| tga aga cat aTC ATc aTC taa gtt tat | m2 anti |
| gtt ata aaa aaa tac aat ttg cat | m3 para |
| atc tGc tGC tGC tga aga cat aaa tcc | m3 anti |
| caa aaa act gta tcc aat aca atg | m4 para |
| aga aat tgt atC ttC aTC aat act atc | m4 anti |
| TtA tac att tgg ggt atc aaa agc | m5 anti |
| ctt aat tgg aat ggt gct aac tgg | m6 para |
| ata ata aGC gtt tct ttc acg | m6 anti |
| tat tat ctt aat tgg aat ggt gct | m7 para |
| aca gtt tTG ttG CTg ctG cat ttt aac | m7 anti |
| ggaggatccaaatgaatgatataggtaaaactactact | cpbacmF |
| atggatccgtctaaatagctgttactttgtgag | cpbR |
| ggaggatccaaatgaagaaaaaatttatttcattagttatag | cpbF2 |

FIG. 3a

1. PCR of pJF2000 *cpb* template with [cpbF2] and [m1-anti] primers generated the *m1*-5' half PCR product. The [m1-anti] primer contained the desired site-specific mutations.

2. PCR of pJF2000 *cpb* template with [m1-para] and [cpbR] generated the *m1*-3' half PCR product.

3. Ligation of 1. and 2. PCR products, generated a template representing the complete *m1* gene. This complete gene was then amplified using the [cpbF2] and [cpbR] primers, generating a product with *Bam*H1 ends.

4. This PCR product was cloned into *Bam*H1 digested expressor plasmid pKS90-1 and transformation into *L. lactis pep5 acmA*.

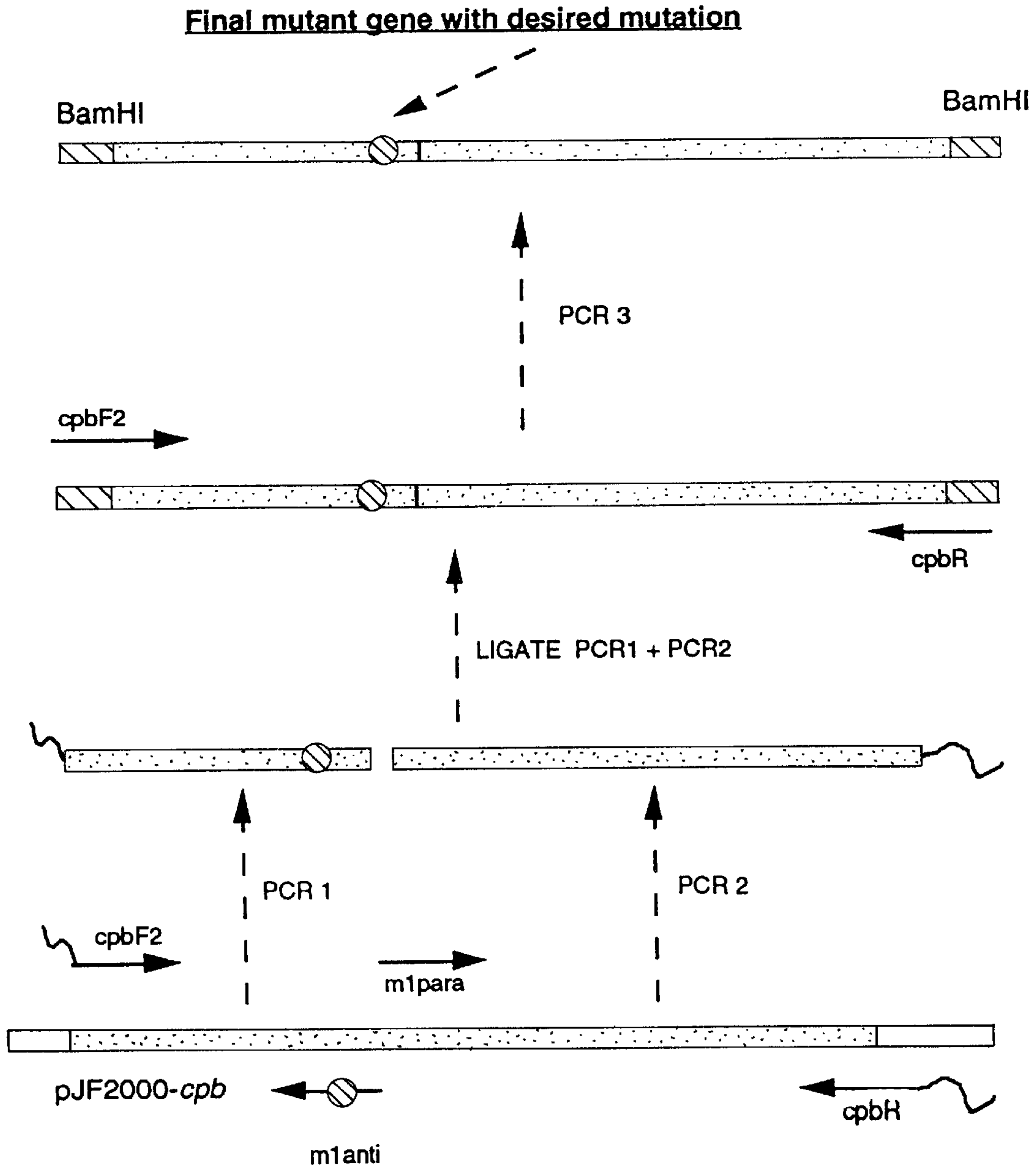

FIG. 3b

Cpb 1 MKKKFISLVIVSSLLNGCLLSPTLVYANDIGKTTTITRNKTSDGYTIITQ 50

51 NKDQIISYQSVDSSSKNEDGFTASIDARFIDDKYSSEMTTLINLTGFMSS 100

101 KKEDVIKKYNLHDVTNSTAINFPVRYSISILNESINENVKIVDSIPKNTI 150

151 SQKTVSNTMGYKIGGSIEIEENKPKASIESEYAESSTIEYVQPDFSTIQT 200

201 DHSTSKASWDTKFTETTRGNYNLKSNNPVYGNEMFMYGRYTNVPATENII 250

251 PDYQMSKLITGGLNPNMSVVLTAPNGTEESIIKVKMERERNCYYLNWNGA 300

301 NWVGQVYSRLAFDTPNVDSHIFTFKINWLTHKVTAI 337

FIG. 4

SEQUENCE LISTING

```
<160> NUMBER OF SEQ ID NOS: 29

<210> SEQ ID NO 1
<211> LENGTH: 60
<212> TYPE: DNA
<213> ORGANISM: Clostridium perfringens

<400> SEQUENCE: 1

gaagatctga tcatttggat cctccttgag ttgaaactcg tgcgtatcct attttcattt     60


<210> SEQ ID NO 2
<211> LENGTH: 38
<212> TYPE: DNA
<213> ORGANISM: Clostridium perfringens

<400> SEQUENCE: 2

ggaggatcca aatgaatgat ataggtaaaa ctactact                             38


<210> SEQ ID NO 3
<211> LENGTH: 42
<212> TYPE: DNA
<213> ORGANISM: Clostridium perfringens

<400> SEQUENCE: 3

ggaggatcca aatgaagaaa aaatttattt cattagttat ag                        42


<210> SEQ ID NO 4
<211> LENGTH: 33
<212> TYPE: DNA
<213> ORGANISM: Clostridium perfringens

<400> SEQUENCE: 4

atggatccgt ctaaatagct gttactttgt gag                                  33


<210> SEQ ID NO 5
<211> LENGTH: 64
<212> TYPE: DNA
<213> ORGANISM: Clostridium perfringens

<400> SEQUENCE: 5
```

-continued

```
gctagttttt gttgtaattt gttatttggg aattttattt tgggtattgg tagtcgagat     60

ttta                                                                  64


<210> SEQ ID NO 6
<211> LENGTH: 27
<212> TYPE: DNA
<213> ORGANISM: Clostridium perfringens

<400> SEQUENCE: 6

agatgaatat gcagcagcga taaatct                                         27


<210> SEQ ID NO 7
<211> LENGTH: 24
<212> TYPE: DNA
<213> ORGANISM: Clostridium perfringens

<400> SEQUENCE: 7

gaaatgacaa ctttaataaa ctta                                            24


<210> SEQ ID NO 8
<211> LENGTH: 27
<212> TYPE: DNA
<213> ORGANISM: Clostridium perfringens

<400> SEQUENCE: 8

tgaagacata tcatcatcta agtttat                                         27


<210> SEQ ID NO 9
<211> LENGTH: 27
<212> TYPE: DNA
<213> ORGANISM: Clostridium perfringens

<400> SEQUENCE: 9

aaaaaagaag atgttataaa aaaatac                                         27


<210> SEQ ID NO 10
<211> LENGTH: 27
<212> TYPE: DNA
<213> ORGANISM: Clostridium perfringens

<400> SEQUENCE: 10

atctgctgct gctgaagaca taaatcc                                         27


<210> SEQ ID NO 11
<211> LENGTH: 24
<212> TYPE: DNA
<213> ORGANISM: Clostridium perfringens

<400> SEQUENCE: 11

gttataaaaa aatacaattt gcat                                            24


<210> SEQ ID NO 12
<211> LENGTH: 27
<212> TYPE: DNA
<213> ORGANISM: Clostridium perfringens

<400> SEQUENCE: 12

agaaattgta tcttcatcaa tactatc                                         27


<210> SEQ ID NO 13
<211> LENGTH: 24
<212> TYPE: DNA
<213> ORGANISM: Clostridium perfringens
```

-continued

<400> SEQUENCE: 13
caaaaaactg tatccaatac aatg 24

<210> SEQ ID NO 14
<211> LENGTH: 24
<212> TYPE: DNA
<213> ORGANISM: Clostridium perfringens

<400> SEQUENCE: 14
ttatacattt ggggtatcaa aagc 24

<210> SEQ ID NO 15
<211> LENGTH: 21
<212> TYPE: DNA
<213> ORGANISM: Clostridium perfringens

<400> SEQUENCE: 15
ataataagcg tttctttcac g 21

<210> SEQ ID NO 16
<211> LENGTH: 24
<212> TYPE: DNA
<213> ORGANISM: Clostridium perfringens

<400> SEQUENCE: 16
cttaattgga atggtgctaa ctgg 24

<210> SEQ ID NO 17
<211> LENGTH: 27
<212> TYPE: DNA
<213> ORGANISM: Clostridium perfringens

<400> SEQUENCE: 17
acagttttgt tgctgctgca ttttaac 27

<210> SEQ ID NO 18
<211> LENGTH: 24
<212> TYPE: DNA
<213> ORGANISM: Clostridium perfringens

<400> SEQUENCE: 18
tattatctta attggaatgg tgct 24

<210> SEQ ID NO 19
<211> LENGTH: 29
<212> TYPE: DNA
<213> ORGANISM: Clostridium perfringens

<400> SEQUENCE: 19
gaagatctct agctttgagc tgtaataga 29

<210> SEQ ID NO 20
<211> LENGTH: 33
<212> TYPE: DNA
<213> ORGANISM: Clostridium perfringens

<400> SEQUENCE: 20
cggaattcag ttgaactact ttttttagtt tta 33

<210> SEQ ID NO 21
<211> LENGTH: 33
<212> TYPE: DNA

-continued

<213> ORGANISM: Clostridium perfringens

<400> SEQUENCE: 21
gaagatctga tacttgtatt ataacatatc tac 33

<210> SEQ ID NO 22
<211> LENGTH: 30
<212> TYPE: DNA
<213> ORGANISM: Clostridium perfringens

<400> SEQUENCE: 22
cggaattcga ttaagtcatc ttacctcttt 30

<210> SEQ ID NO 23
<211> LENGTH: 31
<212> TYPE: DNA
<213> ORGANISM: Clostridium perfringens

<400> SEQUENCE: 23
gaagatctgt aatgtttcgc aactctacta t 31

<210> SEQ ID NO 24
<211> LENGTH: 32
<212> TYPE: DNA
<213> ORGANISM: Clostridium perfringens

<400> SEQUENCE: 24
cggaattcag gactaattga tgaaactttt ct 32

<210> SEQ ID NO 25
<211> LENGTH: 5217
<212> TYPE: DNA
<213> ORGANISM: Clostridium perfringens

<400> SEQUENCE: 25
gaattcgatt aagtcatctt acctctttta ttagtttttt cttataatct aatgataaca 60
tttttataat taatctataa accatatccc tctttggaat caaaatttat tatctactcc 120
tttgtagata tgttataata caagtatcag atctttaaaa tgaaggagaa aaaaatgaaa 180
ataggatacg cacgagtttc aactcaagga ggatccaaat gatcagatcc ggctgctaac 240
aaagcccgaa aggaagctga gttggctgct gccaccgctg agcaataact agcataaccc 300
cttggggcct ctaaacgggt cttgaggggt tttttgctga aaggaggaac tatatccgga 360
tgacctgcag gcaagctcta gaatcgatac gattttgaag tggcaacaga taaaaaaaag 420
cagtttaaaa ttgttgctga acttttaaaa caagcaaata caatcattgt cgcaacagat 480
agcgacagag aaggcgaaaa cattgcctgg tcgatcattc ataaagcaaa tgccttttct 540
aaagataaaa cgtataaaag actatggatc aatagtttag aaaaagatgt gatccgtagc 600
ggttttcaaa atttgcaacc aggaatgaat tactatccct tttatcaaga agcgcaaaag 660
aaaaacgaaa tgatacacca atcagtgcaa aaaaagatat aatgggagat aagacggttc 720
gtgttcgtgc tgacttgcac catatcataa aaatcgaaac agcaaagaat ggcggaaacg 780
taaaagaagt tatggaaata agacttagaa gcaaacttaa gagtgtgttg atagtgcagt 840
atcttaaaat tttgtataat aggaattgaa gttaaattag atgctaaaaa tttgtaatta 900
agaaggagtg attacatgaa caaaaatata aaatattctc aaaacttttt aacgagtgaa 960
aaagtactca accaaataat aaaacaattg aatttaaaag aaaccgatac cgtttacgaa 1020
attggaacag gtaaagggca tttaacgacg aaactggcta aaataagtaa acaggtaacg 1080

-continued

```
tctattgaat tagacagtca tctattcaac ttatcgtcag aaaaattaaa actgaatact   1140
cgtgtcactt taattcacca agatattcta cagtttcaat tccctaacaa acagaggtat   1200
aaaattgttg ggagtattcc ttaccattta agcacacaaa ttattaaaaa agtggttttt   1260
gaaagccatg cgtctgacat ctatctgatt gttgaagaag gattctacaa gcgtaccttg   1320
gatattcacc gaacactagg gttgctcttg cacactcaag tctcgattca gcaattgctt   1380
aagctgccag cggaatgctt tcatcctaaa ccaaaagtaa acagtgtctt aataaaactt   1440
acccgccata ccacagatgt tccagataaa tattggaagc tatatacgta ctttgtttca   1500
aaatgggtca atcgagaata tcgtcaactg tttactaaaa atcagtttca tcaagcaatg   1560
aaacacgcca aagtaaacaa tttaagtacc gttacttatg agcaagtatt gtctattttt   1620
aatagttatc tattatttaa cgggaggaaa taattctatg agtcgctttt gtaaatttgg   1680
aaagttacac gttactaaag ggaatgtaga taaattatta ggtatactac tgacagcttc   1740
caaggagcta aagaggtccc tagcgctctt atcatgggga agctcggatc atatgcaaga   1800
caaaataaac tcgcaacagc acttggagaa atgggacgaa tcgagaaaac cctctttacg   1860
ctggattaca tatctaataa agccgtaagg agacgggttc aaaaaggttt aaataaagga   1920
gaagcaatca atgcattagc tagaactata ttttttggac aacgtggaga atttagagaa   1980
cgtgctctcc aagaccagtt acaaagagct agtgcactaa acataattat taacgctata   2040
agtgtgtgga acactgtata tatggaaaaa gccgtagaag aattaaaagc aagaggagaa   2100
tttagagaag atttaatgcc atatgcgtgg ccgttaggat gggaacatat caattttctt   2160
ggagaataca aatttgaagg attacatgac actgggcaaa tgaatttacg tcctttacgt   2220
ataaaagagc cgttttattc ttaatataac ggctcttttt atagaaaaaa tccttagcgt   2280
ggtttttttc cgaaatgctg gcggtacccc aagaattaga aatgagtaga tcaaattatt   2340
cacgaataga atcaggaaaa tcagatccaa ccataaaaac actagaacaa attgcaaagt   2400
taactaactc aacgctagta gtggatttaa tcccaaatga gccaacagaa ccagagccag   2460
aaacagaatc agaacaagta acattggatt tagaaatgga agaagaaaaa agcaatgact   2520
tcgtgtgaat aatgcacgaa atcgttgctt attttttttt aaaagcggta tactagatat   2580
aacgaaacaa cgaactgaat agaaacgaaa aaagagccat gacacattta taaaatgttt   2640
gacgacattt tataaatgca tagcccgata agattgccaa accaacgctt atcagttagt   2700
cagatgaact cttccctcgt aagaagttat ttaattaact ttgtttgaag acggtatata   2760
accgtactat cattatatag ggaaatcaga gagttttcaa gtatctaagc tactgaattt   2820
aagaattgtt aagcaatcaa tcggaaatcg tttgattgct ttttttgtat tcatttatag   2880
aaggtggagt ttgtatgaat catgatgaat gtaaaactta tataaaaaat agtttattgg   2940
agataagaaa attagcaaat atctatacac tagaaacgtt taagaaagag ttagaaaaga   3000
gaaatatcta cttagaaaca aaatcagata agtatttttc ttcggagggg gaagattata   3060
tatataagtt aatagaaaat aacaaaataa tttattcgat tagtggaaaa aaattgactt   3120
ataaaggaaa aaaatctttt tcaaaacatg caatattgaa acagttgaat gaaaaagcaa   3180
accaagttaa ttaaacaacc tattttatag gatttatagg aaaggagaac agctgaatga   3240
atatcccttt tgttgtagaa actgtgcttc atgacggctt gttaaagtac aaatttaaaa   3300
atagtaaaat tcgctcaatc actaccaagc caggtaaaag caaaggggct atttttgcgt   3360
atcgctcaaa atcaagcatg attggcggtc gtggtgttgt tctgacttcc gaggaagcga   3420
```

-continued

```
ttcaagaaaa tcaagataca tttacacatt ggacacccaa cgtttatcgt tatggaacgt   3480

atgcagacga aaaccgttca tacacgaaag gacattctga aaacaattta agacaaatca   3540

ataccttctt tattgatttt gatattcaca cggcaaaaga aactatttca gcaagcgata   3600

ttttaacaac cgctattgat ttaggtttta tgcctactat gattatcaaa tctgataaag   3660

gttatcaagc atattttgtt ttagaaacgc cagtctatgt gacttcaaaa tcagaattta   3720

aatctgtcaa agcagccaaa ataatttcgc aaaatatccg agaatatttt ggaaagtctt   3780

tgccagttga tctaacgtgt aatcattttg gtattgctcg cataccaaga acggacaatg   3840

tagaattttt tgatcctaat taccgttatt ctttcaaaga atggcaagat tggtctttca   3900

aacaaacaga taataagggc tttactcgtt caagtctaac ggttttaagc ggtacagaag   3960

gcaaaaaaca agtagatgaa ccctggttta atctcttatt gcacgaaacg aaattttcag   4020

gagaaaaggg tttaataggg cgtaataacg tcatgtttac cctctcttta gcctacttta   4080

gttcaggcta ttcaatcgaa acgtgcgaat ataatatgtt tgagtttaat aatcgattag   4140

atcaaccctt agaagaaaaa gaagtaatca aaattgttag aagtgcctat tcagaaaact   4200

atcaaggggc taatagggaa tacattacca ttctttgcaa agcttgggta tcaagtgatt   4260

taaccagtaa agatttattt gtccgtcaag ggtggtttaa attcaagaaa aaaagaagcg   4320

aacgtcaacg tgttcatttg tcagaatgga aagaagattt aatggcttat attagcgaaa   4380

aaagcgatgt atacaagcct tatttagtga cgaccaaaaa agagattaga gaagtgctag   4440

gcattcctga acggacatta gataaattgc tgaaggtact gaaggcgaat caggaaattt   4500

tctttaagat taaaccagga agaaatggtg gcattcaact tgctagtgtt aaatcattgt   4560

tgctatcgat cattaaagta aaaaaagaag aaaaagaaag ctatataaag gcgctgacaa   4620

attcttttga cttagagcat acattcattc aagagacttt aaacaagcta gcagaacgcc   4680

ctaaaacgga cacacaactc gatttgttta gctatgatac aggctgaaaa taaaacccgc   4740

actatgccat tacatttata tctatgatac gtgtttgttt tttctttgct gtttagcgaa   4800

tgattagcag aaatatacag agtaagattt taattaatta ttagggggag aaggagagag   4860

tagcccgaaa acttttagtt ggcttggact gaacgaagtg agggaaaggc tactaaaacg   4920

tcgaggggca gtgagagcga agcgaacact tgattttta attttctatc ttttataggt   4980

cattagagta tacttatttg tcctataaac tatttagcag cataatagat ttattgaata   5040

ggtcatttaa gttgagcata ttagaggagg aaaatcttgg agaaatattt gaagaacccg   5100

attacatgga ttggattagt tcttgtggtt acgtggtttt taactaaaag tagtgaattt   5160

ttgatttttg gtgtgtgtgt cttgttgtta gtatttgcta gtcaaagtga ttaaata      5217
```

<210> SEQ ID NO 26
<211> LENGTH: 5230
<212> TYPE: DNA
<213> ORGANISM: Clostridium perfringens

<400> SEQUENCE: 26

```
gaattcgatt aagtcatctt acctctttta ttagtttttt cttataatct aatgataaca     60

tttttataat taatctataa accatatccc tctttggaat caaaatttat tatctactcc    120

tttgtagata tgttataata caagtatcag atctgggaga ccacaacggt ttcccactag    180

aaataatttt gtttaacttt agaaaggaga tatacgcatg caggatatct ctagaatgga    240

tccggctgct aacaaagccc gaaaggaagc tgagttggct gctgccaccg ctgagcaata    300

actagcataa ccccttgggg cctctaaacg ggtcttgagg ggttttttgc tgaaaggagg    360
```

-continued

```
aactatatcc ggatgacctg caggcaagct ctagaatcga tacgattttg aagtggcaac    420
agataaaaaa aagcagttta aaattgttgc tgaactttta aaacaagcaa atacaatcat    480
tgtcgcaaca gatagcgaca gagaaggcga aaacattgcc tggtcgatca ttcataaagc    540
aaatgccttt tctaaagata aaacgtataa aagactatgg atcaatagtt tagaaaaaga    600
tgtgatccgt agcggttttc aaaatttgca accaggaatg aattactatc ccttttatca    660
agaagcgcaa aagaaaaacg aaatgataca ccaatcagtg caaaaaaaga tataatggga    720
gataagacgg ttcgtgttcg tgctgacttg caccatatca taaaaatcga aacagcaaag    780
aatggcggaa acgtaaaaga agttatggaa ataagactta gaagcaaact taagagtgtg    840
ttgatagtgc agtatcttaa aattttgtat aataggaatt gaagttaaat tagatgctaa    900
aaatttgtaa ttaagaagga gtgattacat gaacaaaaat ataaaatatt ctcaaaactt    960
tttaacgagt gaaaaagtac tcaaccaaat aataaaacaa ttgaatttaa aagaaaccga   1020
taccgtttac gaaattggaa caggtaaagg gcatttaacg acgaaactgg ctaaaataag   1080
taaacaggta acgtctattg aattagacag tcatctattc aacttatcgt cagaaaaatt   1140
aaaactgaat actcgtgtca ctttaattca ccaagatatt ctacagtttc aattccctaa   1200
caaacagagg tataaaattg ttgggagtat tccttaccat ttaagcacac aaattattaa   1260
aaaagtggtt tttgaaagcc atgcgtctga catctatctg attgttgaag aaggattcta   1320
caagcgtacc ttggatattc accgaacact agggttgctc ttgcacactc aagtctcgat   1380
tcagcaattg cttaagctgc cagcggaatg ctttcatcct aaaccaaaag taaacagtgt   1440
cttaataaaa cttacccgcc ataccacaga tgttccagat aaatattgga agctatatac   1500
gtactttgtt tcaaaatggg tcaatcgaga atatcgtcaa ctgtttacta aaaatcagtt   1560
tcatcaagca atgaaacacg ccaaagtaaa caatttaagt accgttactt atgagcaagt   1620
attgtctatt tttaatagtt atctattatt taacgggagg aaataattct atgagtcgct   1680
tttgtaaatt tggaaagtta cacgttacta aagggaatgt agataaatta ttaggtatac   1740
tactgacagc ttccaaggag ctaaagaggt ccctagcgct cttatcatgg ggaagctcgg   1800
atcatatgca agacaaaata aactcgcaac agcacttgga gaaatgggac gaatcgagaa   1860
aaccctcttt acgctggatt acatatctaa taaagccgta aggagacggg ttcaaaaagg   1920
tttaaataaa ggagaagcaa tcaatgcatt agctagaact atattttttg gacaacgtgg   1980
agaatttaga gaacgtgctc tccaagacca gttacaaaga gctagtgcac taaacataat   2040
tattaacgct ataagtgtgt ggaacactgt atatatggaa aaagccgtag aagaattaaa   2100
agcaagagga gaatttagag aagatttaat gccatatgcg tggccgttag gatgggaaca   2160
tatcaatttt cttggagaat acaaatttga aggattacat gacactgggc aaatgaattt   2220
acgtccttta cgtataaaag agccgtttta ttcttaatat aacggctctt tttatagaaa   2280
aaatccttag cgtggttttt ttccgaaatg ctggcggtac cccaagaatt agaaatgagt   2340
agatcaaatt attcacgaat agaatcagga aaatcagatc caaccataaa aacactagaa   2400
caaattgcaa agttaactaa ctcaacgcta gtagtggatt taatcccaaa tgagccaaca   2460
gaaccagagc cagaaacaga atcagaacaa gtaacattgg atttagaaat ggaagaagaa   2520
aaaagcaatg acttcgtgtg aataatgcac gaaatcgttg cttatttttt tttaaaagcg   2580
gtatactaga tataacgaaa caacgaactg aatagaaacg aaaaaagagc catgacacat   2640
ttataaaatg tttgacgaca ttttataaat gcatagcccg ataagattgc caaaccaacg   2700
```

-continued

```
cttatcagtt agtcagatga actcttccct cgtaagaagt tatttaatta actttgtttg   2760
aagacggtat ataaccgtac tatcattata tagggaaatc agagagtttt caagtatcta   2820
agctactgaa tttaagaatt gttaagcaat caatcggaaa tcgtttgatt gctttttttg   2880
tattcattta tagaaggtgg agtttgtatg aatcatgatg aatgtaaaac ttatataaaa   2940
aatagtttat tggagataag aaaattagca aatatctata cactagaaac gtttaagaaa   3000
gagttagaaa agagaaatat ctacttagaa acaaaatcag ataagtattt ttcttcggag   3060
ggggaagatt atatatataa gttaatagaa aataacaaaa taatttattc gattagtgga   3120
aaaaaattga cttataaagg aaaaaaatct ttttcaaaac atgcaatatt gaaacagttg   3180
aatgaaaaag caaaccaagt taattaaaca acctatttta taggatttat aggaaaggag   3240
aacagctgaa tgaatatccc ttttgttgta gaaactgtgc ttcatgacgg cttgttaaag   3300
tacaaattta aaaatagtaa aattcgctca atcactacca agccaggtaa aagcaaaggg   3360
gctatttttg cgtatcgctc aaaatcaagc atgattggcg gtcgtggtgt tgttctgact   3420
tccgaggaag cgattcaaga aaatcaagat acatttacac attggacacc caacgtttat   3480
cgttatggaa cgtatgcaga cgaaaaccgt tcatacacga aaggacattc tgaaaacaat   3540
ttaagacaaa tcaatacctt ctttattgat tttgatattc acacggcaaa agaaactatt   3600
tcagcaagcg atattttaac aaccgctatt gatttaggtt ttatgcctac tatgattatc   3660
aaatctgata aaggttatca agcatatttt gttttagaaa cgccagtcta tgtgacttca   3720
aaatcagaat ttaaatctgt caaagcagcc aaaataattt cgcaaaatat ccgagaatat   3780
tttggaaagt ctttgccagt tgatctaacg tgtaatcatt ttggtattgc tcgcatacca   3840
agaacggaca atgtagaatt ttttgatcct aattaccgtt attctttcaa agaatggcaa   3900
gattggtctt tcaaacaaac agataataag ggctttactc gttcaagtct aacggtttta   3960
agcggtacag aaggcaaaaa acaagtagat gaaccctggt ttaatctctt attgcacgaa   4020
acgaaatttt caggagaaaa gggtttaata gggcgtaata acgtcatgtt taccctctct   4080
ttagcctact ttagttcagg ctattcaatc gaaacgtgcg aatataatat gtttgagttt   4140
aataatcgat tagatcaacc cttagaagaa aaagaagtaa tcaaaattgt tagaagtgcc   4200
tattcagaaa actatcaagg ggctaatagg gaatacatta ccattctttg caaagcttgg   4260
gtatcaagtg atttaaccag taaagattta tttgtccgtc aagggtggtt taaattcaag   4320
aaaaaaagaa gcgaacgtca acgtgttcat ttgtcagaat ggaaagaaga tttaatggct   4380
tatattagcg aaaaaagcga tgtatacaag ccttatttag tgacgaccaa aaaagagatt   4440
agagaagtgc taggcattcc tgaacggaca ttagataaat tgctgaaggt actgaaggcg   4500
aatcaggaaa ttttctttaa gattaaacca ggaagaaatg gtggcattca acttgctagt   4560
gttaaatcat tgttgctatc gatcattaaa gtaaaaaaag aagaaaaaga aagctatata   4620
aaggcgctga caaattcttt tgacttagag catacattca ttcaagagac tttaaacaag   4680
ctagcagaac gccctaaaac ggacacacaa ctcgatttgt ttagctatga tacaggctga   4740
aaataaaacc cgcactatgc cattacattt atatctatga tacgtgtttg ttttttcttt   4800
gctgtttagc gaatgattag cagaaatata cagagtaaga ttttaattaa ttattagggg   4860
gagaaggaga gagtagcccg aaaactttta gttggcttgg actgaacgaa gtgagggaaa   4920
ggctactaaa acgtcgaggg gcagtgagag cgaagcgaac acttgatttt ttaattttct   4980
atcttttata ggtcattaga gtatacttat ttgtcctata aactatttag cagcataata   5040
gatttattga ataggtcatt taagttgagc atattagagg aggaaaatct tggagaaata   5100
```

-continued tttgaagaac ccgattacat ggattggatt agttcttgtg gttacgtggt ttttaactaa 5160
aagtagtgaa tttttgattt ttggtgtgtg tgtcttgttg ttagtatttg ctagtcaaag 5220
tgattaaata 5230

<210> SEQ ID NO 27
<211> LENGTH: 5231
<212> TYPE: DNA
<213> ORGANISM: Clostridium perfringens

<400> SEQUENCE: 27
gaattcgatt aagtcatctt acctctttta ttagtttttt cttataatct aatgataaca 60
tttttataat taatctataa accatatccc tctttggaat caaaatttat tatctactcc 120
tttgtagata tgttataata caagtatcag atctataggg agaccacaac ggtttccctc 180
tagaaataat tttgtttaac tttaagaagg agatatacat atggctagca tgactggtgg 240
acagcaaatg ggtcgcggat ccggctgcta acaaagcccg aaaggaagct gagttggctg 300
ctgccaccgc tgagcaataa ctagcataac cccttggggc ctctaaacgg gtcttgaggg 360
gttttttgct gaaaggagga actatatccg actagaatcg atacgatttt gaagtggcaa 420
cagataaaaa aaagcagttt aaaattgttg ctgaactttt aaaacaagca aatacaatca 480
ttgtcgcaac agatagcgac agagaaggcg aaaacattgc ctggtcgatc attcataaag 540
caaatgcctt ttctaaagat aaaacgtata aaagactatg gatcaatagt ttagaaaaag 600
atgtgatccg tagcggtttt caaaatttgc aaccaggaat gaattactat ccctttttatc 660 aagaagcgca aaagaaaaac gaaatgatac accaatcagt gcaaaaaaag atataatggg 720
agataagacg gttcgtgttc gtgctgactt gcaccatatc ataaaaatcg aaacagcaaa 780
gaatggcgga aacgtaaaag aagttatgga aataagactt agaagcaaac ttaagagtgt 840
gttgatagtg cagtatctta aaattttgta taataggaat tgaagttaaa ttagatgcta 900
aaaatttgta attaagaagg agtgattaca tgaacaaaaa tataaaatat tctcaaaact 960
ttttaacgag tgaaaaagta ctcaaccaaa taataaaaca attgaattta aaagaaaccg 1020
ataccgttta cgaaattgga acaggtaaag ggcatttaac gacgaaactg gctaaaataa 1080
gtaaacaggt aacgtctatt gaattagaca gtcatctatt caacttatcg tcagaaaaat 1140
taaaactgaa tactcgtgtc actttaattc accaagatat tctacagttt caattcccta 1200
acaaacagag gtataaaatt gttgggagta ttccttacca tttaagcaca caaattatta 1260
aaaaagtggt tttgaaagc catgcgtctg acatctatct gattgttgaa gaaggattct 1320
acaagcgtac cttggatatt caccgaacac tagggttgct cttgcacact caagtctcga 1380
ttcagcaatt gcttaagctg ccagcggaat gctttcatcc taaaccaaaa gtaaacagtg 1440
tcttaataaa acttacccgc cataccacag atgttccaga taaatattgg aagctatata 1500
cgtactttgt ttcaaaatgg gtcaatcgag aatatcgtca actgtttact aaaaatcagt 1560
ttcatcaagc aatgaaacac gccaaagtaa acaatttaag taccgttact tatgagcaag 1620
tattgtctat ttttaatagt tatctattat ttaacgggag gaaataattc tatgagtcgc 1680
ttttgtaaat ttggaaagtt acacgttact aaagggaatg tagataaatt attaggtata 1740
ctactgacag cttccaagga gctaaagagg tccctagcgc tcttatcatg gggaagctcg 1800
gatcatatgc aagacaaaat aaactcgcaa cagcacttgg agaaatggga cgaatcgaga 1860
aaaccctctt tacgctggat tacatatcta ataaagccgt aaggagacgg gttcaaaaag 1920

-continued

```
gtttaaataa aggagaagca atcaatgcat tagctagaac tatatttttt ggacaacgtg   1980
gagaatttag agaacgtgct ctccaagacc agttacaaag agctagtgca ctaaacataa   2040
ttattaacgc tataagtgtg tggaacactg tatatatgga aaaagccgta gaagaattaa   2100
aagcaagagg agaatttaga gaagatttaa tgccatatgc gtggccgtta ggatgggaac   2160
atatcaattt tcttggagaa tacaaatttg aaggattaca tgacactggg caaatgaatt   2220
tacgtccttt acgtataaaa gagccgtttt attcttaata taacggctct ttttatagaa   2280
aaaatcctta gcgtggtttt tttccgaaat gctggcggta ccccaagaat tagaaatgag   2340
tagatcaaat tattcacgaa tagaatcagg aaaatcagat ccaaccataa aaacactaga   2400
acaaattgca aagttaacta actcaacgct agtagtggat ttaatcccaa atgagccaac   2460
agaaccagag ccagaaacag aatcagaaca agtaacattg gatttagaaa tggaagaaga   2520
aaaaagcaat gacttcgtgt gaataatgca cgaaatcgtt gcttattttt ttttaaaagc   2580
ggtatactag atataacgaa acaacgaact gaatagaaac gaaaaaagag ccatgacaca   2640
tttataaaat gtttgacgac attttataaa tgcatagccc gataagattg ccaaaccaac   2700
gcttatcagt tagtcagatg aactcttccc tcgtaagaag ttatttaatt aactttgttt   2760
gaagacggta tataaccgta ctatcattat atagggaaat cagagagttt tcaagtatct   2820
aagctactga atttaagaat tgttaagcaa tcaatcggaa atcgtttgat tgcttttttt   2880
gtattcattt atagaaggtg gagtttgtat gaatcatgat gaatgtaaaa cttatataaa   2940
aaatagttta ttggagataa gaaaattagc aaatatctat acactagaaa cgtttaagaa   3000
agagttagaa aagagaaata tctacttaga aacaaaatca gataagtatt tttcttcgga   3060
gggggaagat tatatatata agttaataga aaataacaaa ataatttatt cgattagtgg   3120
aaaaaaattg acttataaag gaaaaaaatc tttttcaaaa catgcaatat tgaaacagtt   3180
gaatgaaaaa gcaaaccaag ttaattaaac aacctatttt ataggattta taggaaagga   3240
gaacagctga atgaatatcc cttttgttgt agaaactgtg cttcatgacg gcttgttaaa   3300
gtacaaattt aaaaatagta aaattcgctc aatcactacc aagccaggta aaagcaaagg   3360
ggctattttt gcgtatcgct caaaatcaag catgattggc ggtcgtggtg ttgttctgac   3420
ttccgaggaa gcgattcaag aaaatcaaga tacatttaca cattggacac ccaacgttta   3480
tcgttatgga acgtatgcag acgaaaaccg ttcatacacg aaaggacatt ctgaaaacaa   3540
tttaagacaa atcaatacct tctttattga ttttgatatt cacacggcaa aagaaactat   3600
ttcagcaagc gatattttaa caaccgctat tgatttaggt tttatgccta ctatgattat   3660
caaatctgat aaaggttatc aagcatattt tgttttagaa acgccagtct atgtgacttc   3720
aaaatcagaa tttaaatctg tcaaagcagc caaaataatt tcgcaaaata tccgagaata   3780
ttttggaaag tctttgccag ttgatctaac gtgtaatcat tttggtattg ctcgcatacc   3840
aagaacggac aatgtagaat tttttgatcc taattaccgt tattctttca aagaatggca   3900
agattggtct ttcaaacaaa cagataataa gggctttact cgttcaagtc taacggtttt   3960
aagcggtaca gaaggcaaaa aacaagtaga tgaaccctgg tttaatctct tattgcacga   4020
aacgaaattt tcaggagaaa agggtttaat agggcgtaat aacgtcatgt ttaccctctc   4080
tttagcctac tttagttcag gctattcaat cgaaacgtgc gaatataata tgtttgagtt   4140
taataatcga ttagatcaac ccttagaaga aaaagaagta atcaaaattg ttagaagtgc   4200
ctattcagaa aactatcaag ggctaatag ggaatacatt accattcttt gcaaagcttg   4260
ggtatcaagt gatttaacca gtaaagattt atttgtccgt caagggtggt ttaaattcaa   4320
```

-continued

```
gaaaaaaaga agcgaacgtc aacgtgttca tttgtcagaa tggaaagaag atttaatggc   4380

ttatattagc gaaaaaagcg atgtatacaa gccttattta gtgacgacca aaaaagagat   4440

tagagaagtg ctaggcattc ctgaacggac attagataaa ttgctgaagg tactgaaggc   4500

gaatcaggaa attttcttta agattaaacc aggaagaaat ggtggcattc aacttgctag   4560

tgttaaatca ttgttgctat cgatcattaa agtaaaaaaa gaagaaaaag aaagctatat   4620

aaaggcgctg acaaattctt ttgacttaga gcatacattc attcaagaga ctttaaacaa   4680

gctagcagaa cgccctaaaa cggacacaca actcgatttg tttagctatg atacaggctg   4740

aaaataaaac ccgcactatg ccattacatt tatatctatg atacgtgttt gttttttctt   4800

tgctgtttag cgaatgatta gcagaaatat acagagtaag attttaatta attattaggg   4860

ggagaaggag agagtagccc gaaaactttt agttggcttg gactgaacga agtgagggaa   4920

aggctactaa aacgtcgagg ggcagtgaga gcgaagcgaa cacttgattt tttaattttc   4980

tatcttttat aggtcattag agtatactta tttgtcctat aaactattta gcagcataat   5040

agatttattg aataggtcat ttaagttgag catattagag gaggaaaatc ttggagaaat   5100

atttgaagaa cccgattaca tggattggat tagttcttgt ggttacgtgg tttttaacta   5160

aaagtagtga atttttgatt tttggtgtgt gtgtcttgtt gttagtattt gctagtcaaa   5220

gtgattaaat a                                                        5231
```

<210> SEQ ID NO 28
<211> LENGTH: 86
<212> TYPE: DNA
<213> ORGANISM: Clostridium perfringens

<400> SEQUENCE: 28

```
gaagatcttt aaaatgaagg agaaaaaaat gaaaatagga tacgcacgag tttcaactca     60

aggaggatcc aaatgatcag atcttc                                          86
```

<210> SEQ ID NO 29
<211> LENGTH: 336
<212> TYPE: PRT
<213> ORGANISM: Clostridium perfringens

<400> SEQUENCE: 29

```
Met Lys Lys Lys Phe Ile Ser Leu Val Ile Val Ser Ser Leu Leu Asn
  1               5                  10                  15

Gly Cys Leu Leu Ser Pro Arg Leu Val Tyr Ala Asn Asp Ile Gly Lys
             20                  25                  30

Thr Thr Thr Ile Thr Arg Asn Lys Thr Ser Asp Gly Tyr Thr Ile Ile
         35                  40                  45

Thr Gln Asn Asp Lys Trp Ile Ile Ser Tyr Gln Ser Val Asp Ser Ser
     50                  55                  60

Ser Lys Asn Glu Asp Gly Phe Thr Ala Ser Ile Asp Ala Arg Phe Ile
 65                  70                  75                  80

Asp Asp Lys Tyr Ser Ser Glu Met Thr Thr Leu Ile Asn Leu Thr Gly
                 85                  90                  95

Phe Met Ser Ser Lys Lys Glu Asp Val Ile Lys Lys Tyr Asn Leu His
            100                 105                 110

Asp Asn Thr Asn Ser Thr Ala Ile Asn Phe Pro Val Arg Tyr Ser Ile
        115                 120                 125

Ser Ile Leu Asn Glu Ser Ile Asn Glu Asn Val Lys Ile Val Asp Ser
    130                 135                 140
```

-continued

```
Ile Pro Lys Asn Thr Ile Ser Gln Lys Thr Val Ser Asn Thr Met Gly
145                 150                 155                 160

Tyr Lys Ile Gly Gly Ser Ile Glu Ile Glu Glu Asn Lys Pro Lys Ala
                165                 170                 175

Ser Ile Glu Ser Glu Tyr Ala Glu Ser Ser Thr Ile Glu Tyr Val Gln
            180                 185                 190

Pro Asp Phe Ser Thr Ile Gln Thr Asp His Ser Thr Ser Lys Ala Ser
        195                 200                 205

Trp Asp Thr Lys Phe Thr Glu Thr Thr Arg Gly Asn Tyr Asn Leu Lys
    210                 215                 220

Ser Asn Asn Pro Val Tyr Gly Asn Glu Met Phe Met Tyr Gly Arg Tyr
225                 230                 235                 240

Thr Asn Val Pro Ala Thr Glu Asn Ile Ile Pro Asp Tyr Gln Met Ser
                245                 250                 255

Lys Leu Ile Thr Gly Gly Leu Asn Pro Asn Met Ser Val Val Leu Thr
            260                 265                 270

Ala Pro Asn Gly Thr Glu Glu Ser Ile Ile Lys Val Lys Met Glu Arg
        275                 280                 285

Glu Arg Asn Cys Tyr Tyr Leu Asn Trp Asn Gly Ala Asn Trp Val Gly
    290                 295                 300

Gln Val Tyr Ser Arg Leu Ala Phe Asp Thr Pro Asn Val Asp Ser His
305                 310                 315                 320

Ile Phe Thr Phe Lys Ile Asn Trp Leu Thr His Lys Val Thr Ala Ile
                325                 330                 335
```

*CLOSTRIDIUM PERFRINGENS* VACCINE

FIELD OF THE INVENTION

The present invention refers to detoxified immunogenic derivatives of *Clostridium perfringens* β-toxin, DNA encoding such derivatives, *Clostridium perfringens* bacteria comprising DNA encoding such derivatives, Gram positive bacterial expression systems comprising DNA encoding such derivatives, non-*Clostridium perfringens*-based Gram positive bacterial expression systems expressing wild-type β-toxin, vaccines for combating *Clostridium perfringens* based thereon, methods for the preparation of native *Clostridium perfringens* β-toxin, methods for the preparation of detoxified immunogenic derivatives of *Clostridium perfringens* β-toxin and to methods for the preparation of vaccines for combating *Clostridium perfringens.*

BACKGROUND OF THE INVENTION

*Clostridium perfringens* (also known as *C. welchii*) is a species of the large genus Clostridium. All bacteria belonging to this genus are spore-forming, anaerobic, Gram positive bacilli. The species *C. perfringens* can be subdivided into subspecies. Five subspecies have been described. These subspecies are generally known as "type" A–E. All subspecies produce several toxins, both major and minor toxins. The four major toxins are the α, β, ε and ι toxin. All *C. perfringens* types produce the α-toxin. The β-toxin is produced by *C. perfringens* types B and C. In addition, a range of minor toxins is produced by all *C. perfringens* types.

It is mainly due to the presence of one or more of these various toxins in the five *C. perfringens* types that all *C. perfringens* species are pathogenic. Type A is known to be pathogenic for both man and pigs. Type B is mainly pathogenic for lamb, sheep and goat, and causes "lamb dysenteria" and haemorragic enteritis. Type C is pathogenic for man, sheep, calf, lamb, pig, and bird. It is the cause of "struck", haemorragic enteritis, necrotic enteritis and enterotoxemia.

As mentioned above, both *C. perfringens* type B and type C are known to produce the β-toxin. The β-toxin is known to play the major role in the pathogenesis of necrotic enteritis in both man and animal. In man, this disease has been termed pigbel (Johnson et al.: Lancet ii: 496–500, (1987)). In animals, necrotic enteritis has been described in calves, lambs and pigs (Hauschild, A. H. W. in S. Kadis, T. C. Montie, (ed.) Microbial toxins, p. 159–188. Academic press, Inc, New York (1971) and Willis, T. A. Anaerobic bacteriology: clinical and laboratory practice, $3^{rd}$ ed. Butterworths, London (1977).

The β-toxin from *Clostridium perfringens* has been isolated in pure form (Sakurai et al., Infect. & Immun. 18: 741–745 (1977), Sakurai et al., Toxicon 25: 1301–1310 (1987)). Much is still unknown about the biophysical properties of the toxin and thus about its mode of action. Due however to the fact that it could be obtained in a purified form the toxicity of β-toxin could be clearly demonstrated in animals. The lethal toxicity of purified β-toxin for e.g. mice and guinea-pigs was shown by Sakurai et al. (Infect. & Immun. 21: 678–680 (1978), Sakurai et al., Toxicon 25: 1301–1310 (1987)).

Recently, the nucleic acid sequence of the *Clostridium perfringens* β-toxin has been elucidated by Hunter et al. (Infect. & Immun. 61: 3958–3965 (1993)). The nucleic acid sequence revealed the size of the β-toxin protein to be about 35 kD.

Due to the fact that the role of *Clostridium perfringens* β-toxin from type B and C in pathogenesis is of such paramount importance, much effort has been put in the development of immunity against this toxin. Immunity against the β-toxin is sufficient to protect against *Clostridium perfringens* type B and type C infection. The only way of inducing immunity against the β-toxin is to administer the toxin to the animal to be protected. It is however obvious that the toxin must be given in a detoxified form, since otherwise administration would lead to severe illness or death of the animal.

Vaccines based on detoxified β-toxin, also called β-toxoid, were available already around 1960 (e.g. G.B. Pat. No. 901,433, and U.S. Pat. No. 3,288,680).

All currently available vaccines based on inactivated *Clostridium perfringens* β-toxin have, however, several important drawbacks. In the first place, all β-toxin-based vaccines comprise chemically detoxified, mainly formalin-detoxified, β-toxin and it was shown through the years that it is very difficult to standardise these chemical detoxification processes. The classical chemical methods for detoxification of proteins have the disadvantage that they alter the overall structure of the protein in a fairly random manner. And as a result, during the process of chemical detoxification the immunogenic properties of the β-toxin also rapidly decrease. This can be seen e.g. from FIG. 5A and FIG. 5B: in FIG. 5B it is shown that at least 1% formalin, a very commonly used inactivation-compound, is necessary to detoxify the β-toxin under certain standard conditions.

From FIGS. 5A and B, it can be seen, however, that the antigenicity titre decreases dramatically with an increasing amount of formalin. A full titre cannot be obtained anyway, because even the lowest amount of formalin needed for detoxification (FIG. 5B) already gives a decrease of the titre. This implicates that there is only a very narrow band, in which both detoxification and a reasonable titre and thus immunogenicity can be obtained. Given this very narrow band, and the fact that there are at least three variables: time of detoxification, temperature and precise formalin-concentration, it is clear that it is very difficult to reproducibly produce detoxified β-toxin. Another approach for the detoxification of β-toxin is therefore highly wanted. No acceptable alternative has been found until now, for the following reason: the delicate balance between a sufficient level of detoxification and remaining immunogenicity implicates a close link between, on the one hand, the structure of the protein and, on the other hand, the biological properties of the protein. It could therefore not be expected to change the protein structure to detoxify the protein, without at the same time significantly impairing the immunogenic characteristics of the protein.

SUMMARY OF THE INVENTION

It is one of the merits of the present invention that it discloses for the first time a way to avoid the above-mentioned problem: using genetic manipulation techniques, specific and relatively large amino acid regions were surprisingly found that can be mutated to provide the desired non-toxic derivatives of β-toxin without significantly impairing its necessary immunogenic properties.

BRIEF DESCRIPTION OF THE DRAWINGS

FIG. 1D: oligonucleotides used to create the PCR derived promotor fragments used in pTREX7, -14 and -1A (shown 5'-3')

FIG. 2A: the TIR coupling vector pKS90, schematic representation of the pKS90 expression cassette.

FIG. 2C: oligonucleotides used to create the artificial DNA sequence forming the TIR region of pKS90.

FIG. 3A: primers used in the construction of the Cpβ-mutants.

FIG. 3B: example of the construction procedure as used for Cpβ M1.

DETAILED DESCRIPTION OF THE INVENTION

Figure 1A:
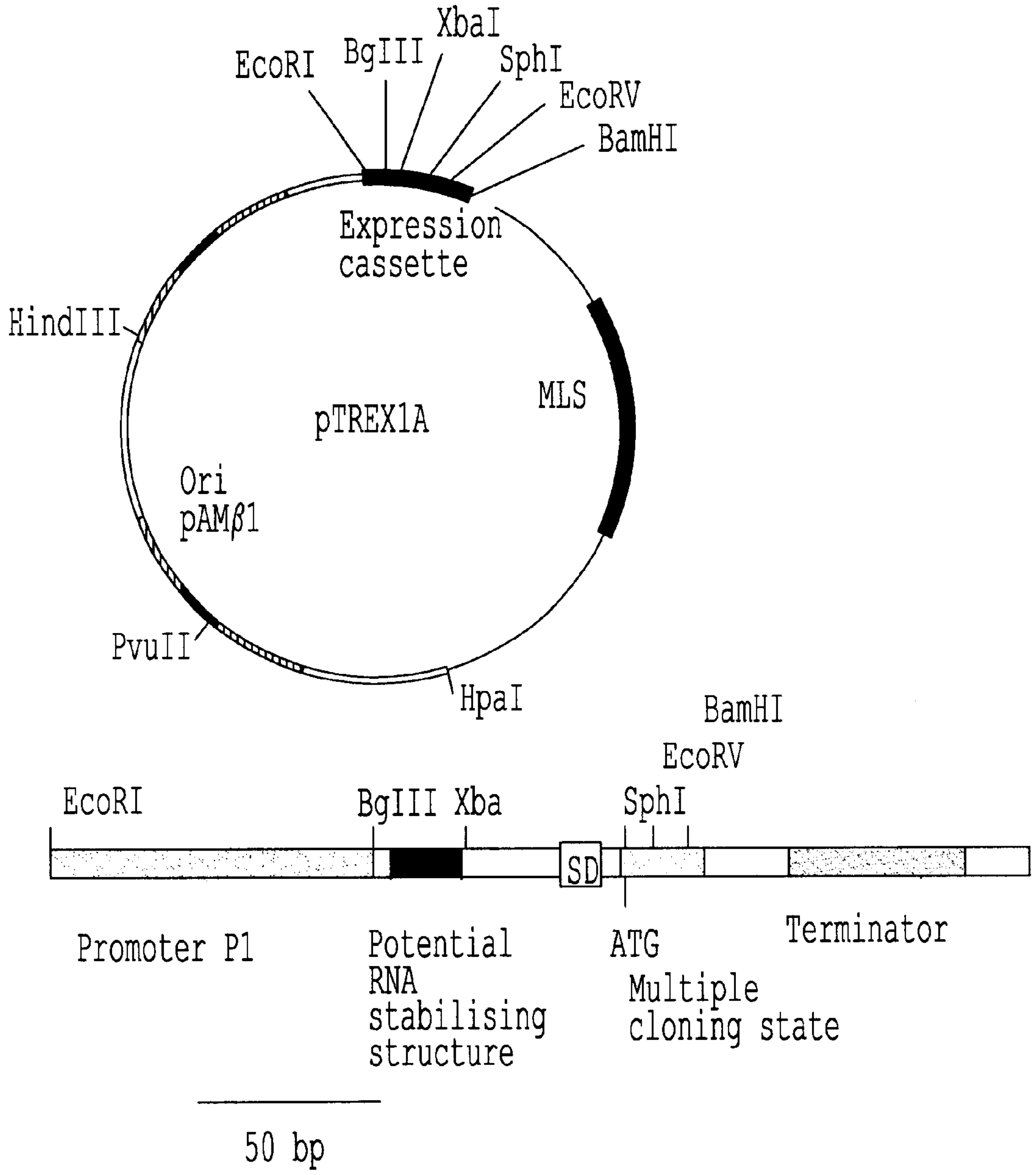
FIG. 1A: structure of plasmid pTREX1ANEW. The coding sequence of the MLS antibiotic resistance marker is shown as a shaded box. Ori pAMB1: origin of replication from the plasmid pAMB1, MLS: macrolides, lincosamindes, streptogramin B antibiotic resistance gene. The structure of the expression cassette cloned between the EcoR1 and blunted Sac1 sites of plL253 is shown below. Different functional regions of the cassette are shown as hatched boxes. Unique restriction sites are indicated. SD: Shine Dalgarno sequence complementary to *L. lactis* 16S rRNA, ATG: translation initiation codon served by SD.

Thus, in one embodiment, the invention relates to detoxified immunogenic derivatives of *Clostridium perfringens* β-toxin or an immunogenic fragment thereof, carrying at least one mutation in its amino acid sequence not found in wild-type β-toxin.

An immunogenic fragment thereof is understood to be a fragment that, although not comprising the full length amino acid sequence of the derivative of the β-toxin, still comprises those regions of the derivative that are capable of inducing a protective immune response in the host animal.

A mutation is understood to be a change in the amino acid sequence of the derivative β-toxin in comparison to the amino acid sequence of the wild-type β-toxin. The mutation is a substitution, deletion, insertion or inversion, or a combination thereof. A mutation can e.g. be such that one or more amino acids of the β-toxin are replaced by other amino acids, with different characteristics. A suitable replacement is e.g. the replacement of a negatively charged amino acid by a positively charged one, such as the replacement of Aspartate by Lysine. Another suitable replacement is that of an aromatic amino acid by an alifatic one: e.g. Tryptophan→Glycine. Also the replacement of a hydrophobic amino acid by a hydrophilic one, such as e.g. Isoleucine by Aspartate is suitable.

Therefore the invention in a preferred form relates to derivatives of β-toxin according to the invention, wherein at least one mutation is a replacement mutation.

It is clear that next to replacement, mutations involving the insertion and/or deletion of one or more amino acids providing non-toxic derivatives of β-toxin still capable of inducing immunological response are also part of the invention. Therefore, in an equally preferred form, the invention relates to derivatives of β-toxin according to the invention, wherein at least one mutation is a deletion or insertion.

When two or more mutations are made, combinations of replacement and deletion/insertion mutations are equally possible.

A derivative of β-toxin is considered non-toxic if its LD50 (lethal dose killing 50% of all animals in an experiment) in mice is at least ten times higher than the LD50 of native β-toxin. The LD50 of native β-toxin is about 0.15 μg/mouse.

As mentioned, it is one of the merits of this invention that, contrary to what was assumed in the art, it was found to be possible to genetically alter the amino acid sequence of the β-toxin such that a non-toxic and still immunogenic toxoid was obtained. Not all mutations will however lead to the desired non-toxic and still immunogenic derivatives of β-toxin. Therefore, a test for rapid screening and selection of mutants producing a non-toxic derivative of β-toxin that is still immunogenic has been developed. This test allows screening of large numbers of mutants producing non-toxic and still immunogenic derivatives of β-toxin. This test will be disclosed below.

It was also found that preferably those regions that form a transition domain between neutral and hydrophilic parts of the β-toxin are suitable as target regions for introducing mutations giving non-toxic derivatives of β-toxin with the desired characteristics. These regions can easily be traced by applying the Hopp-Woods algorithm to the sequence of the β-toxin (Hopp and Woods; Proc. Natl. Acad. Sci. 78: 38248-3828 (1981)). Therefore, in a more preferred form of this embodiment, the invention relates to derivatives of β-toxin having a mutation that is located in a transition domain between neutral and hydrophilic parts of the β-toxin.

Regions that are very suitable as target regions for mutations are located at position 62, at position 182, at position 197, between amino acid numbers 80-103, 145-147, 281-291, 295-299 relative to the peptide leader methionine and the region downstream of the unique cysteine at amino acid position 292.

Therefore, in an even more preferred form, the invention relates to derivatives of β-toxin having a mutation that is located in at least one of the regions at positions 62, 182, 197 and between amino acid numbers 80-103, 145-147, 281-291, 295-299 and/or the region downstream of amino acid position 292 relative to the peptide leader methionine. In a still even more preferred form, the mutations are located at position 62, at positions 80-82, at positions 95-97, at positions 101-103, at positions 145-147, at position 182, at position 197, at positions 287-291, at positions 295-299.

Non-toxic immunogenic derivatives of β-toxin according to the invention can be made by chemically replacing or modifying amino acids in the protein. They can also be made by introducing mutations in the gene encoding the β-toxin. Methods for introducing mutations in DNA fragments are described below. The mutated DNA fragments can then e.g. be cloned in a nucleotide sequence such as a suitable expression plasmid and subsequently be expressed.

Therefore, in another embodiment, the invention relates to nucleotide sequences comprising a mutated DNA fragment that has as a characteristic that it encodes a genetically detoxified immunogenic derivative of *Clostridium perfringens* β-toxin according to the invention or an immunogenic fragment thereof.

As mentioned above, in a preferred form of this embodiment, the invention relates to derivatives of β-toxin having a mutation that is located in a transition domain between neutral and hydrophilic parts of the β-toxin. Such a derivative of β-toxin can be made by expressing a DNA fragment encoding such a derivative of β-toxin. Therefore, in a preferred form the mutated DNA fragment encoding the derivative of β-toxin has a mutation in at least one DNA region encoding a transition domain between neutral and hydrophilic parts of the derivatives of β-toxin.

The detoxified immunogenic derivatives of *Clostridium perfringens* β-toxin according to the invention can e.g. be obtained by means of random mutagenesis of the gene encoding the β-toxin. Many ways of inducing random mutagenesis are known in the art, such as e.g. chemically induced mutagenesis using mutagenising chemical agents, mutagenesis by U.V.-radiation or γ-radiation or random mutagenesis using recombinant DNA technology.

Mutations at the DNA level can also be made at specific sites: site-directed mutagenesis. This is done with the help of known genetic engineering techniques. It is e.g. possible to use restriction enzymes to cut out DNA fragments in or encompassing the target regions, and to replace these fragments by synthetic fragments having a mutated sequence. Site-directed mutagenesis is also a very convenient technique for introducing mutations in the target regions.

If the mutation concerns a replacement mutation, the reading frame will of course remain unaltered. A combination of deletion and/or insertion mutations and replacement mutations is also possible.

The DNA mutation techniques described above are well-known in the art and have been described i.a. in Maniatis, Molecular Cloning, Cold Spring Harbor Laboratory Press, ISBN 0-87969-309-6 (1989).

A suitable bacterial expression system for expressing the derivatives of β-toxin according to the invention is the *Clostridium perfringens* bacterium itself. The native β-toxin gene can easily be replaced by the mutated DNA fragment encoding the derivatives of β-toxin according to the invention using homologous recombination. Homologous recombination is a technique well-known in the art.

The thus obtained recombinant *Clostridium perfringens* bacterium then produces the genetically detoxified immunogenic derivative of *Clostridium perfringens* β-toxin according to the invention.

Therefore, in still another embodiment, the invention relates to *Clostridium perfringens* bacteria comprising a nucleotide sequence with a mutated DNA fragment as described above.

Several additional problems are, however, encountered during the isolation of both toxic and genetically altered non-toxic derivatives of *Clostridium perfringens* β-toxin from *Clostridium perfringens*. First of all, Clostridium is a dangerous bacterium to grow, seen from a workers' health point of view. Growth of Clostridium species for the production of β-toxin must take place under high safety conditions, which makes large scale production difficult. Secondly, as mentioned before, together with the β-toxin several other major/minor toxins are made. Isolation and purification of the β-toxin amongst these other toxins, as is e.g. necessary for vaccine production, is difficult and time-consuming. Thirdly, Clostridium species are spore-forming bacteria. It is necessary but difficult to eliminate all spores from the β-toxin preparation and at the same time retain the immunogenic characteristics of the β-toxin, since these spores are highly resistant against heat and chemicals.

Therefore, there clearly is a need for methods to provide β-toxin free from other Clostddium-toxins and free from Clostridium spores.

Non-Clostridium expression systems based on the Gram negative bacterium *E. coli* for the expression of Clostridium β-toxin have been described before. *E. coli* systems have been used by Hunter et al. (Infect. & Immun. 61: 3958–3965 (1993)) for the expression of the β-toxin gene. Only a minor band corresponding to the expected 34 kD protein was found whereas by far most of the β-toxin protein was found in large 118 kD multimeric forms. Steinporsdottir et al. (FEMS Microbiology Letters 130: 273–278 (1995)) tried to express the β-toxin gene in *E. coli* as a fusion protein fused to gluthatione S-transferase. They also, like Hunter, found only high molecular weight non-natural β-toxin. It was concluded in this paper that the protein produced in *E. coli* had a conformation different from the native β-toxin. It therefore seems likely that other Clostridium-encoded proteins play an additional role in the conformational folding and excretion of the native β-toxin. This is known to be the case for many other excreted bacterial proteins. For this reason, since as mentioned above there is a delicate balance between structure and immunogenicity, β-toxin obtained from sources other than *Clostridium perfringens* and thus in a non-native form cannot be expected to be an efficient basis for a vaccine, regardless the expression system used.

It was surprisingly found now that expression of the native β-toxin gene in Gram positive bacteria other than *Clostridium perfringens* provides a native β-toxin with all the biological and biophysical characteristics and activities of the native β-toxin as produced in *Clostridium perfringens*, but having several highly desirable advantages over the β-toxin produced in *Clostridium perfringens* or *E. coli*: a) it is not contaminated with *Clostridium perfringens* spores, b) it is produced free of contaminating lipopolysaccharides, c) it is produced free of other major/minor Clostddium toxins and d) it is in it's native conformation. A thus obtained β-toxin can be inactivated with formalin more advantageously than the β-toxin obtained from Clostridium, since the only biological material to be taken into consideration during inactivation is the β-toxin itself: spores, lipopolysaccharides and other major/minor Clostridium toxins need not be taken care of, since they are absent per se.

Therefore, in still another embodiment, the invention relates to a Gram positive bacterial expression systems wherein the Gram positive bacterium is not *Clostridium perfringens*, the said expression system comprising the gene encoding wild-type *Clostridium perfringens* β-toxin.

The β-toxin gene can be under the control of its native promotor. It may also be placed under the control of a heterologous promotor. Such a promotor can be e.g. the Lac-promotor (Chang et al., Nature 275: 615 (1978)) or the Trp-promotor (Goeddel et al., N.A.R. 8: 4057 (1980)). Such a promotor may be a strong promotor, leading to over-expression of the β-toxin, or it may be an inducible promotor. Both kinds of promoters are known in the art.

Several expression systems for Gram positive bacteria have been described, and versatile expression plasmids for use in several families of Gram positive bacteria are known in the art. As an example may serve expression systems based upon the Enterococcal broad Gram positive host range replicon of pAMβ1 described by Simon and Chopin (Biochimie 70: 559–567 (1988)). Derivatives of this plasmid can be used for expression of foreign genes in e.g. Streptococcus, Lactobacillus, and Bacillus species.

Within the group of non-Clostridium Gram positive bacteria, those bacteria of which the genome has a relatively high AT-content are most suitable for cloning and expression of genes from the genus Clostridium. Therefore, in a more preferred form, the Gram positive bacterium used for the preparation of the native β-toxin or the derivative of β-toxin according to the present invention is selected from the group of Lactococcus, Lactobacillus, Leuconostoc, Pediococcus, Streptococcus, Enterococcus, Staphylococcus, Bacillus, Sarcina, Ruminococcus or Listeria.

It is of course even more advantageous to express a mutated β-toxin gene according to the invention in a Gram positive bacterium other than Clostridium: in that case the detoxification treatment with formalin can be completely omitted. The so-obtained non-toxic derivative of β-toxin has, next to being free from spores, free from lipopolysaccharides, free of other major/minor Clostridium toxins and being in a native form, the additional advantage that it is non-toxic per se.

Therefore, in a more preferred form, the invention relates to a Gram positive bacterial expression system, said Gram positive bacterium not being *Clostridium perfringens*, comprising a nucleotide sequence encoding a derivative β-toxin gene according to the invention or an immunogenic fragment thereof.

Still another embodiment of the present invention relates to vaccines for combating *Clostridium perfringens* infections, based upon genetically detoxified immunogenic derivatives of *Clostridium perfringens* β-toxin. Such vaccines can be made e.g. by admixing an immunologically sufficient amount of detoxified immunogenic derivatives of *Clostridium perfringens* β-toxin according to the invention and a physiologically acceptable carrier. An immunologically sufficient amount is understood to be the amount of detoxified immunogenic *Clostridium perfringens* β-toxin that is capable of inducing a protective immune response in a host animal.

Thus still another embodiment of the invention relates to vaccines for combating *Clostdidium perfringens* infection that comprise a derivative of *Clostridium perfringens* β-toxoid according to the invention or an immunogenic fragment thereof, and a physiologically acceptable carrier.

A physiologically acceptable carrier is e.g. water or a physiological salt solution. Often the vaccine is additionally mixed with stabilisers, e.g. to protect degradation-prone polypeptides from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates. It goes without saying that other ways to stabilise the vaccine by adding compounds are also embodied in the present invention.

Optionally, one or more compounds having adjuvant activity may be added to the vaccine. Adjuvantia are non-specific stimulators of the immune system. They enhance the immune response of the host to the administered immunogens. Therefore, in a more preferred form, the vaccines according to the present invention comprise an adjuvant. Examples of adjuvantia known in the art are Freunds Complete and Incomplete adjuvants, vitamin E, non-ionic block polymers, muramyldipeptides, ISCOMs (immune stimulating complexes, cf. for instance European Patent EP 109942), Saponins, mineral oil, vegetable oil, and Carbopol (a homopolymer).

Adjuvantia, specially suitable for mucosal application are e.g. the *E. coli* heat-labile toxin (LT) or Cholera toxin (CT).

Other suitable adjuvants are for example aluminium hydroxide, phosphate or oxide, oil-emulsions (e.g. of BAYOL F or MARCOL 52, saponins or vitamin-E solubilisate.

The vaccine according to the present invention can be kept in storage using methods known in the art for storing live vaccines. Storage can e.g. be done at sub-zero temperature.

Freeze-drying also is a known and suitable method for the conservation of vaccines. Freeze-drying has the advantage that it stabilises the vaccine so that it can be kept in stock at temperatures well above those necessary to keep non-freeze-dried stocks. The vaccine according to the present invention can be freeze-dried very efficiently, especially when it is mixed with stabilisers such as those mentioned above before freeze-drying.

The vaccine can be administered to all hosts sensitive to *Clostridium perfringens* type B or C infection, such as man, lamb, sheep, goat, pig, bird and calf.

The vaccine can be administered as early as day of birth, but can also be given at any later stage.

Vaccine doses are preferably between 1 and 100 μg of the derivative per animal, depending partially on the size of the animal. For e.g. pigs, a very suitable dosis ranges between 20 and 80 μg.

Although in principle all common routes of administration can be used, the vaccine is preferably administered intraperitoneally, intranasally, intramuscularly, subcutaneously, orally or intradermally.

Still another embodiment of the invention relates to an alternative way of making a vaccine for combating *Clostridium perfringens* infections. Attenuated or non-pathogenic live bacteria and viruses having a *Clostridium perfringens* type B or C sensitive human or animal as a host, can be used as carriers of the mutated β-toxin gene according to the invention as described above. These so-called live recombinant carrier vaccines can be safely administrated to the host-animal together with a physiologically acceptable carrier; they behave non-pathogenically and they express a non-toxic derivative of the β-toxin. The live recombinant carrier-based vaccines have the advantage that they produce and or present derivatives of the *Clostridium perfringens* β-toxin directly in the host. Animals vaccinated with such a recombinant bacterium or virus will produce an immunogenic response not only against the immunogens of the vector, but also against the immunogenic parts of the polypeptide(s) for which the genetic code is additionally cloned into the recombinant carrier. This has the advantage that by administrating such a recombinant carrier protection against two or more diseases can be obtained.

Many live recombinant carrier viruses and bacteria are currently known in the art. Suitable live recombinant carrier bacteria are e.g. Salmonella species and *E. coil* species. Viruses frequently used in the art as live recombinant carriers are adenoviruses, retroviruses, vaccinia viruses and herpesviruses. Also suitable as a specific orally applicable carrier virus is Porcine Parvovirus. Another virus that is useful as a live recombinant carrier virus for carrying the gene encoding the β-toxoid is the herpesvirus, Pseudorabies virus (PRV) (e.g. as described in European Pat. No. 606.437). Such a PRV carrying the β-toxoid gene would protect pigs against infection with both PRV and *Clostridium perfringens* type C.

Thus, vaccines for combating *Clostridium perfringens* infection that comprise a live recombinant carrier organism carrying the mutated β-toxin gene according to the invention are therefore also part of the invention.

It is clear that the native β-toxin is an important, if not the most important virulence factor in *Clostridium perfringens*. Therefore, a Clostridium strain in which the native β-toxin gene is replaced by a mutant β-toxin gene according to the invention as described above has therefore lost an important virulence factor. Such a strain can be used as a live attenuated vaccine, since the β-toxin is not made in its toxic form but in the form of a non-toxic derivative. The advantage of such a live attenuated vaccine is that it produces a non-toxic but still immunogenic form of the β-toxin, whereas it has in addition all the other immunogenic antigens of the native *Clostridium perfringens* strain.

Therefore, vaccines comprising a live attenuated *Clostridium perfringens* strain in which the native β-toxin gene is replaced by a mutated β-toxin gene according to the invention are also included in this invention.

Also embodied in the invention are vaccines that comprise, in addition to a β-toxin derivative according to the invention, immunogens from other pathogens. This allows one to vaccinate against various diseases in one vaccine administration step.

In a more preferred form of this embodiment, the vaccine according to the present invention comprises additional immunogens, selected from the group consisting of *Actinobacillus pleuropneumoniae*, Pseudorabies virus, Porcine Influenza virus, Porcine Parvovirus, Transmissible Gastroenteritisvirus, rotavirus, *Escherichia coli, Erysipelothrix rhusiopathiae, Pasteurella multocida, Bordetella bronchiseptica*, Salmonella species, *Mycoplasma hyopneumoniae, Haemophilus parasuis* and Helicobacter-like bacteria.

The present invention also relates to methods for the preparation of native *Clostridium perfringens* β-toxin, which methods are based upon the expression of a nucleotide sequence comprising a DNA fragment encoding said β-toxin in Gram positive bacteria other than *Clostridium perfringens*.

Furthermore, the invention presents methods for the preparation of non-toxic derivatives of *Clostridium perfringens* β-toxin according to the invention. These methods are based upon the expression of nucleotide sequences comprising a DNA fragment encoding a derivative of β-toxin, in a Gram positive bacterium.

Also, the invention provides methods for the preparation of a vaccine for combating *Clostridium perfringens* infection. Such methods e.g. comprise admixing a derivative of *Clostridium perfringens* β-toxin according to the invention and a physiologically acceptable carrier.

EXAMPLE 1

Construction of Expression Plasmids pKS90, pTREX1A, pTREX7 and pTREX14

The pKS90 plasmid is a high-copy number (40–80 per cell) theta-replicating gram positive plasmid based on the pTREX1 plasmid, which is itself a derivative of the previously published plL253 plasmid. plL253 incorporates the broad Gram-positive host range replicon of pAMb1 (Simon, D., and A. Chopin. 1988. Construction of a vector plasmid family and its use for molecular cloning in *Streptococcus lactis*. Biochimie. 70: 59–567.) and is non-mobilisable by the *L. lactis* sex-factor. plL253 also lacks the tra function which is necessary for transfer or efficient mobilisation by conjugative parent plasmids exemplified by plL501. The Enterococcal pAMb1 replicon has previously been transferred to various species including Streptococcus, Lactobacillus and Bacillus species as well as *Clostridium acetobutylicum*, (Gibson, E. M., N. M. Chace, S. B. London and J. London. 1979. J. Bacteriol. 137: 614619. LeBlanc, D. J., R. J. Hawley, L. N. Lee and E. J. St. Martin. 1978. Proc. Natl. Acad. Sci. USA. 75:3484–3487. Oultram, J. D., and M. Young. 1985. FEMS Micro. Lett. 27: 129–134.) indicating the potential broad host range utility. While pTREX1 (and pTREX1A) represents a basic constitutive transcription vector, the derivative pKS90 utilises translational coupling to a lactococcal translational initiation region in order to increase expression level. Construction details of pKS90 and its immediate parent pTREX1 are given below.

pTREX1

Figures 1, 1B:
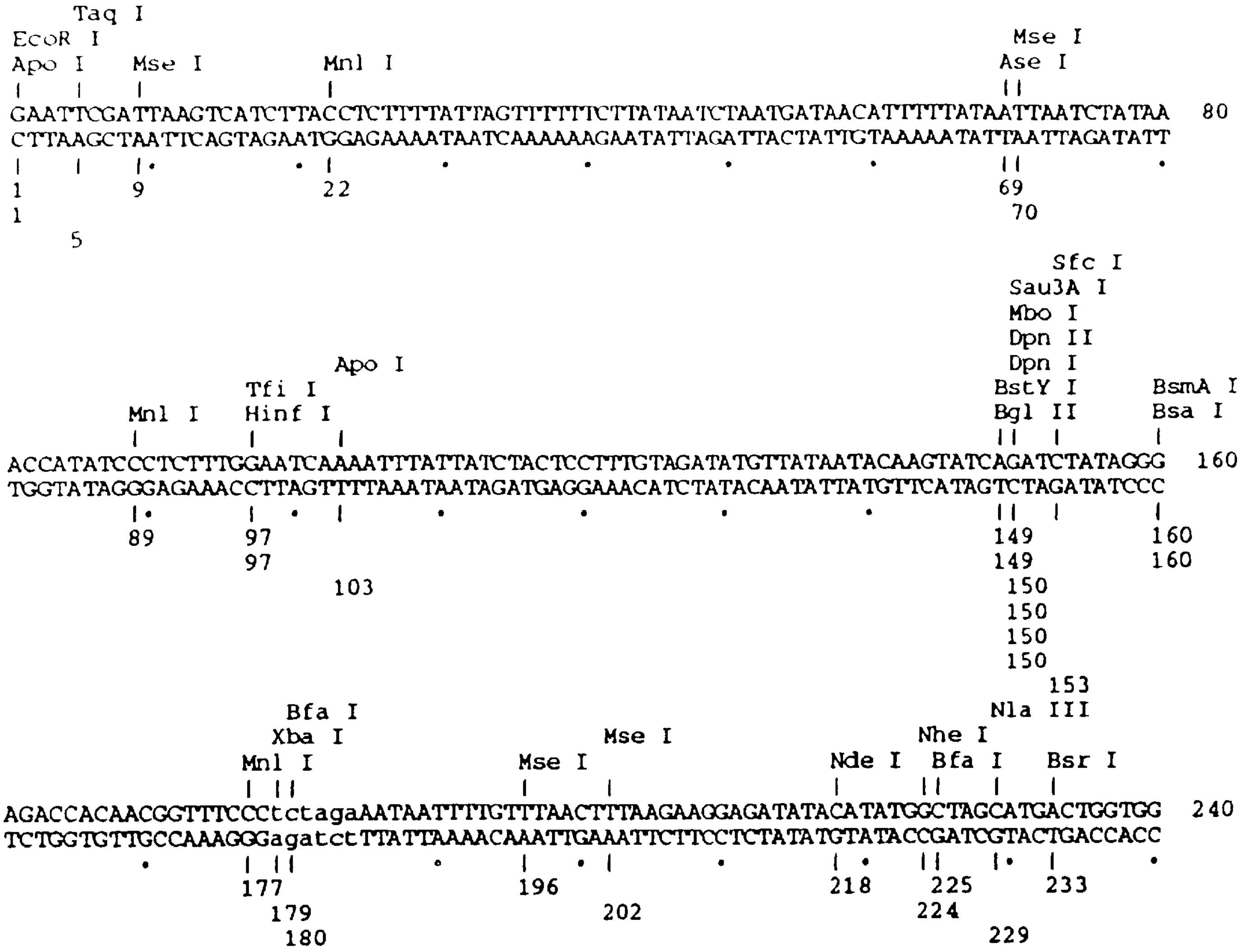
FIG. 1B: the complete pTREX1A sequence, including restriction enzyme positions.

An artificial DNA fragment containing a putative RNA stabilising sequence, a translation initiation region (TIR), a multiple cloning site for insertion of the target genes and a transcription terminator was created by annealing 2 complementary oligonucleotides and extending with Tfl DNA polymerase. The sense and antisense oligonucleotides contained the recognition sites for NheI and BamHI at their 5' ends respectively to facilitate cloning. This fragment was cloned between the XbaI and BamHI sites in pUC19NT7, a derivative of pUC19 which contains the T7 expression cassette from pLET1 (Wells, J. M., P. W. Wilson and R. W. F. Le Page. 1993. J. Appl. Bact. 74:629–636.) cloned between the EcoRI and HindIII sites. The resulting construct was designated pUCLEX. The complete expression cassette of pUCLEX was then removed by cutting with HindIII and blunting followed by cutting with EcoRI before cloning into EcoRI and SacI (blunted) sites of plL253 to generate the vector pTREX. The putative RNA stabilising sequence and TIR are derived from the *Escherichia coli* T7 bacteriophage sequence and modified at one nucleotide position to enhance the complementarity of the Shine Dalgarno (SD) motif to the ribosomal 16s RNA of *Lactococcus lactis*. A *Lactococcus lactis* MG1363 chromosomal promoter designated P1 was cloned between the EcoRI and BglII sites present in the expression cassette, creating pTREX1. This promoter had been previously isolated using the promoter probe vector pSB292 and characterised by primer extension and DNA sequencing analysis (Nick. R. Waterfield, R. W. F. Le Page, P. W. Wilson, and J. M. Wells. Gene. 165.1995. 9–15.). The promoter fragment was amplified by PCR using the Vent DNA polymerase. The PCR fragment included all of the DNA sequence upstream of the cloned promoter and up to 15 bases 3' to the transcription start site. The Shine-Dalgarno (SD) sequence present downstream of the transcription start site of this promoter was deliberately excluded from the PCR amplified promoter fragment to prevent translation initiation at sites other than the start codon indicated in the expression cassette. Two similar vectors designated pTREX7 and pTREX14 have also been created using the weaker P7 and P14 promoters, cloned between the EcoRI and BglII sites in place of P1. The PCR primers used to create these promoter fragments are illustrated in FIG. 1.*d*. The pTREX1A plasmid represents an alternative to pTREX1, in which the XbaI bounded expression cassette is replaced by a XbaI-SpeI T7-expression cassette fragment from pET3A. The SD sequence is therefore not optimised for Lactococcus. The complete pTREX1A sequence and schematics illustrating the expression cassette are illustrated in FIG. 1.

pKS90

Figures 1, 1B, 2:
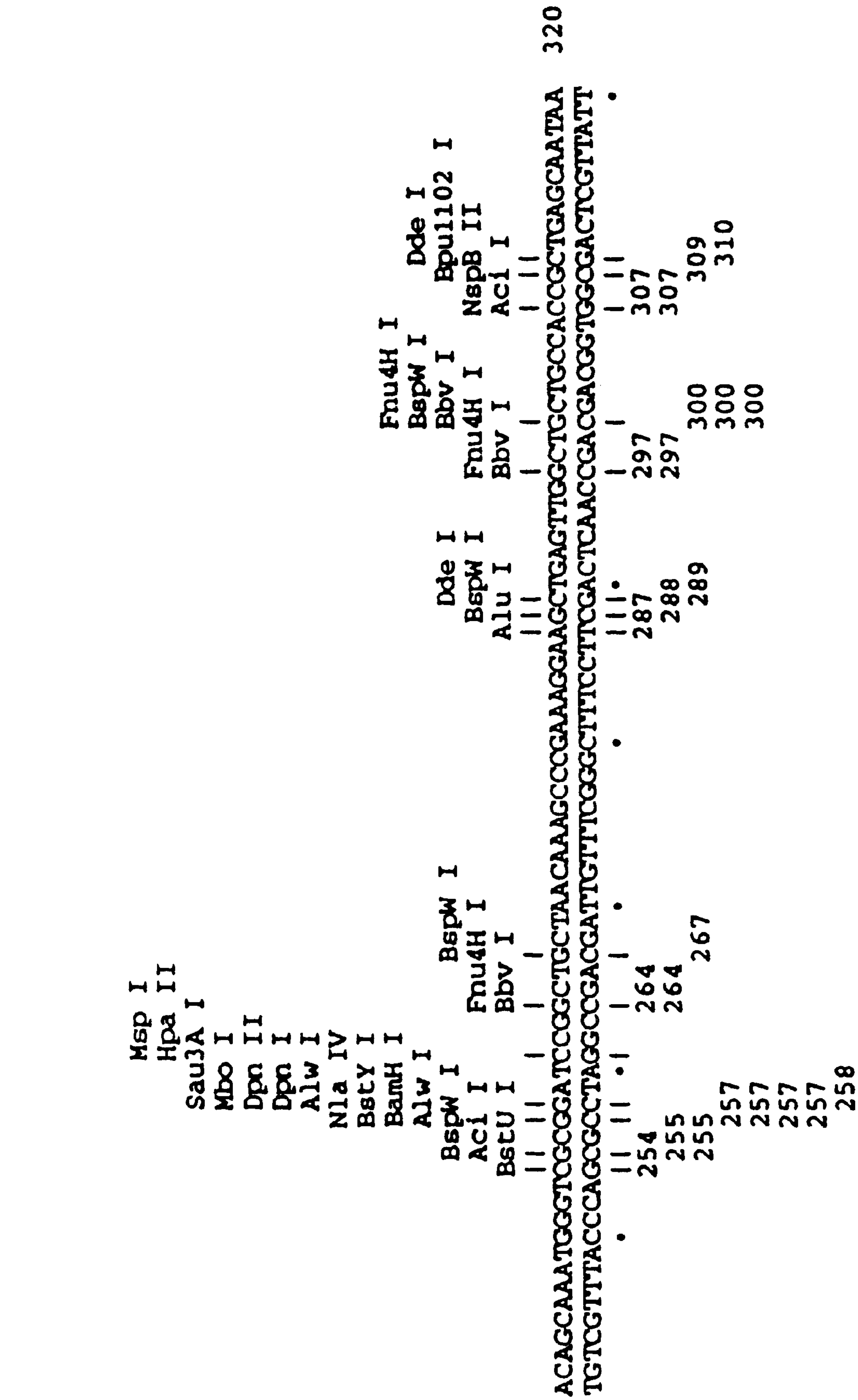

The pKS90 plasmid is a derivative of pTREX1, which while utilising the same transcription promoter P1, has a modified TIR containing the SD and first 20 codons of a lactococcal chromosomally derived resolvase gene, P11, (Nick. R. Waterfield, R. W. F. Le Page, P. W. Wilson, and J. M. Wells. Gene. 165. 1995. 9–15.). This was achieved by cloning an artificial DNA sequence, containing the new TIR, between the BglII and BamHI sites of pTREX1. The oligonucleotide sequences used in this procedure are presented in FIG. 2. Through the careful choice of PCR primer sequence, a PCR derived target gene can be translationally coupled to this TIR, which has been shown to increase expression level when compared to that obtained from the pTREX1 parent plasmid. The complete pKS90 sequence and a schematic illustrating the expression cassette are illustrated in FIG. 2.

Construction of Recombinant Strains of *Lactococcus lactis* Which Secrete Active Beta Toxin The pJF2000 DNA (as supplied by J. Frey, Institute for veterinary bacteriology, University of Berne, CH-3012 Berne, Switzerland) comprising a gene encoding the β-toxin as published by Hunter et al. (Infect. & Immun. 61: 3958–3965 (1993)) was electroporated into *E. coli* SURE. Plasmid DNA from six independent transformants was isolated, examined by restriction digest and pooled. These strains were stored at −70C in 15% glycerol. The cpb gene with associated translation initiation region (and upstream RNA stabilising stem-loop) was excised from this pooled preparation of plasmid DNA by digestion with BbaI/BamHI or SmaI/BamHI. The purified cpb gene fragments were ligated into the multiple cloning sites of the expression vectors pTREX1A, pTREX14 and pTREX7, which direct high, medium and low levels of constitutive expression respectively. BbaI/BamHI ended cpb fragments were ligated into BbaI/BamHI digested pTREX1ANEW while the SmaI/BamHI ended cpb fragment was ligated into BamHI/BglII (blunted) pTREX14 and pTREX7 DNA. These constructs were successfully electroporated into the specially disabled strain *Lactococcus lactis* pep5- acmA-, which lacks a chromosomally encoded peptidase, pep5, which enables the organism to utilise peptides liberated from casein. In addition it also lacks a cell wall associated autolysin, acmA. Any other *Lactococcus lactis* strain is however suitable for this purpose. Ten correct isolates of each type were identified using restriction digest analysis and have been stored at −70C in 15% glycerol. These strain types are designated *L. lactis* pep5- acmA- [pTREX1Acpb], *L. lactis* pep5- acmA- [pTREX14cpb] and *L. lactis* pep5-acmA- [pTREX7cpb]. In addition, the cpb gene was amplified by PCR using Vent DNA polymerase and BamHI ended oligonucleotides from plasmid pJF2000. This PCR product was cloned into the BamHI site of the TIR coupling vector pKS90.

Total protein extracted from mid-log cells and supernatant was resolved using SDS-PAGE before transferring to nitrocellulose filters. These filters were probed with both monoclonal and polyclonal antibodies to Cpb, using MAB (monoclonal antibody) purified beta-toxin as a control. A single protein product of the correct size (approximately 30 kDA) was detected in the culture supernatants from all four strains, by western blot and Coomasie Blue staining of SDS gels. The amount of beta toxin secreted by each strain was consistent with the relative strengths of the promoters in the expression vectors used. No intracellular toxin could be detected, suggesting that the clostridial export sequence functions efficiently in Lactococcus. Filtered supernantants from the pTREX1A expressor, *L. lactis* MG1363 pep5- acmA- [p3–1/5], and the pKS90 expressor *L. lactis* MG1363 pep5- acmA- [p5–123], were shown to contain active toxin, providing a positive control for the recombinant beta-toxin.

The cpb Mutant Genes

Figures 1, 1B, 2, 3, 4, 5, 6, 7:
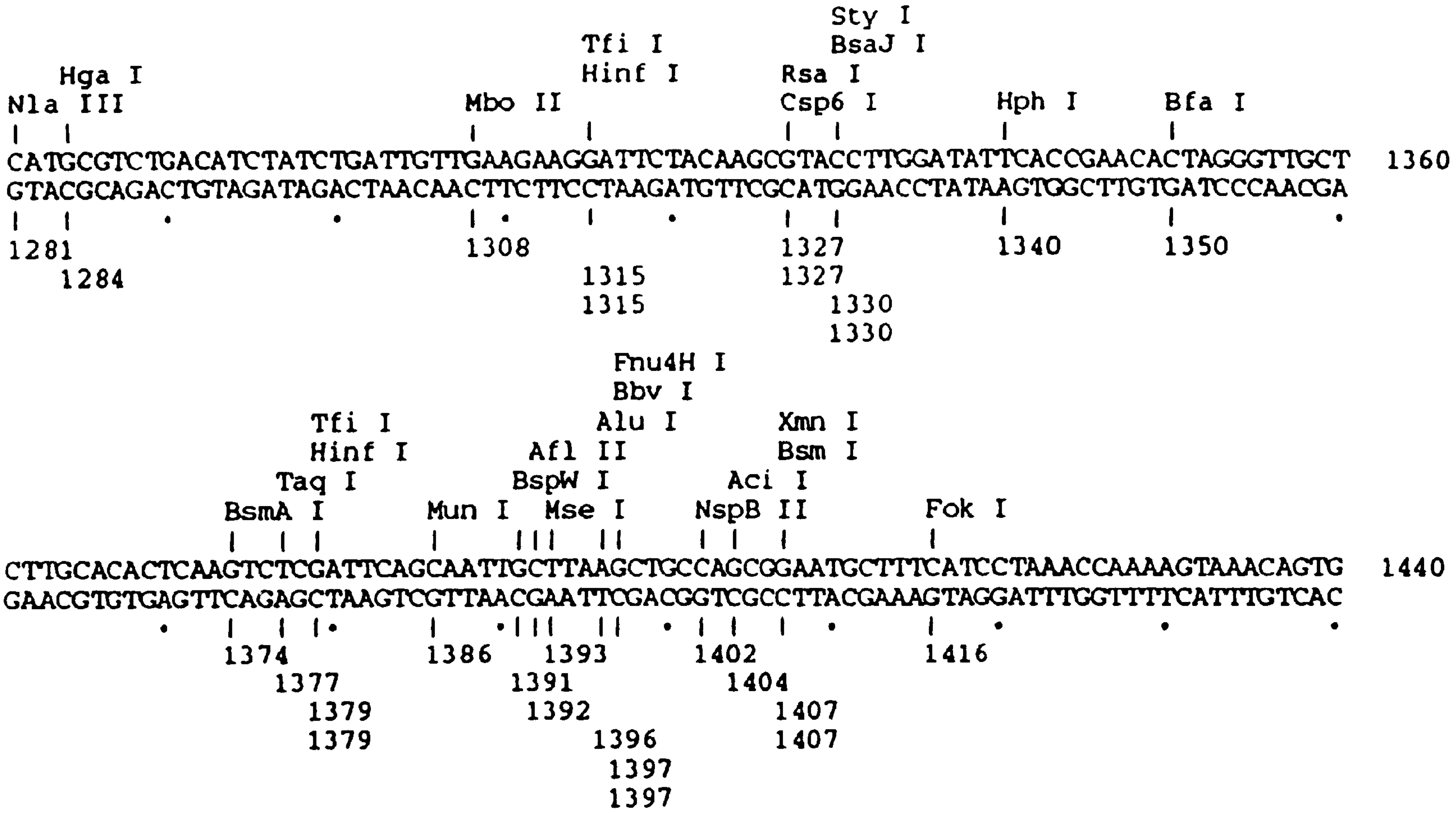
FIG. 4: Amino acid sequence of *Clostridium perfringens* β-toxin.
Figures 1, 1B, 2, 3, 4, 5, 6, 7, 8, 9:
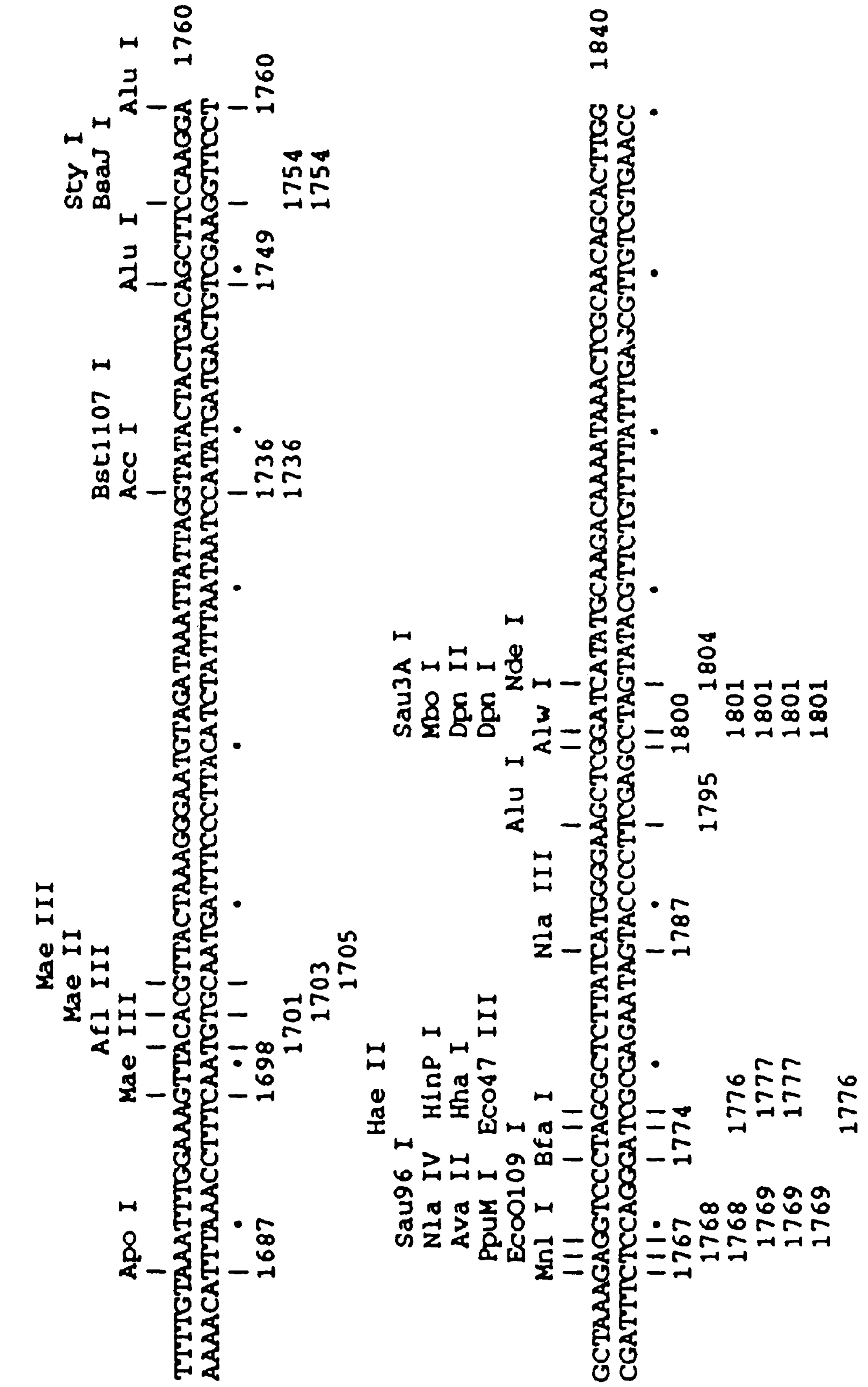
Figures 1, 1B, 2, 3, 4, 5, 6, 7, 8, 9, 10, 11:
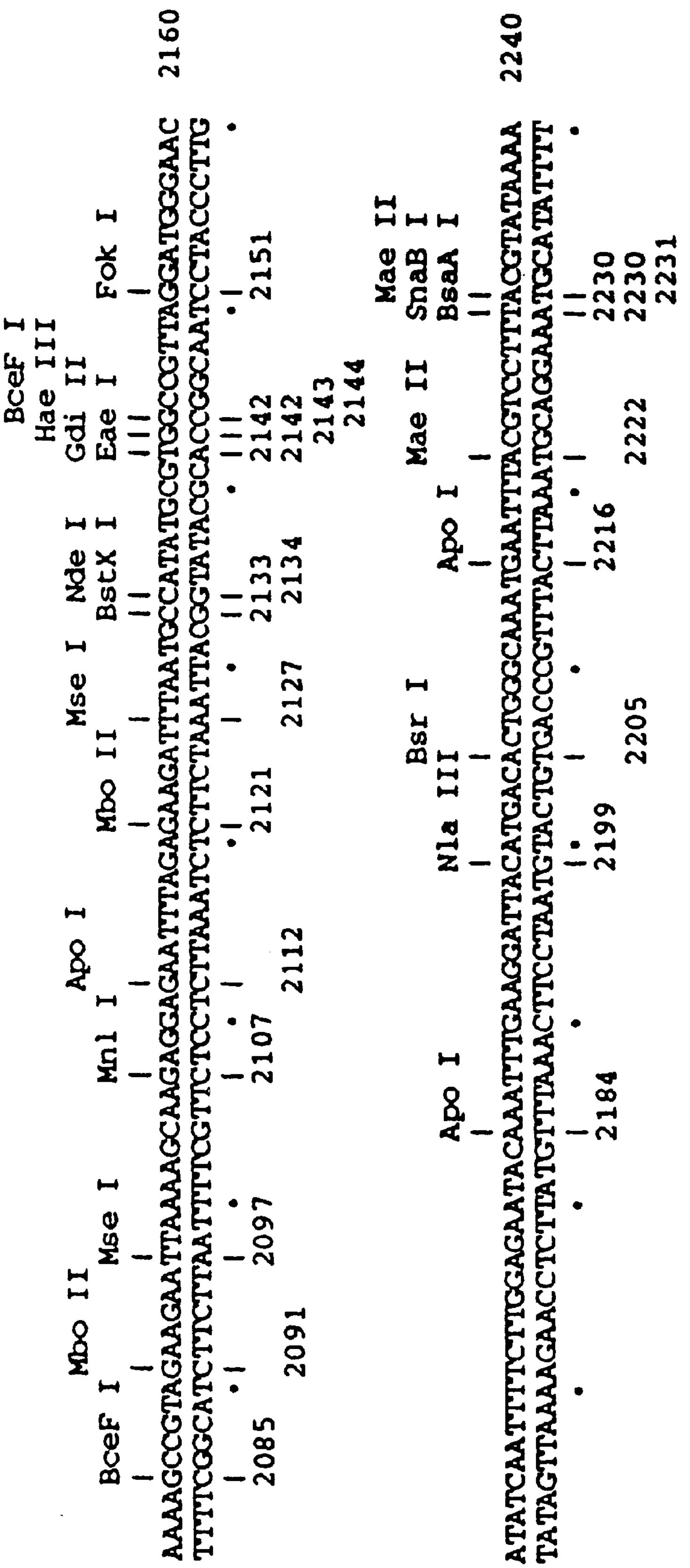
Figures 1, 1B, 2, 3, 4, 5, 6, 7, 8, 9, 10, 11, 12, 13, 14:
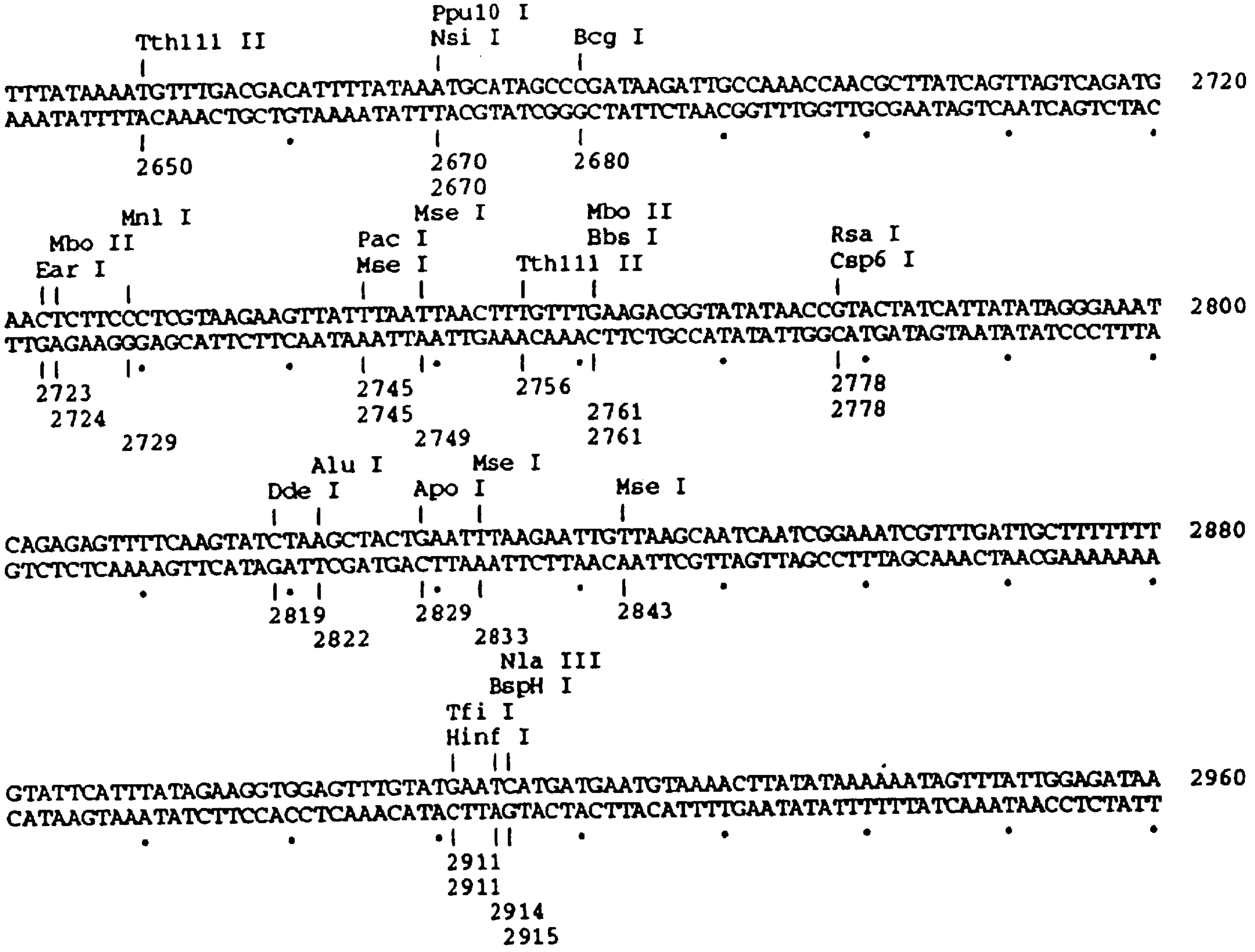
Figures 1, 1C:
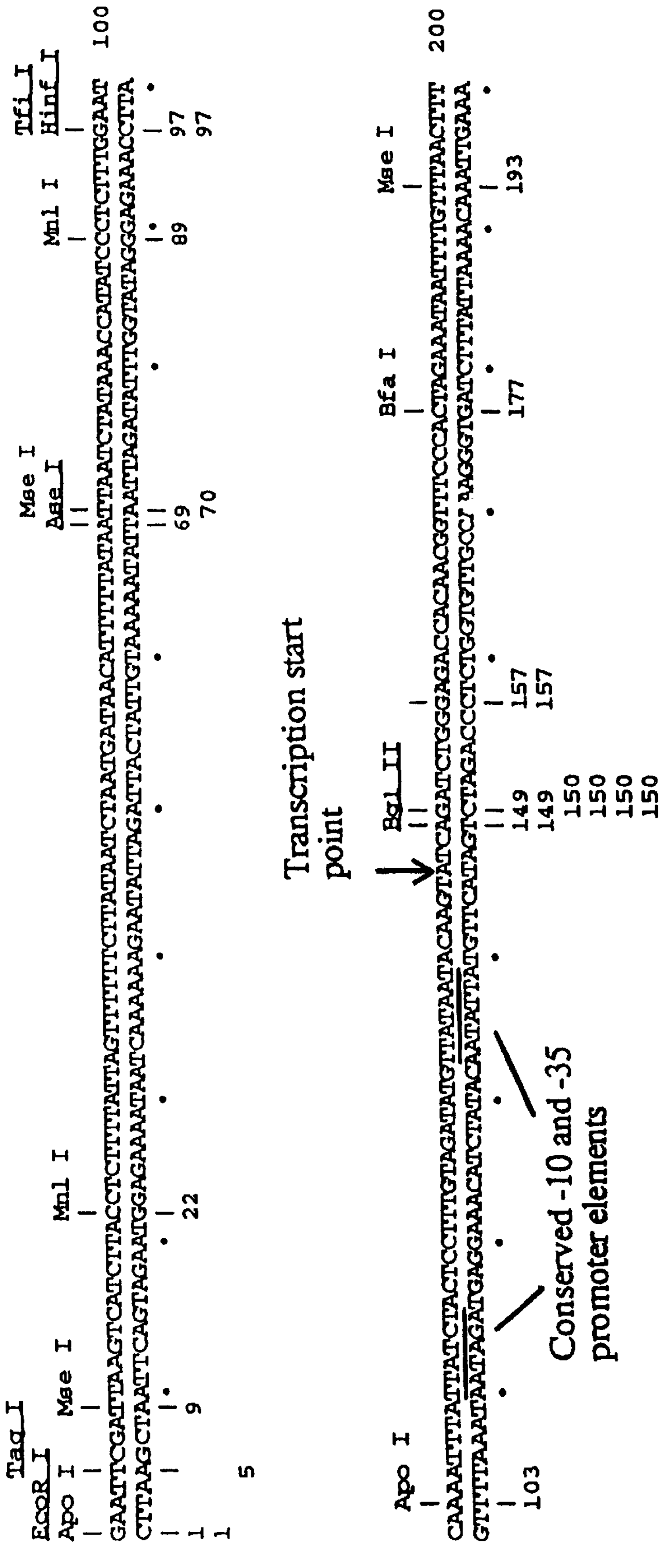
FIG. 1C: features of the highly similar pTREX1 expression cassette.
Figures 1, 1C, 2:
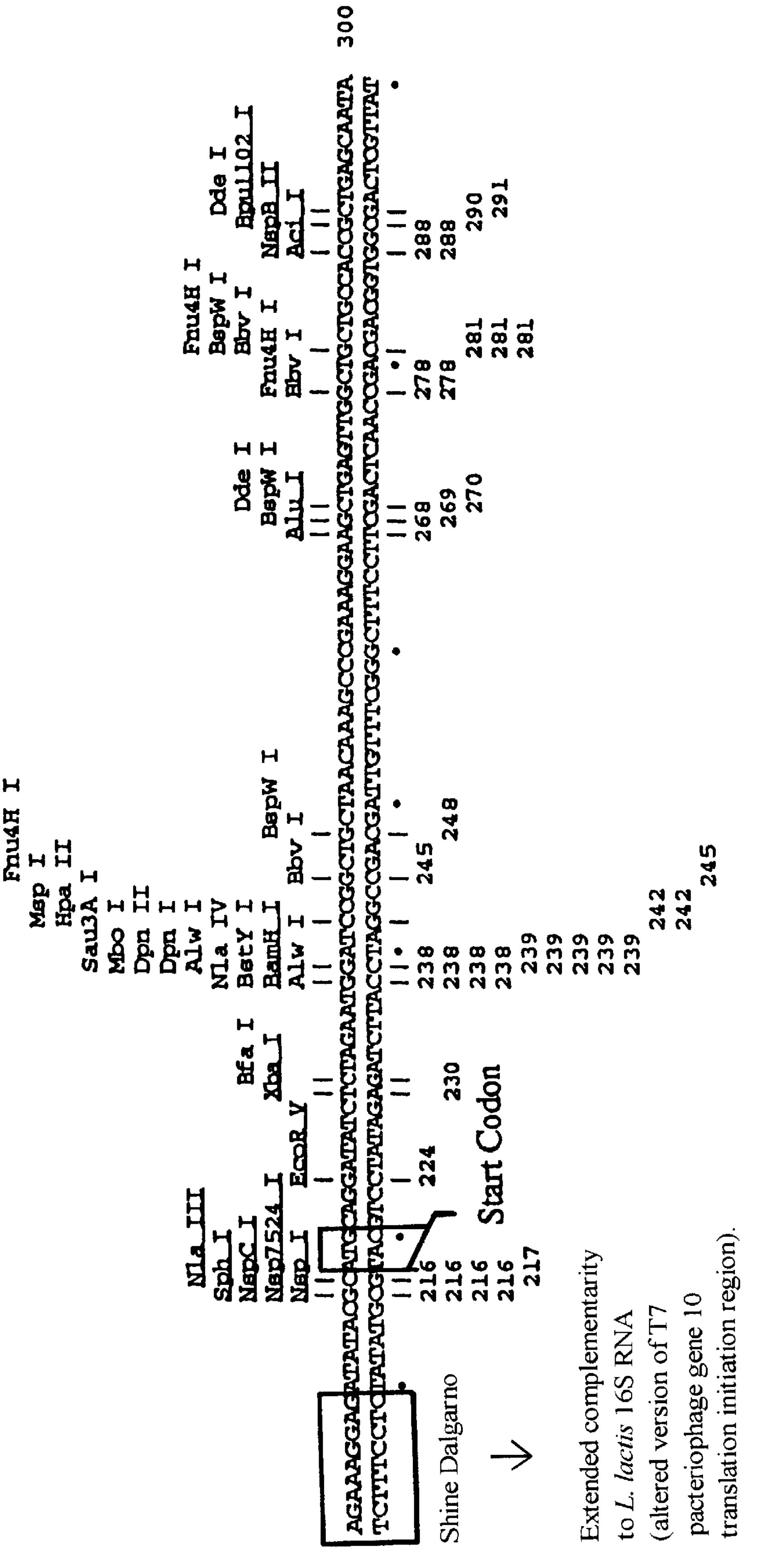
Figures 1, 1C, 2, 3:
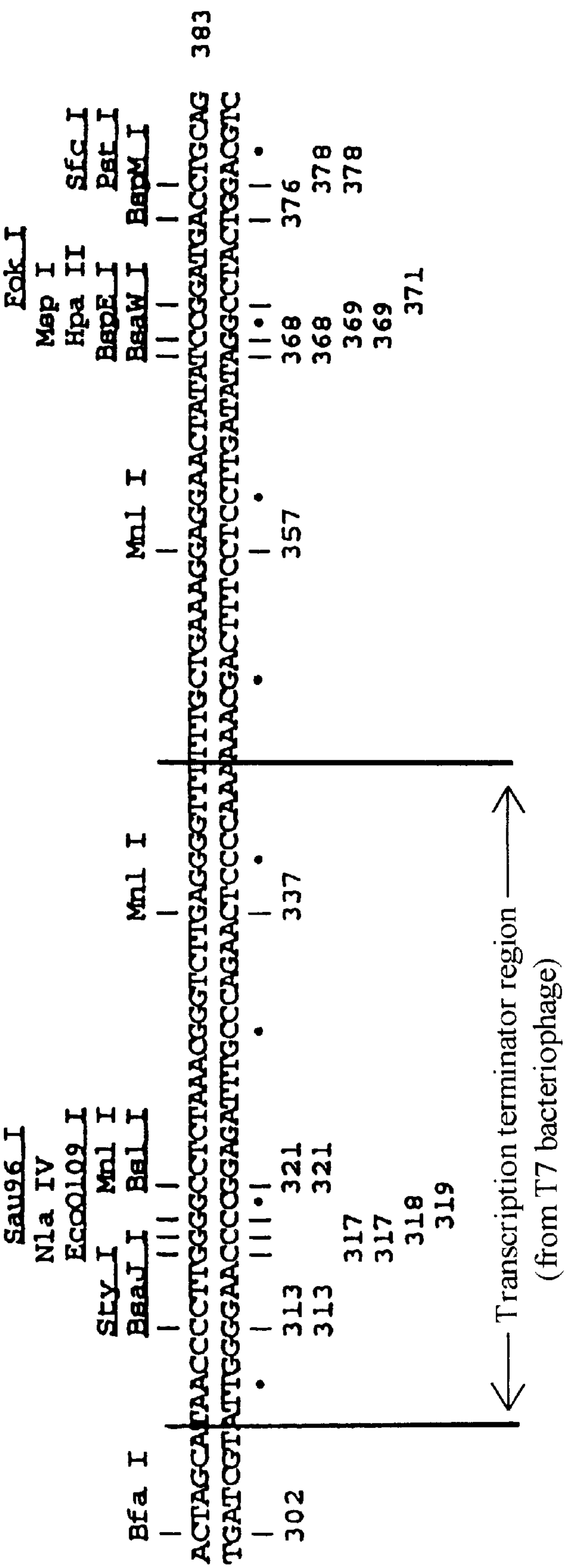
Figures 2, 2B:
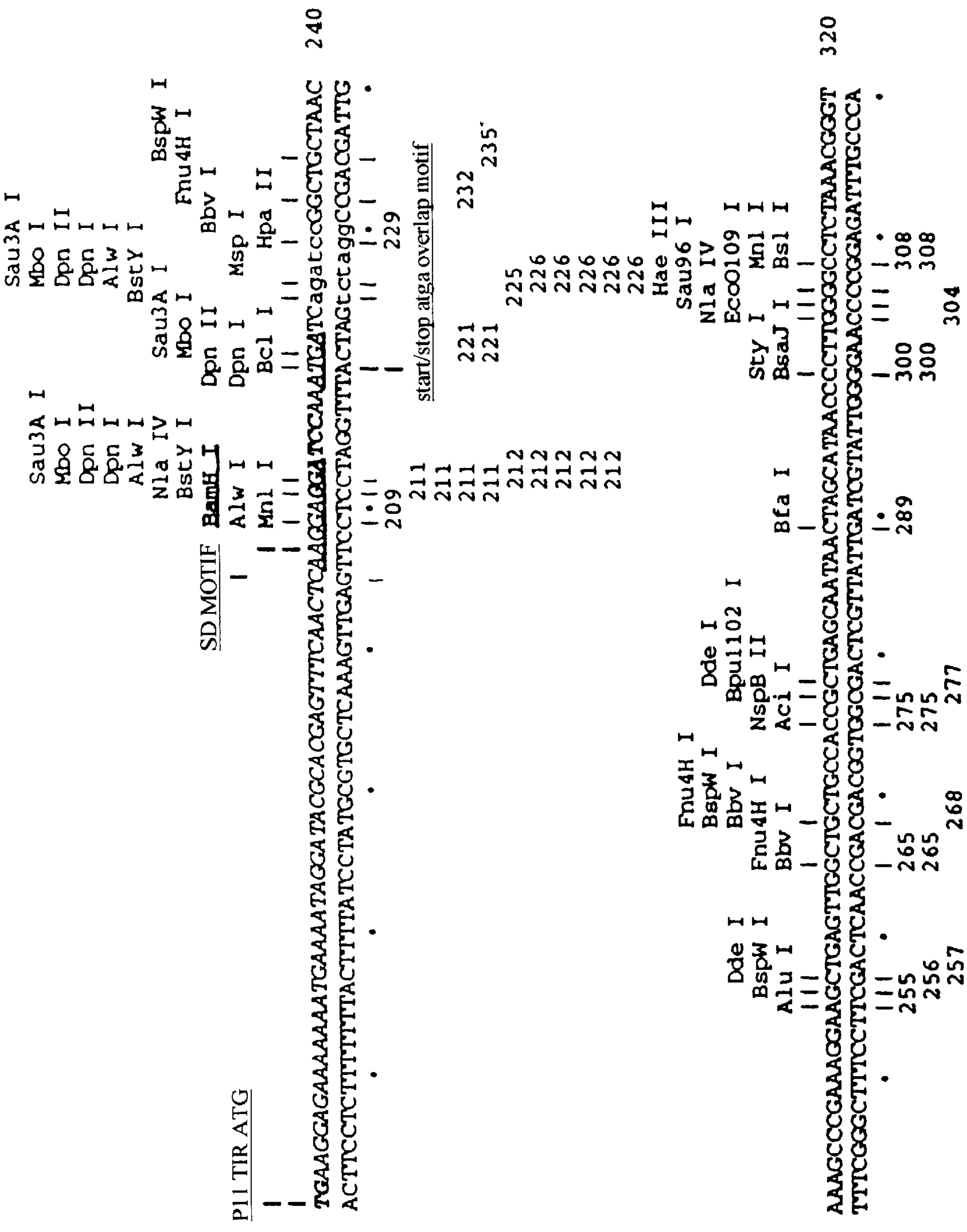
FIG. 2B: the complete pKS90 sequence, including restriction enzyme positions.
Figures 2, 2B, 3:
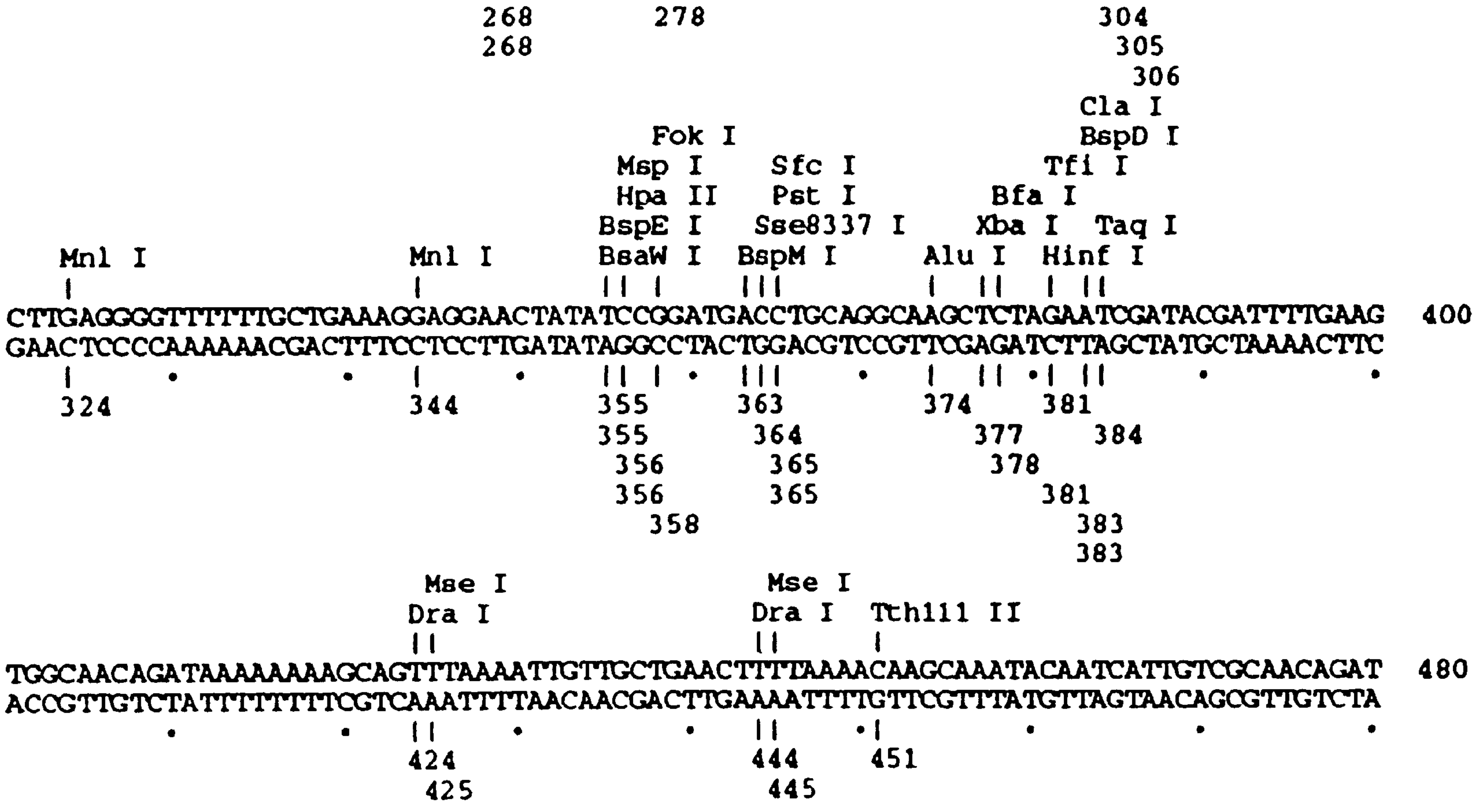
Figures 2, 2B, 3, 4:
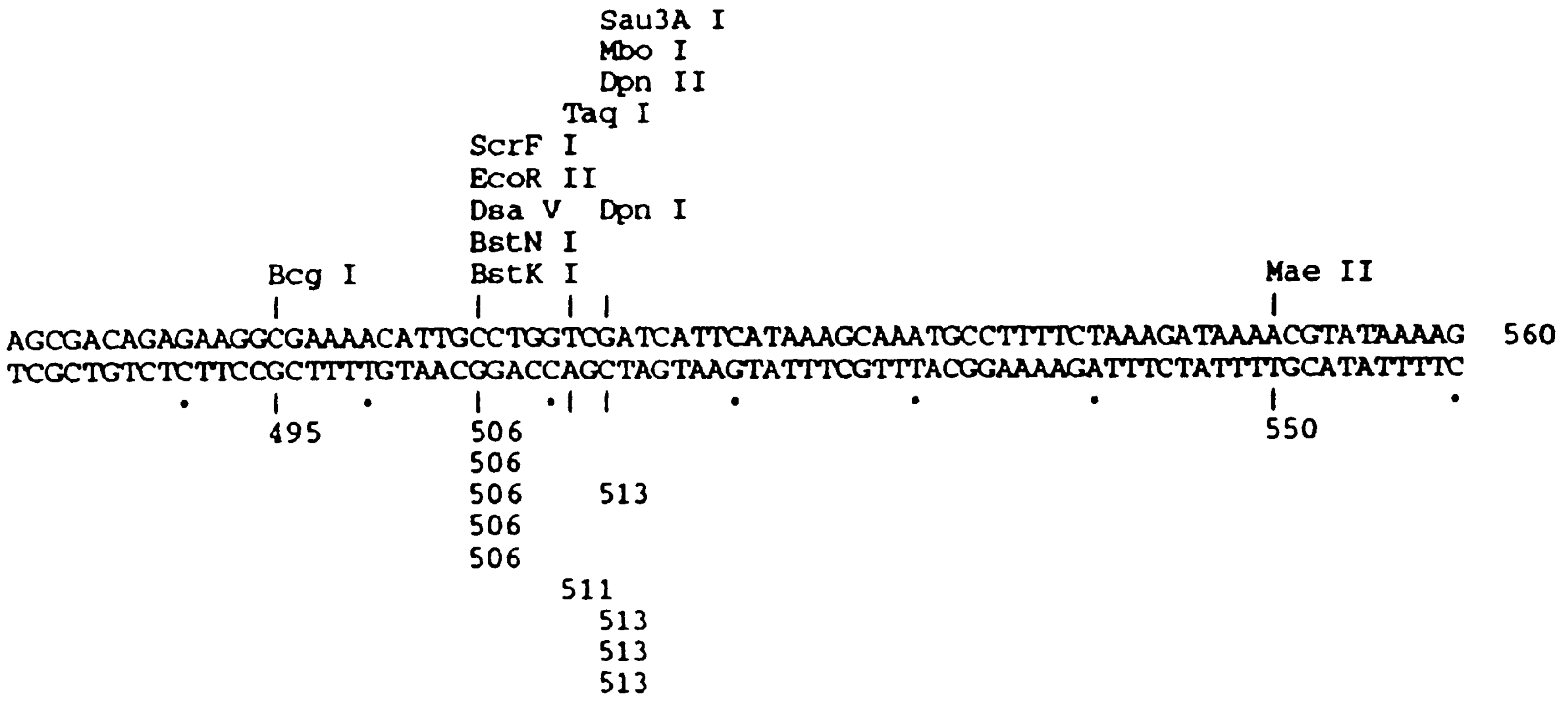
Figures 2, 2B, 3, 4, 5, 6:
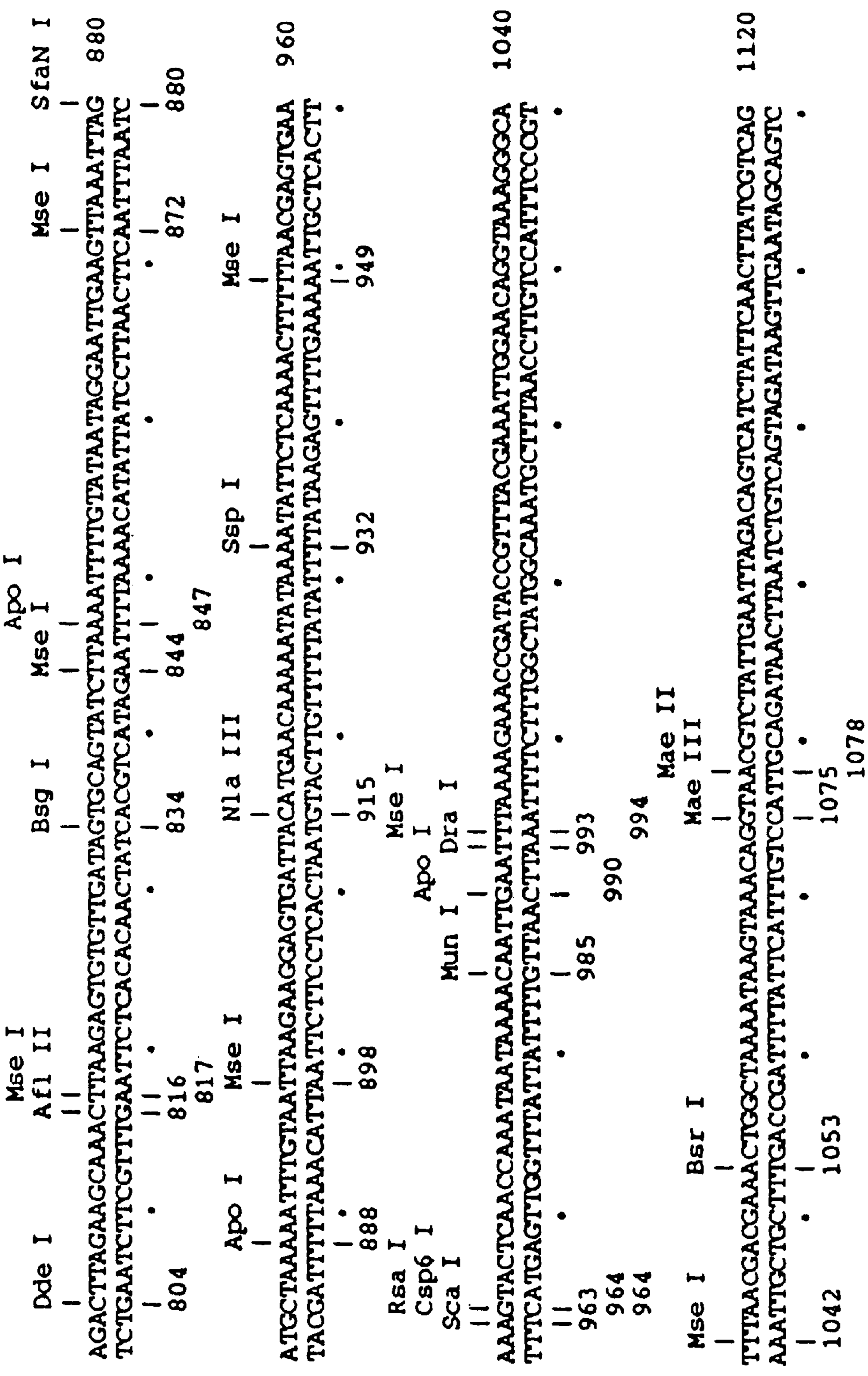
Figure 5A:
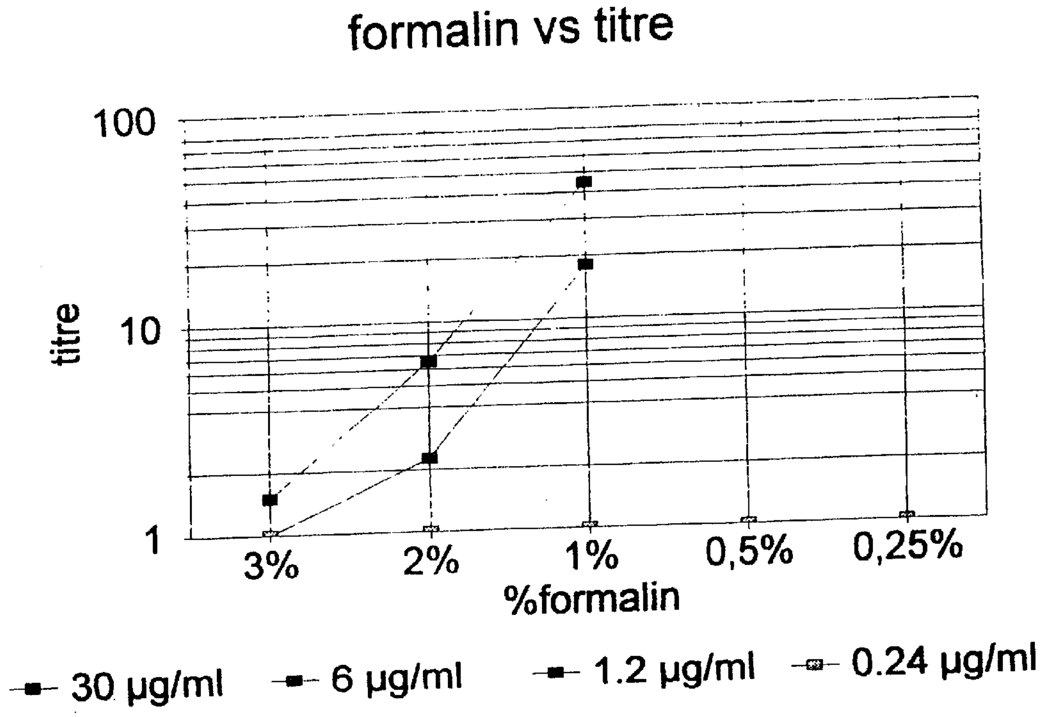
FIG. 5A: graph of the antigenicity titre versus formalin concentration.
Figure 5B:
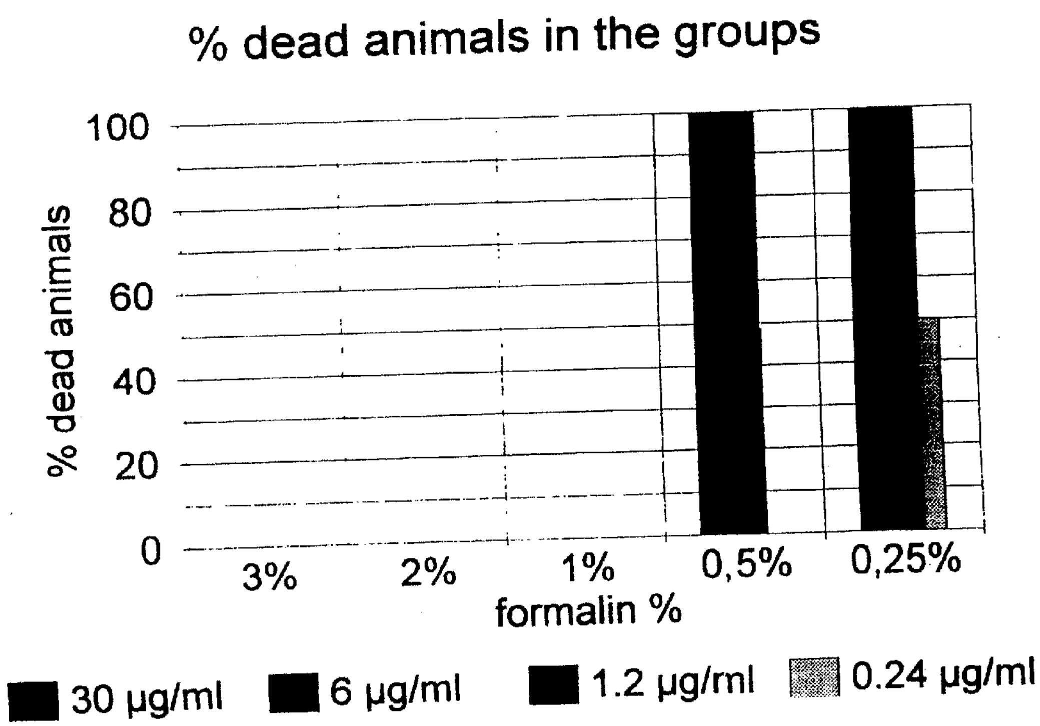
FIG. 5B: graph showing concentration of formalin versus animal death, and that 1% formalin is needed before detoxification is seen.

Mutant cpb genes were created by in vitro gene construction using PCR fragments amplified by Vent DNA polymerase from the original template cpb gene (cloned from *C. perfringens* type C) present in plasmid pJF2000 (as supplied by J. Frey). Primers used in this construction, and an example of the construction procedure used, are given in FIG. 3. The inclusion of BamHI sites on the 5' ends of the terminal cpbF2 and cpbR PCR primers allowed these mutants to be cloned into the BamHI site of the pKS90 expression plasmid (see above). The choice of PCR primers incorporating a BamHI site suitably spaced to the cpb ATG start codon, allowed the mutant cpb genes to be translationally coupled to the P11 TIR in pKS90. This method was used to generate a series of mutant expression strains. The exact sequences of these mutant genes (after cloning into pKS90) were determined by automatic sequencing with 3–4 fold redundancy, which confirmed both the gene sequences and location in the expression plasmids. Cloning the mutant genes in these vectors allowed secretion of the gene product into the culture supernatant by virtue of the native cpb N-terminal export leader. The culture supernatant was filter-sterilised and used directly in animal bioassays.

TABLE 1 mutant gene constructs.

| Construct | Mutation |
|---|---|
| pM1-4 | $D_{80}DK \rightarrow A_{80}AA$ |
| pM1-10 | $D_{80}DK \rightarrow A_{80}AA$ |
| | $Y_{182} \rightarrow H_{182}$ |
| pM2 | $T_{95}GF \rightarrow D_{95}DD$ |
| pM3-3 | $K_{101}KE \rightarrow A_{101}AA$ |
| | $T_{197} \rightarrow A_{197}$ |
| pM3-69 | $K_{101}KE \rightarrow A_{101}AA$ |
| pM4-3 | $P_{145}KN \rightarrow D_{145}ED$ |
| pM4-18 | $V_{62} \rightarrow I_{62}$ |
| | $P_{145}KN \rightarrow D_{145}ED$ |
| pM6-1 | $C_{292} \rightarrow A_{292}$ |
| (pM6-5) | |
| (pM6-7) | |
| pM6-16 | $C_{292} \rightarrow A_{292}$ |
| | $\Delta^{+}_{292}NWNGA$ |
| pM7-15 | $E_{287}RER \rightarrow Q_{287}QQQ$ |

Mutant Expression Strains

The pKS90-based toxoid expression plasmids are propagated in the specially disabled Lactococcal host strain, *L. lactis* MG1363 pep5- acmA-, but other Lactococcus strains can also be used. This strain represents a prophage and plasmid cured strain that is highly auxotrophic and unable to survive in the natural milk environment. In addition it grows at a slower rate than other lactococcal strains.

Non-toxic expression strains constructed as indicated above are represented in table 1. In this table, it is indicated which amino acids were mutated and where the mutations are located.

The toxoid expression strains can be grown in M17 medium (Difco cat. number 1856-17) supplemented with 0.5% w/v glucose and 5 g/ml erythromycin. Aeration is not required, indeed anoxic conditions are preferred although not essential. Optimal growth temperature is 30C. The various toxoid proteins produced by all these strains have been shown to accumulate in the culture medium to levels less than 5 g/ml. Western blot analysis using both monoclonal and polyclonal antibodies confirmed that protein monomer of the correct size is secreted into the supernatant by all the named expressor strains listed above. N-terminal sequencing of an example mutant protein, M4(4-3), confirmed that the leader peptide is correctly cleaved during export from the lactococcal cytoplasm.

Protocol for Random Mutagenesis of the cpb Gene

Typical PCR Reaction Mix is Set Up as Follows:

10 mM Tris-HCl (pH 8.7 at 25° C.)

50 mM KCl, 5 μg/ml bovine serum albumin 0.5 μM of each of the PCR primers (cpbf2: 5'-ggaggatccaaatgaagaaaaaatttatttcattagttatag-3') (SEQ ID NO: 3)

(cpbR: 5'-atggatccgtctaaatagctgttactttgtgag-3') (SEQ ID NO: 4)

4 mM $MgCl_2$ 0.5 mM $MnCl_2$ 3.4 mM forcing dNTP and 0.2 mM other 3 dNTPs (dNTP concentration may be ranged between 0.1 and 10 mM)

600 pM of template DNA (pJF2000 cpb clone or other cpb derivative) 2U Taq DNA polymerase Thermocycle Conditions Were as Follows:

(94° C. for 30 seconds, 50° C. for 60 second, 72° C. for 180 seconds) 30 cycles, followed by incubation at 72° C. for 600 seconds.

This reaction was performed using each of the 4 dNTPs as the forcing nucleotide and then pooled. This gives a suitably random mix of substitutions. The pooled PCR fragments were then BamHI digested and ligated into BamHI digested pKS90. This ligation mix was transformed into *Lactococus lactis* MG1 363. Transformants were grown in liquid culture and the filtered supernatants tested in the in vitro beta-toxin assay described in Example 3.

EXAMPLE 2

Culture of *Lactococcus lactis*

*L. lactis* producing gene modified β-toxin was grown in M17 medium (e.g. Difco cat. 1856-17), supplemented with 0.5% w/v glucose and 5 μg/ml erythromycin. Airation is not required, anoxic conditions are preferable although not essential. Optimal growth temperature is 30° C. Addition of glucose is necessary during the exponential growth.

Antigen Preparations

The culture supernatant was separated from the cells by means of centrifugation. After sterile filtration of the supernatant the derivatives were precipitated with ammonium sulphate (0.3 g/g). The precipitate was resuspended in PBS. As an alternative the culture supernatant can be concentrated on a filter <10,000 Da.

Mouse Lethality

Derivatives of β-toxin produced in *L. lactis* were initially tested by injection of sterile filtered culture supernatant, intraperitoneally, 0.5 ml in NRMI mice weighing approx. 20 g. Derivatives pM 6-1, 6-5, and 6-7 were lethal at a level similar to that of the native toxin. The derivatives pM 6-1, 6-5, and 6-7 have been modified in amino acid pos. $Cys_{292} \rightarrow Ala_{292}$.

TABLE 2

| Mouse lethality test | | |
|---|---|---|
| | dead/total (approx. in μg/ml) | |
| Derivative | sterile filtered supernatant | $(NH_4)_2SO_4$ conc. supernatant |
| pM 1-4 | 0/5 (5 μg/ml) | 2/2 (20 μg/ml) |
| pM 1-10 | 0/5 (5 μg/ml) | 2/2 (20 μg/ml) |
| pM 2 | 0/5 (1 μg/ml) | 1/2 (~4 μg/ml) |
| pM 3-3 | 0/5 (5 μg/ml) | 1/2 (30 μg/ml) |
| pM 3-64 | 0/5 (5 μg/ml) | 2/2 (30 μg/ml) |
| pM 4-3 | 0/5 (5 μg/ml) | 1/2 (30 μg/ml) |
| pM 4-18 | 0/5 (1.5 μg/ml) | 0/2 (30 μg/ml) |
| pM 6-1 | 5/5 (0.5 μg/ml) | 2/2 (50 μg/ml) |
| pM 6-5 | 5/5 (0.5 μg/ml) | 2/2 (50 μg/ml) |
| pM 6-7 | 5/5 (5 μg/ml) | 2/2 (50 μg/ml) |
| pM 6-16 | 0/5 (5 μg/ml) | 0/2 (50 μg/ml) |
| pM 7-15 | 0/5 (5 μg/ml) | 2/2 (40 μg/ml) |

In subsequent experiments the supernatants containing derivatives were precipitated with ammonium sulphate. Each derivative-containing sediment was resuspended in PBS in a 10× smaller volume. Each derivative was injected intraperitoneally mice. The derivatives pM 1-4, pM 1-10, pM 3-69 and pM 7-15 are all non-toxic at levels at which the wild-type toxin is lethal. They only become toxic at very high concentrations: 20–40 μg/ml. The derivatives pM 4-18 and pM 6-16 are also non-toxic at levels at which the wild-type toxin is lethal. They are not even toxic at even higher concentrations: 30–50 μg/ml. The remaining 3 derivatives pM 2, pM 3-3 and pM 4-3 were slightly toxic. (The $LD_{50}$ of the wild-type toxin is 0.15 μg/mouse). See also Table 2.

Dermonecrosis in Guinea Pigs

Albino guinea pigs of own breed, 300 g, were depilated in an area of 4×8 cm on both sides. 0.2 ml of extract was injected intradermally at 4 sites on each side of the animal. The animals were examined after 24, 48 and 72 hours and the lesion at the injection sites was scored. Obvious necrosis at the injection site (++++), severe erythema (+++), erythema (+++), reddening (+), no reaction (0).

The derivatives pM 1-4, 1-10, 3-3, 4-3, 6-16 and 7-15 are non-dermonecrotic even at very high concentrations.

The derivatives pM 6-1, 6-5, and 6-7 were dermonecrotic at a level of 5 μg/ml. They were not dermonecrotic at 0.5 μg/ml. After concentration the derivative pM 3-69 turned out to be dermonecrotic in dosages of 6 μg/ml, which corresponds to at least 60× less dermonecrotic than the native toxin. Derivative pM 4-18 has a 15× less dermonecrotic potential than that of the native toxin. Derivative pM 2 has not shown any dermonecrotic action by the tested concentrations of 1 μg/ml and 2 μg/ml respectively. Therefore pM2 is at least 20× less toxic than the native toxin. See also Table 3.

Vaccine Preparation

The antigen preparations were adjuvanted with Freund's incomplete adjuvant (50%), or Alhydrogen (20%), respectively.

TABLE 3

| | dermonecrosis in pigs. | |
|---|---|---|
| Derivative | Sterile filtered supernatant | $(NH_4)_2SO_4$ concentr. supernatant |
| 1-4 | 0 (5 μg/ml) | 0 (10 μg/ml<br>0 (4 μg/ml) |
| 1-10 | 0 (5 μg/ml) | 0 (10 μg/ml)<br>0 (4 μg/ml) |
| 2 | 0 (1 μg/ml) | 0 (2 μg/ml)<br>(+) (1 μg/ml) |
| 3-3 | 0 (5 μg/ml) | 0 (15 μg/ml)<br>0 (6 μg/ml) |
| 3-69 | 0 (5 μg/ml) | +++ (15 μg/ml)<br>++ (6 μg/ml) |
| 4-3 | 0 (5 μg/ml) | 0 (5 μg/ml)<br>0 (5 μg/ml) |
| 4-18 | 0 (1.5 μg/ml) | (+) (15 μg/ml)<br>0 (6 μg/ml) |
| 6-1 | ++++ (5 μg/ml)<br>0 (0.5 μg/ml) | n.d. |
| 6-5 | ++++ (5 μg/ml)<br>0 (0.5 μg/ml) | n.d. |
| 6-7 | ++++ (5 μg/ml | ++++ (10 μg/ml)<br>++ (2.5 μg/ml) |
| 6-16 | 0 (0.5 μg/ml) | 0 (25 μg/ml)<br>0 (20 μg/ml) |
| 7-15 | 0 (5 μg/ml)<br>0 (5 μg/ml) | 0 (20 μg/ml)<br>0 (8 μg/ml) |
| CpC β | +++ (0.1 μg/ml) | |

0 no reaction
+ reddening
++ erythema
+++ severe erythema
++++ obvious necrosis at injection site
CpC β Clostridium perfringens type C β-toxin Immunization of Pigs The derivative 3-69 was prepared in a concentration of approx. 40 μg/ml and adjuvanted to a final concentration of 20 μg/ml. The pigs were given 2 ml intramuscularly at 2 weeks interval. Blood samples were taken before 1st vaccination, before 2nd vaccination and 2 weeks after 2nd vaccination. The pigs were observed for side effects 24 h after 1st vaccination. No side effects were observed.

EXAMPLE 3

Quick Screening Test for the Detection of Non-toxic Derivatives of β-toxin Obtained from Randomly Mutagenised β-toxin-genes Procedure for BT-cell Test A culture of trypsinated BT (Bovine Turbinate cells) cells, $1.5\times10^5$ cells/ml, in Eagles medium with 5% calf serum, was transferred to a 96-wells microtiter plate, 100 μl/well. The plates were incubated for 24 hours at 37° C. and 3% $CO_2$. Samples of β-toxin to be tested were diluted in 20° C. PBS pH 7.0 in dilution plates. The medium was cautiously discarded from the cells and 100 μl of β-toxin dilutions were applied per well. The cells were then incubated for 30 min. at 37° C. and 3% $CO_2$. The samples were cautiously discarded and fresh Eagles medium with 5% calf serum tempered to 37° C. was added. The cells were incubated for three days under the same conditions as mentioned above. Then the medium was discarded from the microtiter plates and Giemsa staining solution 5 μl/well was added. After 10 minutes the staining agent was discarded and the plate was washed 3× with water and allowed to stand for at least 20 minutes for drying.

All wells were checked for the presence of multinucleate cells and irregularities in the monolayer. Lack of these signs in a specific well is indicative for the presence in that well of a non-toxic derivative β-toxin. Those β-toxin derivatives that proved non-toxic were tested for their immunogenicity in the semi-quantitative ELISA test described below.

Semi-quantitative ELISA

Highly specific antibodies raised against native *Clostridium perfringens* β-toxin in rabbits were purified on a protein A column and ELISA plates were coated with approximately 2 μg/ml of these specific antibodies. The supernatants containing the β-toxin derivatives were added to the plates in 3-fold dilutions. After incubation for 1 hour, horseradish peroxidase conjugated polyclonal rabbit anti-C.p.β-toxin antibodies were used for detection.

Those β-toxin derivatives that reacted in the ELISA to a titer not less than 1000 times lower than the native β-toxin were considered to be the desired non-toxic and still immunogenic derivatives of β-toxin according to the invention.

EXAMPLE 4

Vaccination Experiments in Pigs

Preparation of Vaccine

Derivative pM 1-4 was produced by Lactococcus lactis strain pM 1-4. After fermentation the cells were removed by centrifugation (100000×g for 35 min.). Then, 0.31 g ammonium sulphate was added to each g of supernatant. The mixture was placed at 4° C. for 3 hours for precipitation. After centrifugation at 100000×g for 45 min. the precipitate was dissolved in 1/30 of the original volume and dialysed against PBS. The final content of derivative pM 1-4 was quantified by SDS-PAGE relative to BSA standards. Finally the derivative solution was mixed with Diluvac Forte® in a ratio of 1:1. The final concentration of pM 1-4 in the vaccine was 80 μg/ml.

Vaccination

Five pigs aged 5 weeks were used. The pigs were vaccinated with 2 ml intramuscularly on days 0 and 21.

Observations

The animals' general condition was recorded during the initial three hours after vaccination according to the following scale:

0=no symptoms
1=mildly depressed, rough coated (for less than 1 hour)
2=depressed, shivering (less than 1 hour)
3=depressed, shivering, lying down and limited water intake (less than 1 hour)
4=vomiting, severely depressed (less than 1 hour)
5=depressed for more than one hour and does not eat the following feeding Blood Sampling and Determination of Titers Blood samples were taken before $1^{st}$ vaccination (day 0), before $2^{nd}$ vaccination (day 21) and two weeks after $2^{nd}$ vaccination (day 35) and analysed for anti-β-toxin antibodies by competitive ELISA. Briefly described, monoclonal antibody raised against native β-toxin was coated in an ELISA plate. Serial dilution of sera was allowed to react with a fixed concentration of the β-toxin on a separate plate. The mixtures of toxin and antibodies containing sera were transferred to the Mab coated plate and remaining native β-toxin contents were determined. The titres were calculated as 50% inhibition of uninhibited β-toxin, relative to WHO antitoxin standard 1959.

Results

Observations

The pigs did not show any clinical reaction due to any of the vaccinations. See table 4.

Serology

One pig (no. 52) responded to $1^{st}$ vaccination. After the second vaccination all four pigs seroconverted and the average anti-β-toxin titer was 66 i.u. measured in ELISA.

Individual titers appear from Table 4.

TABLE 4

Anti-β-toxin antibody response in pigs
Anti-β-toxin antibody response in pigs measured in ELISA in i.u. and score in test for non-specific toxicity.

| Pig No. | Pre-immune sera (i.u.) | After $1^{st}$ vaccination (i.u.) | After $2^{nd}$ vaccination (i.u.) | Non-spec. tox score |
|---|---|---|---|---|
| 51 | 0 | 0 | 159.6 | 0 |
| 52 | 0 | 2.4 | 55.1 | 0 |
| 54 | 0 | 0 | 32.2 | 0 |
| 55 | 0 | 0 | 17.3 | 0 |

Conclusion

All pigs responded to vaccination with genetically modified β-toxin by producing β-toxin-inhibiting anti-β-toxin antibodies.

We claim:

1. A detoxified immunogenic derivative of *Clostridium perfringens* β-toxin or an immunogenic fragment thereof capable of inducing the production of β-toxin-inhibiting anti-β-toxin antibodies in an animal immunized therewith, comprising a *Clostridium perfringens* β-toxin having a mutation in its amino acid sequence, which mutation is not found in wild-type β-toxin.

2. The derivative of *Clostridium perfringens* β-toxin or an immunogenic fragment thereof according to claim 1, wherein the mutation is a replacement mutation.

3. The derivative of *Clostridium perfringens* β-toxin or an immunogenic fragment thereof according to claim 1, wherein the mutation is an insertion and/or deletion.

4. The derivative of *Clostridium perfringens* β-toxin or an immunogenic fragment thereof according to claim 1, wherein the mutation is located in a transition domain between neutral parts of the amino acid sequence encoding the β-toxin and parts having highest local hydrophilicity as determined by the Hopp-Woods algorithm.

5. The derivative of *Clostridium perfringens* β-toxin or an immunogenic fragment thereof according to claim 1, wherein the mutation is located in the β-toxin of SEQ ID NO: 29 at position 62, 182, 197 or in one of the regions between amino acid numbers 80–103, 145–147, 281–291, 295–299 or downstream of amino acid position 292.

6. The derivative of *Clostridium perfringens* β-toxin or an immunogenic fragment thereof according to claim 1, wherein the mutation is located in one of the regions between amino acid numbers 80–82, 95–97, 101–103 or 287–291 of the β-toxin of SEQ ID NO: 29.

7. An immunogenic composition comprising a derivative of *Clostridium perfringens* β-toxin or an immunogenic fragment thereof according to claim 1, and a physiologically acceptable carrier.

8. The immunogenic composition according to claim 7, further comprising an adjuvant.

9. The immunogenic composition according to claim 7, further comprising at least one immunogen from at least one other pathogen.

10. The immunogenic composition according to claim 9, wherein said at least one immunogen from at least one other pathogen is selected from the group consisting of *Actinobacillus pleuropneumoniae, Pseudorabies virus, Porcine Influenza virus*, Porcine Parvovirus, Transmisible Gastroenteritis virus, rotavirus, *Escherichia coli, Erysipelothrix rhusiopathiae, Pasteurella multocida, Bordetella bronchiseptica, Salmonella species, Mycoplasma hyopneumoniae, Haemophilis parasuis* and *Helicobacter bacteria.*

11. A method for the preparation of an immunogenic composition comprising admixing a derivative of *Clostridium perfringens* β-toxin according to claim 1, with a physiologically acceptable carrier.

12. The immunogenic composition of claim 7, wherein the mutation is a replacement mutation.

13. The immunogenic composition of claim 7, wherein the mutation is an insertion and/or deletion mutation.

14. The immunogenic composition of claim 7, wherein the mutation is located in a transition domain between neutral parts of the amino acid sequence encoding the β-toxin and parts having highest local hydrophilicity as determined by the Hopp-Woods algorithm.

* * * * *